(12) United States Patent
Jovanovich et al.

(10) Patent No.: US 11,441,976 B2
(45) Date of Patent: Sep. 13, 2022

(54) METHOD AND APPARATUS FOR PROCESSING TISSUE SAMPLES

(71) Applicant: S2 Genomics, Inc., Livermore, CA (US)

(72) Inventors: Stevan Bogdan Jovanovich, Livermore, CA (US); Frank Zaugg, Redwood City, CA (US); Kaiwan Chear, Livermore, CA (US); Roger McIntosh, San Ramon, CA (US); Nathan Pereira, Pleasanton, CA (US)

(73) Assignee: S2 GENOMICS, INC., Livermore, CA (US)

( * ) Notice: Subject to any disclaimer, the term of this patent is extended or adjusted under 35 U.S.C. 154(b) by 0 days.

(21) Appl. No.: 17/513,204

(22) Filed: Oct. 28, 2021

(65) Prior Publication Data

US 2022/0082479 A1 Mar. 17, 2022

Related U.S. Application Data

(63) Continuation of application No. 16/301,249, filed as application No. PCT/US2017/063811 on Nov. 29, 2017, now Pat. No. 11,231,347.

(Continued)

(51) Int. Cl.
  *G01N 1/31* (2006.01)
  *C12M 1/00* (2006.01)
  (Continued)

(52) U.S. Cl.
  CPC ............... *G01N 1/31* (2013.01); *C12M 47/04* (2013.01); *C12M 47/06* (2013.01); *C12N 1/06* (2013.01);
  (Continued)

(58) Field of Classification Search
  None
  See application file for complete search history.

(56) References Cited

U.S. PATENT DOCUMENTS

| 4,307,846 A | 12/1981 | Spelsberg |
| 5,114,858 A | 5/1992 | Williams et al. |
| (Continued) | | |

FOREIGN PATENT DOCUMENTS

| EP | 2540394 A1 | 1/2013 |
| EP | 3548603 A1 | 10/2019 |
| (Continued) | | |

OTHER PUBLICATIONS

European Patent Office, Extended European Search Report EP 17875198.8, dated Sep. 29, 2020, 11 pages.

(Continued)

*Primary Examiner* — Jyoti Nagpaul
(74) *Attorney, Agent, or Firm* — Storella, P.C.; John R. Storella

(57) ABSTRACT

A system, methods, and apparatus are described to collect and prepare single cells, nuclei, subcellular components, and biomolecules from specimens including tissues. The system can perform enzymatic and/or physical disruption of the tissue to dissociate it into single-cells or nuclei in suspension or subcellular components including nucleic acids. In some embodiments, the titer of dissociated cells is monitored at intervals and the viability determined. In some embodiments, the processing is adjusted according to the measurements of the titer and viability. In some embodiments, the single-cells or nuclei in suspension are washed and resuspended in the buffer or media of choice. In some embodiments, the conditions are chosen to produce nuclei. In other embodiments, the single-cells or nuclei are purified by affinity paramagnetic bead processing. In some embodiments, matched bulk nucleic acid to the single-cells is (Continued)

produced. In other embodiments, single-cell libraries, or nuclei libraries, or matched bulk libraries, or bulk libraries are produced. The single cells or nuclei can then be further processed by FACS, DNA sequencing, mass spectrometry, fluorescence, or other methods. In other embodiments, the tissue processing is integrated with an analytical system to produce a sample-to-answer system such as a tissue-to-genomics system.

30 Claims, 47 Drawing Sheets

Related U.S. Application Data

(60) Provisional application No. 62/427,150, filed on Nov. 29, 2016, provisional application No. 62/526,267, filed on Jun. 28, 2017.

(51) Int. Cl.
*C12Q 1/6851* (2018.01)
*C12N 1/06* (2006.01)
*C12N 15/10* (2006.01)
*G01N 1/28* (2006.01)

(52) U.S. Cl.
CPC ......... *C12N 1/066* (2013.01); *C12N 15/1003* (2013.01); *C12Q 1/6851* (2013.01); *G01N 1/286* (2013.01); *G01N 2001/2866* (2013.01)

(56) References Cited

U.S. PATENT DOCUMENTS

| | | | |
|---|---|---|---|
| 5,234,809 A | 8/1993 | Boom et al. | |
| 5,665,554 A | 9/1997 | Reeve et al. | |
| 5,898,071 A | 4/1999 | Hawkins | |
| 5,952,215 A | 9/1999 | Dwulet et al. | |
| 6,190,616 B1 | 2/2001 | Jovanovich et al. | |
| 6,391,541 B1 | 5/2002 | Petersen et al. | |
| 6,534,262 B1 | 3/2003 | McKernan et al. | |
| 6,551,839 B2 | 4/2003 | Jovanovich et al. | |
| 7,244,961 B2 | 7/2007 | Jovanovich et al. | |
| 8,288,106 B2 | 10/2012 | Fekete et al. | |
| 8,536,322 B2 | 9/2013 | Han | |
| 8,815,521 B2 * | 8/2014 | Taylor | B01L 3/5027 435/259 |
| 8,936,933 B2 | 1/2015 | Chen et al. | |
| 9,347,086 B2 | 5/2016 | Connolly et al. | |
| 2002/0197631 A1 | 12/2002 | Lawrence et al. | |
| 2003/0066915 A1 | 4/2003 | Taylor | |
| 2003/0157523 A1 | 8/2003 | Frantz et al. | |
| 2003/0170617 A1 | 9/2003 | Pasloske | |
| 2004/0086872 A1 | 5/2004 | Childers et al. | |
| 2005/0070941 A1 | 3/2005 | Isogimi | |
| 2005/0070944 A1 | 3/2005 | Holl et al. | |
| 2005/0287670 A1 | 12/2005 | Gulliver et al. | |
| 2006/0030796 A1 | 2/2006 | Xu et al. | |
| 2008/0050814 A1 | 2/2008 | Allickson | |
| 2008/0306610 A1 | 12/2008 | Wang et al. | |
| 2008/0307904 A1 | 12/2008 | Pressman et al. | |
| 2011/0206646 A1 | 8/2011 | Alfonso et al. | |
| 2014/0057255 A1 | 2/2014 | Holmes | |
| 2014/0377880 A1 | 12/2014 | Emburgh et al. | |
| 2016/0116439 A1 | 4/2016 | Kindwall et al. | |
| 2017/0106366 A1 | 4/2017 | Gross et al. | |
| 2017/0292151 A1 | 10/2017 | Connolly et al. | |
| 2018/0119218 A1 | 5/2018 | Bashir et al. | |
| 2019/0212233 A1 | 7/2019 | Jovanovich et al. | |

FOREIGN PATENT DOCUMENTS

| | | |
|---|---|---|
| WO | 0194911 A2 | 12/2001 |
| WO | 2014153072 A1 | 9/2014 |
| WO | 2017075293 A1 | 5/2017 |
| WO | 2017116694 A1 | 7/2017 |
| WO | 2018102471 A1 | 6/2018 |
| WO | 2019232504 A3 | 1/2020 |
| WO | 2021236666 A1 | 11/2021 |

OTHER PUBLICATIONS

European Patent Office, Partial Supplementary European Search Report FOR 17875198.8, dated Jun. 25, 2020, 14 pages.
ISA/US, International Search Report and Written Opinion for PCT/US2017/063811 dated Mar. 29, 2018, 15 pgs.
ISA/US, International Search Report and Written Opinion for PCT/US2019/035097 dated Dec. 6, 2019, 16 pgs.
International Search Report and Written Opinion of PCT/US2020/033001 dated Oct. 29, 2021, 16 pages.
Supplementary Partial European Search Report for EP19811211 dated Mar. 24, 2022, 3 pages.
U.S. Appl. No. 15/734,128, Final Office Action dated Apr. 18, 2022, 30 pages.
U.S. Appl. No. 17/581,940, Non-Final Office Action dated Apr. 20, 2022, 7 pages.

* cited by examiner

Figure 11
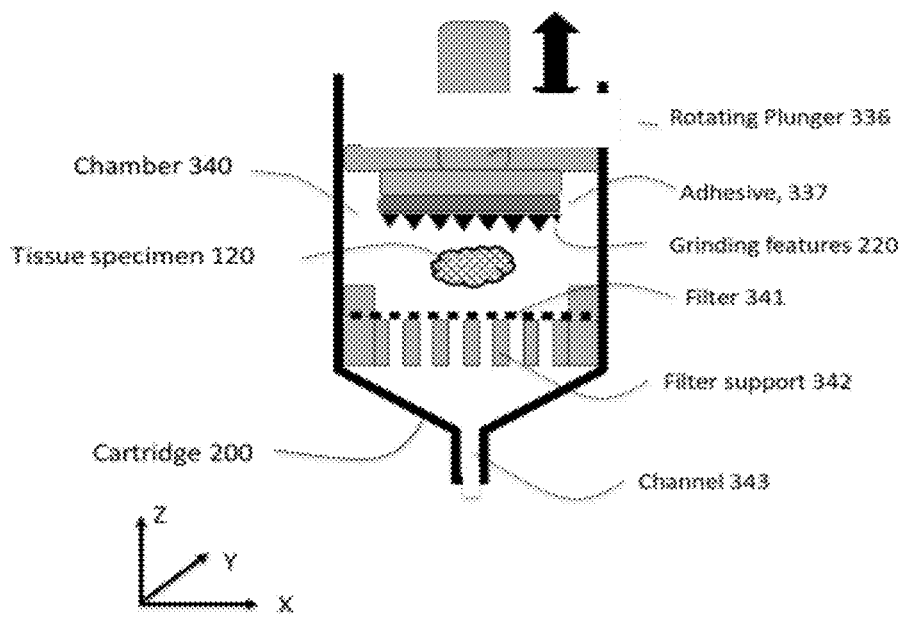
Figures 12 A-C
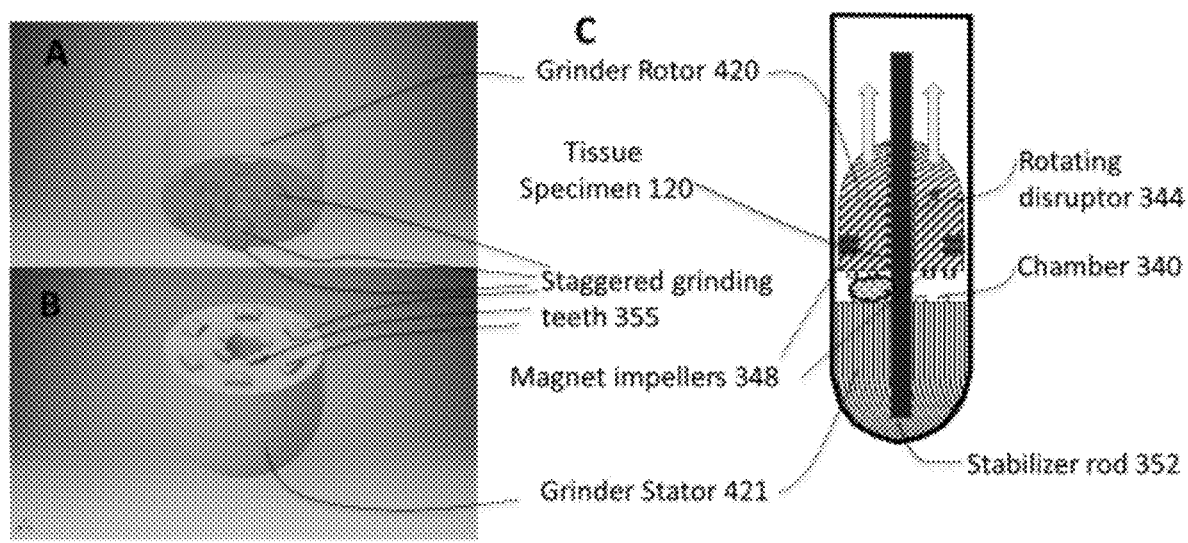

Figures 15A-D
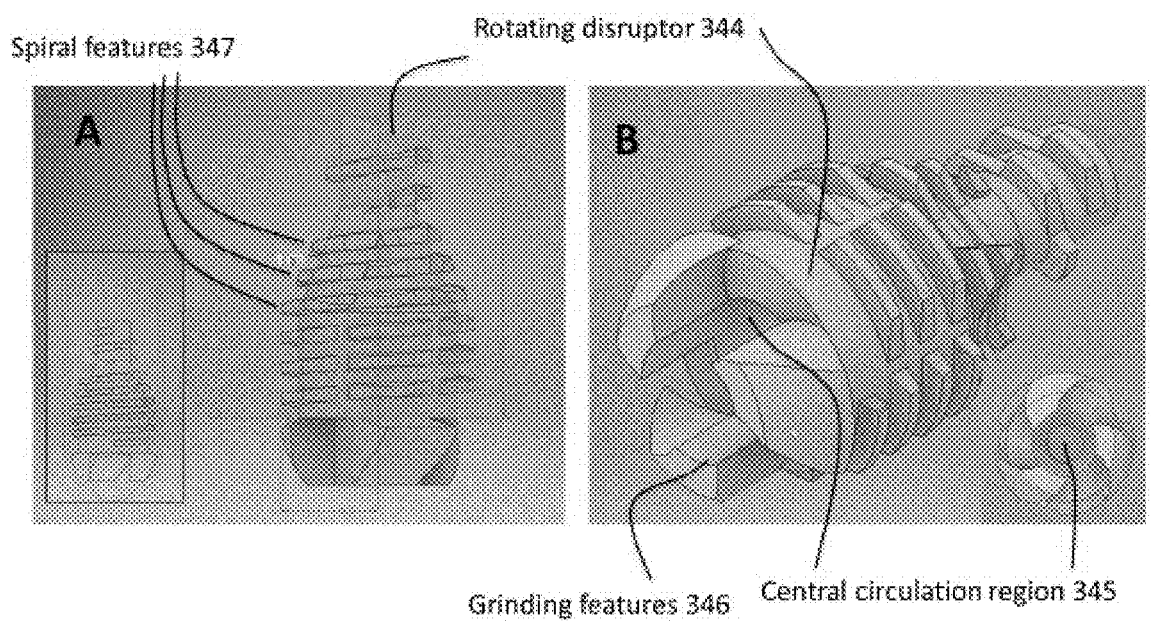
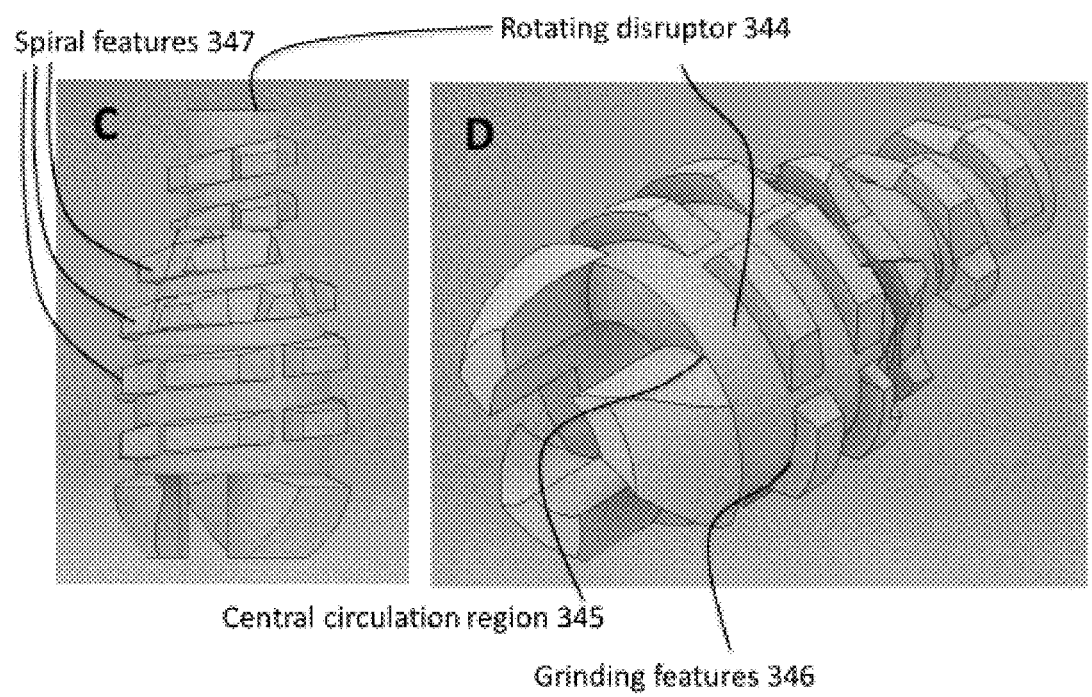

Figures 16 A-E
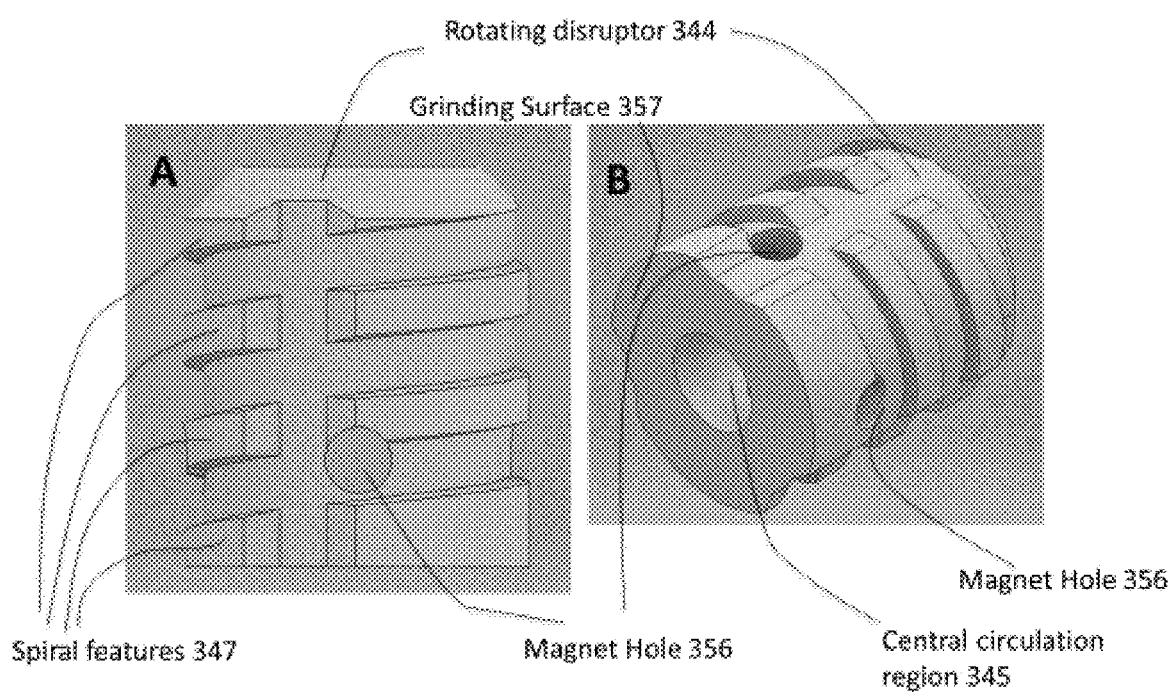
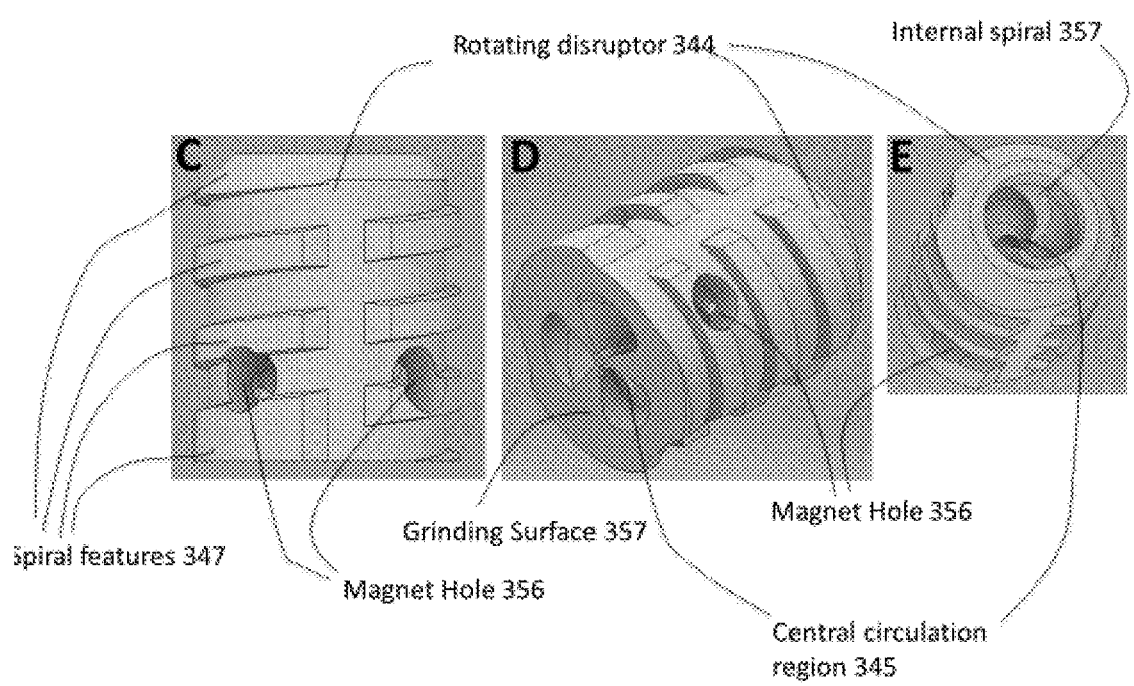

Figures 17 A-D
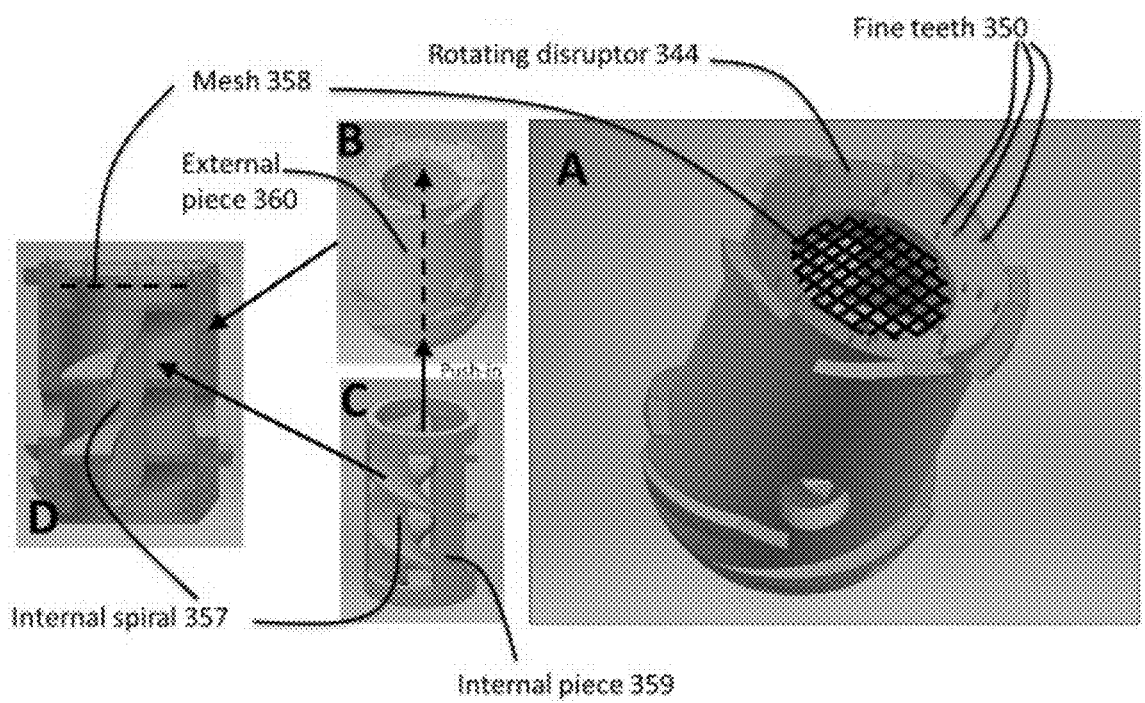
Figure 18
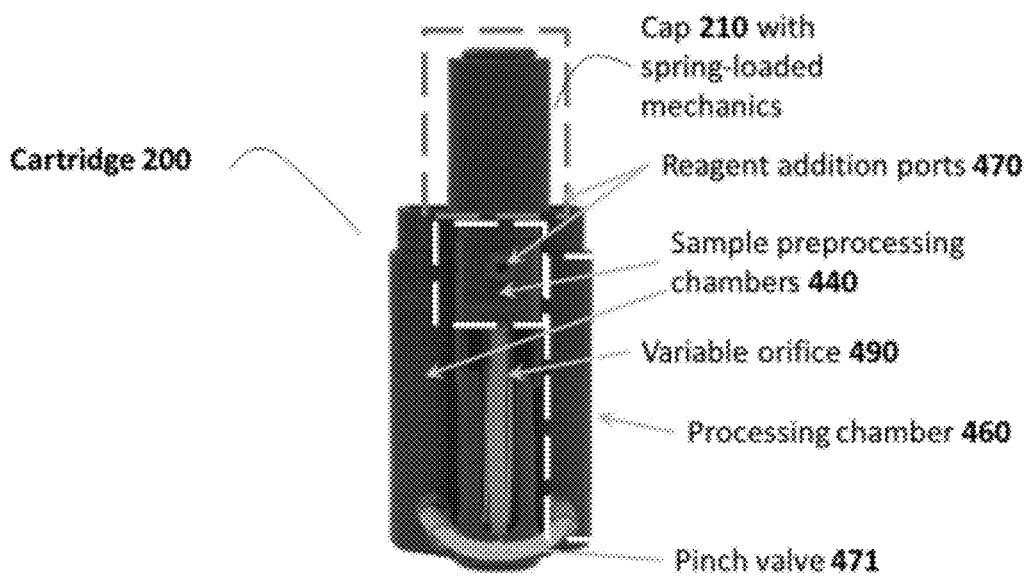

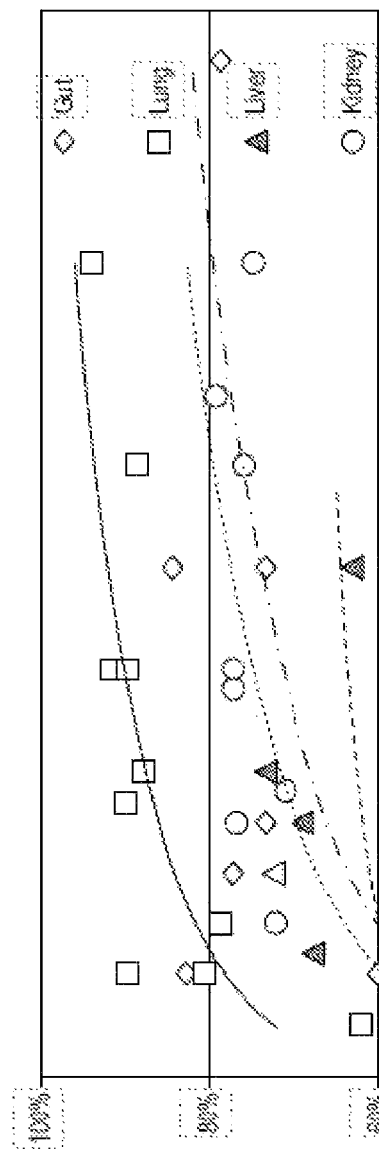
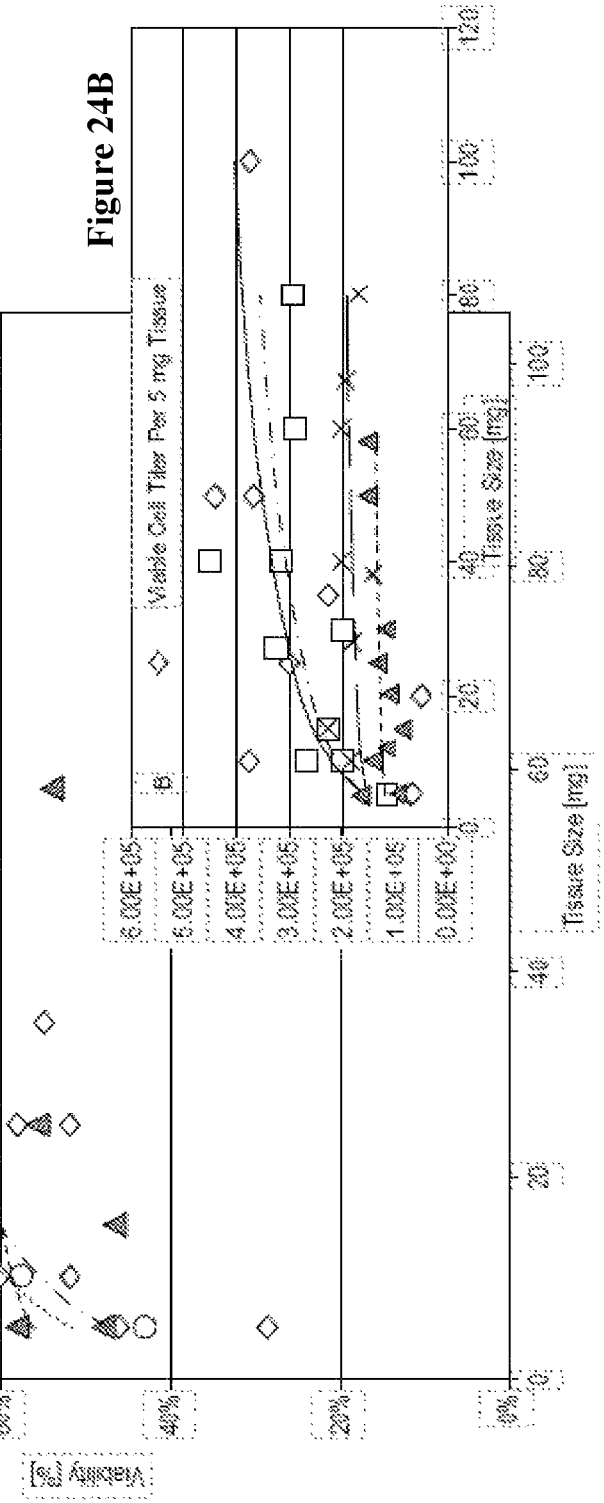
Figure 24A
Figure 24B

METHOD AND APPARATUS FOR PROCESSING TISSUE SAMPLES

CROSS REFERENCE TO RELATED APPLICATIONS

This application is a continuation of and claims priority to U.S. application Ser. No. 16/301,249, filed on Nov. 13, 2018 (Jovanovich, Zaugg, Chear, McIntosh and Pereira, "Method and Apparatus for Processing Tissue Samples"), which claims the benefit of international application PCT/US17/63811, filed on Nov. 29, 2017 (Jovanovich, Zaugg, Chear, McIntosh and Pereira, "Method and Apparatus for Processing Tissue Samples"), which claims the priority date of provisional patent application 62/526,267, filed Jun. 28, 2017, (Jovanovich, Chear, McIntosh, Pereira, and Zaugg, "Method and Apparatus for Producing Single Cell Suspensions and Next Generation Sequencing Libraries for bulk DNA and Single-Cells from Tissue and Other Samples"), which also claims the priority date of provisional patent application, 62/427,150, filed Nov. 29, 2016, (Jovanovich, Zaugg, Chear, Wagner, Kernen, and McIntosh, "Method and Apparatus for Producing Single Cell Suspensions from Tissue and Other Samples), the contents of which are incorporated herein in their entirety and the benefit of the priority date of provisional patent applications.

STATEMENT OF FEDERALLY SPONSORED RESEARCH OR DEVELOPMENT (IF ANY)

None.

The Names of the Parties to a Joint Research Agreement if the Claimed Invention was Made as a Result of Activities within the Scope of a Joint Research Agreement None.

REFERENCE TO A "SEQUENCE LISTING"

None.

BACKGROUND OF THE INVENTION

A) Field of Invention

This invention relates to the field of sample preparation from biological materials. More specifically, the invention relates to the processing of solid tissues into single cells, nuclei, biomolecules, and processed samples for bioanalysis.

B) Description of Related Art

Analysis of single cells and groups of cells is now beginning to provide information to dissect and understand how cells function individually and unprecedented insight into the range of individual responses aggregated in ensemble measurements. Single cell methods for electrophysiology, flow cytometry, imaging, mass spectrometry (Lanni, E. J., et. al. J Am Soc Mass Spectrom. 2014; 25(11):1897-907), microarray (Wang L and KA Janes. Nat Protoc. 2013; 8(2):282-301), and Next Generation Sequencing (NGS) (Saliba A. E., et. al. Nucleic Acids Res. 2014; 42(14):8845-60) have been developed and are driving an increased understanding of fundamental cellular processes, functions, and interconnected networks. As the individual processes and functions are understood and differentiated from ensemble measurements, the individual information can in turn lead to discovery of how network processes among cells operate. The networks may be in tissues, organs, multicellular organisms, symbionts, biofilms, surfaces, environments, or anywhere cells interact.

Next Generation Sequencing (NGS) of single cells is rapidly changing the state of knowledge of cells and tissue, discovering new cell types, and increasing understanding of the diversity of how cells and tissue function. Single cell NGS RNA sequencing (Saliba A. E., et. al., Nucleic Acids Res. 2014; 42(14):8845-60) (Shapiro E. et. al., Nat Rev Genet. 2013; 14(9):618-30) is unveiling the complexity of cellular expression, and the heterogenity from cell to cell, and from cell type to cell type (Buettner F. et. al., Nat Biotechnol. 2015; 33(2):155-60). In situ sequencing (Ke R et. al., Nat Methods. 2013; 10(9):857-60), (Lee J H, et. al., Nat Protoc. 2015; 10(3):442-58) (Lee J H, et. al., Science. 2014, 21; 343(6177):1360-3) has shown the feasability of directly sequencing of fixed cells. However, for RNA, many fewer reads are generated with in situ sequencing, biasing against detection of low abundant transcripts. Photoactivatable tags have been used to capture mRNA from single cells (Lovatt, D., et. al., Nat Methods. 2014; 11(2):190-6) from known location in tissue, albeit with low throughput capture and manual cell collection.

The NGS market has grown explosively over the last 10 years with costs reductions and throughput increases exceeding Moore's law. The applications have expanded from whole genome sequencing to RNA-Seq, ChIP-Seq, exome sequencing, to now single-cell sequencing, single nuclei sequencing, and many other exciting applications. The power and low cost of NGS is broadly changing life sciences and moving into translational medicine and the clinic as precision medicine begins. Until recent years essentially all of the NGS analysis was of 'bulk samples' where the nucleic acids of numerous cells had been pooled. There is a need for systems that integrate the sample preparation of single-cell suspensions, and single-cell libraries, and bulk libraries starting from original unprocessed specimens.

Single-cell sequencing is rapidly changing the state of knowledge of cells and tissue, discovering new cell types, and increasing the understanding of the diversity of how cells and tissue function. Single-cell RNA sequencing (Shapiro E. Biezuner T, Linnarsson S. Single-cell sequencing-based technologies will revolutionize whole-organism science. Nat Rev Genet. 2013; 14(9):618-30. PMID: 23897237) has highlighted the complexity of cellular expression, and the large heterogeneity from cell-to-cell, and from cell type-to-cell type (Buettner F. Natarajan K N, Casale F P, Proserpio V, Scialdone A, Theis F J, Teichmann S A, Marioni J C, Stegle O. Computational analysis of cell-to-cell heterogeneity in single-cell RNA-sequencing data reveals hidden subpopulations of cells. Nat Biotechnol. 2015; 33(2):155-60. PMID: 25599176). Single-cell sequencing (Wang., Y. and N. E. Navin. Advanced and Applications of single-cell sequencing technologies. Molecular Cell. 2015. 58:598-609. PMID 26000845) is being applied to development, brain structure and function, tumor progression and resistance, immunogenetics, and more.

Single cell nucleic acid sequencing technology and methods using NGS and Next Next Generation Sequencing (NNGS), such as nanopores, are rapidly evolving. Common components are incorporation of a marker or barcode for each cell and molecule, reverse transcriptase for RNA sequencing, amplification, and pooling of sample for NGS and NNGS (collectively termed NGS) library preparation and analysis. Starting with isolated single cells in wells, barcodes for individual cells and molecules have been incorporated by reverse transcriptase template switching before pooling and polymerase chain reaction (PCR) amplification (Islam S. et. al. Genome Res. 2011; 21(7):1160-7) (Ramskold D. et. al. Nat Biotechnol. 2012; 30(8):777-82) or on a barcoded poly-T primer with linear amplification (Hashimshony T. et. al. Cell Rep. 2012 Sep. 27; 2(3):666-73) and unique molecular identifiers (Jaitin D. A. et. al. Science. 2014; 343(6172):776-9).

Recent pioneering work has used the power of nanodroplets to perform highly parallel processing of mRNA from single cells with reverse transcription incorporating cell and molecular barcodes from freed primers (inDrop) (Klein A. M. et. al. Cell. 2015; 161(5):1187-201) or primers attached to paramagnetic beads (DropSeq) (Macosko E. Z. et. al. Cell. 2015; 161(5):1202-14) and using micronozzles such as described by them or Geng T. et. al. Anal Chem. 2014; 86(1):703-12 or others, and; the lysis conditions and reverse transcriptase described by (Fekete R. A. and A. Nguyen. U.S. Pat. No. 8,288,106. Oct. 16, 2012) are incorporated by reference cited therein are incorporated by reference, including instrumentation, chemistry, workflows, reactions conditions, flowcell design, and other teachings. Both inDrop and DropSeq are scalable approaches have change the scale from 100s of cells previously analyzed to 1,000s and more.

Single-cell sequencing is now providing new information to biologists, genomic scientists, and clinical practitioners, and the single-cell market is growing explosively, perhaps the next great disruption in life sciences and medicine. Multiple companies are providing systems to take single-cell suspensions and create Single-cell RNA sequencing (scRNA-Seq) libraries that are analyzed by the robust NGS sequencing and analysis pipeline. No system integrates the upstream process to produce single-cell suspensions for NGS single-cell sequencing or has integrated from tissue to single-cell libraries.

The production of single-cells or nuclei or nucleic acids from solid and liquid tissue is usually performed manually with a number of devices used without process integration. A combination of gentle mechanical disruption with enzymatic dissociation has been shown to produce single-cells with the highest viability and least cellular stress response (Quatromoni J G, Singhal S, Bhojnagarwala P, Hancock W W, Albelda S M, Eruslanov E. An optimized disaggregation method for human lung tumors that preserves the phenotype and function of the immune cells. J Leukoc Biol. 2015 January; 97(1):201-9. doi: 10.1189/jlb.5TA0814-373. Epub 2014 Oct. 30).

Many manual protocols for dissociating different tissues exist, for example, Jungblut M., Oeltze K., Zehnter I., Hasselmann D., Bosio A. (2009). Standardized Preparation of Single-Cell Suspensions from Mouse Lung Tissue using the gentleMACS Dissociator. JoVE. 29, doi: 10.3791/1266; Stagg A J, Burke F, Hill S, Knight S C. Isolation of Mouse Spleen Dendritic Cells. Protocols, Methods in Molecular Medicine. 2001: 64: 9-22. Doi: 10.1385/1592591507; Lancelin, W., Guerrero-Plata, A. Isolation of Mouse Lung Dendritic Cells. J. Vis. Exp. (57), e3563, 2011. DOI: 10.3791/3563; Smedsrod B, Pertoft H. Preparation of pure hepatocytes and reticuloendothelial cells in high yield from a single rat liver by means of Percoll centrifugation and selective adherence. J Leukocyte Biol. 1985: 38: 213-30; Meyer J, Gonelle-Gispert C, Morel P, Buhler L Methods for Isolation and Purification of Murine Liver Sinusoidal Endothelial Cells: A Systematic Review. PLoS ONE 11(3) 2016: e0151945. doi:10.1371/journal.pone.0151945; Kondo S. Scheef E A, Sheibani N, Sorenson C M. "PECAM-1 isoform-specific regulation of kidney endothelial cell migration and capillary morphogenesis", Am J Physiol Cell Physiol 292: C2070-C2083, (2007); doi: 10.1152/ajpcell.00489.2006; Ehler, E., Moore-Morris, T., Lange, S. Isolation and Culture of Neonatal Mouse Cardiomyocytes. J. Vis. Exp. (79), e50154, doi:10.3791/50154 (2013); Volovitz I Shapira N, Ezer H, Gafni A, Lustgarten M, Alter T, Ben-Horin I, Barzilai O, Shahar T, Kanner A, Fried I, Veshchev I, Grossman R, Ram, Z. A non-aggressive, highly efficient, enzymatic method for dissociation of human brain-tumors and brain-tissues to viable single cells. BMC Neuroscience (2016) 17:30 doi: 10.1186/s12868-016-0262-y; F. E Dwulet and M. E. Smith, "Enzyme composition for tissue dissociation," U.S. Pat. No. 5,952,215, Sep. 14, 1999.

For example, solid tissue of interest is usually dissected and then minced into 1-5 mm pieces by hand or a blender type of disruptor is used. Enzymes or a mixture of enzymes, such as collagenases, hydrauronadase, papain, proteases, DNase, etc., are added and the specimen incubated, typically with shaking or rotation to aid dissociation to prepare single cells or nuclei from tissue. In many procedures, the specimen is titurated multiple times or mechanically disrupted. The mechanical disruption may be through orifices, grinding, homogenization, forcing tissue through screens or filters, sonication, blending, bead-beating, rotors with features that dissociate tissue, and other methods to physically disrupt tissue to help produce single cells.

Following dissociation, in some embodiments the dissociated sample is passed through a filter, such as a 70 □m filter, to retain clumps of cells or debris. The filtrate which contains single cells or nuclei may be further processed to change the media or buffer; add, remove, or deactivate enzymes; concentrate cells or biomolecules, lyse red blood cells, or capture specific cell types. The processing typically involves multiple steps of centrifugation and resuspension, density gradients, or magnetic bead capture of specific cell types using antibodies or other affinity capture ligands, or fluorescent cell-activated sorting (FACS). The titer and viability of the single-cell suspension is usually determined using optical imaging with a microscope and haemocytometer, or an automated instrument. In many cases, the viability is determined using Trypan blue or fluorescent dyes. Quality control can include characterization of the nucleic acids by gel electrophoresis on an instrument such as a BioAnalyzer, or the determination of the expression of certain genes using reverse transcripatase and quantitative polymerase chain reaction (RT-qPCR), or other relevant methods.

The rapid production of nuclei can give a snapshot of gene expression (Habib N, Li Y, Heidenreich M, Swiech L, Avraham-Davidi I, Trombetta J J, Hession C, Zhang F, Regev A. Div-Seq: Single-nucleus RNA-Seq reveals dynamics of rare adult newborn neurons. Science. 2016 Aug. 26; 353(6302):925-8. doi: 10.1126/science.aad7038. Epub 2016 Jul. 28; Grindberg R V, Yee-Greenbaum J L, McConnell M J, Novotny M, O'Shaughnessy A L, Lambert G M, Arako-Bravo M J, Lee J, Fishman M, Robbins G E, Lin X, Venepally P, Badger J H, Galbraith D W, Gage F H, Lasken R S. RNA-sequencing from single nuclei. Proc Natl Acad Sci USA. 2013 Dec. 3; 110(49):19802-7. doi: 10.1073/pnas.1319700110. Epub 2013 Nov. 18).

The production of nuclei from tissue can be performed using a Dounce homogenizer in the presence of a buffer with a detergent that lyses cells but not nuclei. Nuclei can also be prepared starting from single cell suspensions (CG000124_SamplePrepDemonstratedProtocol_-_Nuclei_RevB, 10× Genomics, https://assets.contentful.com/an68im79xiti/6FhJX6yndYy0OwskGmMc8l/48c341c178-feafa3c e21f5345ed3367b/CG000124_SamplePrepDemonstratedProtocol_-_Nuclei_RevB.pdf) by addition of a lysis buffer such as 10 mM Tris-HCl, 10 mM NaCl, 3 mM MgCl2 and 0.005% Nonidet P40 in nuclease-free water and incubation for 5 min on ice before centrifugation to pellet the nuclei followed by resuspension in a resuspension buffer such as 1×PBS with 1.0% BSA and 0.2 U/μl RNase Inhibitor. The nuclei may be repeatedly pelleted and resuspended to purify them or density gradients or other purification methods used. The titer and viability of the nuclei suspension is usually determined using optical imaging with a microscope and haemocytometer, or an automated instrument with viability determined using Trypan blue or fluorescent dyes.

The multi-process workflow to produce and characterize single-cells and nuclei from tissue is a usually performed manually using several devices without process integration, limiting the scalablity of single cell sequencing and the integration with downstream processes to create a sample-to-answer system. It is laborious and requires skilled technicians or scientists, and results in variability in the quality of the single-cells, and, therefore, in the downstream libraries, analysis, and data. The multiple steps and skill required can lead to differing qualities of single cells or nuclei produced even from the same specimen. Today, the production of high quality single-cells can take months of optimization.

Standarization is necessary before routine single-cell preparation can be performed, particularly in clinical settings. In addition, the length of the process and the process of dissociation can lead to the tissue and cells changing physiology such as altering their expression of RNA and proteins in response to the stresses of the procedure, accentuated by potentially long processing times. A crucial recent insight is that cell processing methods can alter gene expression by placing cells under stress. For example, the use of protease to dissociate cells from tissue, confounding analysis of the true transcriptome (Lacar B, Linker S B, Jaeger B N, Krishnaswami S, Barron J, Kelder M, Parylak S, Paquola A, Venepally P, Novotny M, O'Connor C, Fitzpatrick C, Erwin J, Hsu J Y, Husband D, McConnell M J, Lasken R, Gage F H. Nuclear RNA-seq of single neurons reveals molecular signatures of activation. Nat Commun. 2016 Apr. 19; 7:11022. doi: 10.1038/ncomms11022. PMID: 27090946).

Robust, automated sample preparation is required to simplify workflows before full integration can be achieved with downstream NGS analysis to produce true sample-to-answer systems in the future. Robust processes are required that will input a wide range of tissues from a wide range of organisms and tissues and produce high-quality single-cell or nuclei suspensions without intervention, at acceptable viability for suspensions, with minimal changes to gene expression patterns.

To achieve a standardized process will require a system that automates the sample preparation of cells or nuclei from tissue with a single-use disposable cartridge. In some cases, microvalves can be used in cartridges. Microvalves are comprised of mechanical (thermopneumatic, pneumatic, and shape memory alloy), non-mechanical (hydrogel, sol-gel, paraffin, and ice), and external (modular built-in, pneumatic, and non-pneumatic) microvalves (as described in: C. Zhang, D. Xing, and Y. Li., Micropumps, microvalves, and micromixers within PCR microfluidic chips: Advances and trends. Biotechnology Advances. Volume 25, Issue 5, September-October 2007, Pages 483-514; Diaz-Gonzalez M., C. Fernández-Sánchez, and A. Baldi A. Multiple actuation microvalves in wax microfluidics. Lab Chip. 2016 Oct. 5; 16(20):3969-3976; Kim J., Stockton A M, Jensen E C, Mathies R A. Pneumatically actuated microvalve circuits for programmable automation of chemical and biochemical analysis. Lab Chip. 2016 Mar. 7; 16(5):812-9. doi: 10.1039/c5lc01397f; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605; Lee E, Lee H, Yoo S I, Yoon J. Photothermally triggered fast responding hydrogels incorporating a hydrophobic moiety for light-controlled microvalves. ACS Appl Mater Interfaces. 2014 Oct. 8; 6(19): 16949-55. doi: 10.1021/am504502y. Epub 2014 Sep. 25; Liu X, Li S. An electromagnetic microvalve for pneumatic control of microfluidic systems. J Lab Autom. 2014 October; 19(5):444-53. doi: 10.1177/2211068214531760. Epub 2014 Apr. 17; Desai A V, Tice J D, Apblett C A, Kenis P J. Design considerations for electrostatic microvalves with applications in poly(dimethylsiloxane)-based microfluidics. Lab Chip. 2012 Mar. 21; 12(6):1078-88. doi: 10.1039/c2lc21133e. Epub 2012 Feb. 3; Kim J, Kang M, Jensen E C, Mathies R A Lifting gate polydimethylsiloxane microvalves and pumps for microfluidic control. Anal Chem. 2012 Feb. 21; 84(4):2067-71. doi: 10.1021/ac202934x. Epub 2012 Feb. 1; Lai H, Folch A. Design and dynamic characterization of "single-stroke" peristaltic PDMS micropumps. Lab Chip. 2011 Jan. 21; 11(2):336-42. doi: 10.1039/c0lc00023j. Epub 2010 Oct. 19).

Fluidic connections between cartridges and the instrument fluidics can be achieved by the use of spring-loaded connectors and modular microfluidic connectors as taught by Jovanovich, S. B. et. al. Capillary valve, connector, and router. Feb. 20, 2001. U.S. Pat. No. 6,190,616 and Jovanovich; S. B. et. al. Method of merging chemical reactants in capillary tubes, Apr. 22, 2003, U.S. Pat. No. 6,551,839; and Jovanovich, S., I. Blaga, and R. McIntosh. Integrated system with modular microfluidic components. U.S. Pat. No. 7,244,961. Jul. 17, 2007. which are incorporated by reference and their teachings which describe the modular microfluidic connectors and details of modular microfluidic connectors, including their use as multiway valves, routers, and other functions including microfluidic circuits to perform flowthrough reactions and flow cells with internally reflecting surfaces.

The surface chemistries of the paramagnetic beads and conditions to bind cells or precipitate, wash, and elute nucleic acids and other biomolecules onto surfaces is well understood, (Boom, W. R. et. al. U.S. Pat. No. 5,234,809. Aug. 10, 1993), (Reeve, M. and P. Robinson. U.S. Pat. No. 5,665,554. Sep. 9, 1997), (Hawkins, T. U.S. Pat. No. 5,898,071. Apr. 27, 1999), (McKernan, K. et. al. U.S. Pat. No. 6,534,262. Mar. 18, 2003), (Han, Z. U.S. Pat. No. 8,536,322. Sep. 17, 2013), (Dressman et al., "Transforming single DNA molecules into fluorescent magnetic particles for detection and enumeration of genetic variation" Proc. Natl. Acad. Sci. 100(15):8817-8822 (2003)), (Ghadessy et al., "Directed evolution of polymerase function by compartmentalized self-replication", Proc. Natl. Acad. Sci. 98(8):4552-4557 (2000)), (Tawfik and Griffiths, "Man-made cell-like compartments for molecular evolution" Nat. Biotech. 16(7):652-656 (1998)), (Williams et al., "Amplification of complex gene libraries by emulsion PCR" Nat. Meth. 3(7):545-550 (2006)), and many chemistries are possible and within the scope of the instant disclosure.

BRIEF SUMMARY OF THE INVENTION

Disclosed herein is a Sample Processing System that processes original or processed samples for bioanalysis. The Sample Processing System processes are comprised of enzymatic and mechanical disruption mechanisms with integrated fluidic processes. This invention enables, among other things, the implementation of a Sample Processing System that inputs solid, liquid, or gaseous samples including tissue or other biological samples, and processes the samples for bioanalysis and other analyses.

In some embodiments, the sample or specimen is a tissue specimen. The tissue can be from any source such as a human, animal, or plant tissue. Examples of tissues include, without limitation, a biopsy sample, a cellular conglomerate, an organ fragment, whole blood, bone marrow, a biofilm, a fine needle aspirate, or any other solid, semi-solid, gelatinous, frozen or fixed three dimensional or two dimensional cellular matrix of biological. In another embodiment the released nucleic acid is bound to a membrane, chip surface, bead, surface, flow cell, or particle. The term specimen is used to mean samples and tissue specimens.

In one embodiment the Sample Processing System is used for tissue processing. A Tissue Processing System embodiment can be implemented as a flexible, extensible system that can process solid or liquid tissue and other samples into single cells, nuclei, organelles, and biomolecules with mechanical and enzymatic or chemical processes to produce single cells in suspension, nuclei, subcellular components, and biomolecules such as macromolecules comprised of nucleic acids, comprised of DNA and RNA; proteins; carbohydrates; lipids; biomolecules with multiple types of macromolecules; metabolites; and other biological components, including natural products for bioanalysis. In some embodiments, the Tissue Processing System performs affinity or other purifications to enrich or deplete cell types, organelles such as nuclei, mitochondria, ribosomes, or other organelles, or extracellular fluids. In some embodiments the Tissue Processing System can perform NGS library preparation. In some embodiments, the Tissue Processing System processes tissue into single-cell libraries for sequencing including Sanger, NGS, NNGS and other nucleic acid sequencing technolgies, or protoeomics, or other analytical methods.

Disclosed herein are different embodiments of Sample Processing Systems that integrate two or more of the overall steps to take samples from specimens (i.e., tissue, biofilms, other multi-dimensional matrices with cells or viruses, liquids) and prepare single cell or nuclei in suspensions or on surfaces, or further process the specimens into biomolecules including macromolecules comprised of nucleic acids, comprised of DNA and RNA; proteins; carbohydrates; lipids; biomolecules with multiple types of macromolecules: metabolites; and other biological components, including natural products). In some embodiments specimen can be processed into NGS sequencing libraries, or fully integrated with an analytical system to produce a sample-to-answer systems such as asample-to-answer genomic system.

In some embodiments the Sample Processing System can be integrated with downstream bioanalysis to create a sample-to-answer system. In a preferred embodiment of the Sample Processing System, a Tissue Processing System processing embodiment is integrated with a nucleic acid bioanalysis system to sequence nucleic acids from tissues. Integrated is used to mean the workflows directly interface or in other contexts that the physical system directly interfaces or is incorporated into a system, instrument, or device. In one embodiment, the Tissue Processing System is integrated with a nucleic acid sequencer to produce a sample-to-answer system.

The Sample Processing System can have multiple subsystems and modules that perform processing or analysis. In a preferred embodiment of the Sample Processing System, one or more cartridges performs one or more steps in the processing workflow. In some embodiments the cartridges have multiple processing sites such as processing chambers that can process more than one sample. In some embodiments a cap couples mechanical disruption on the cartridge from a Physical Dissociation Subsystem. In some embodiments reagents from an Enzymatic and Chemical Dissociation Subsystem are delivered to the cartridge by a Fluidic Subsystem to regions that are used as Pre-Processing Chambers and Processing Chambers to disrupt or dissociate specimen and process the cells, subcellular components, and biomolecules for bioanalysis.

The addition of fluids can be controlled by a Fluidic Subsystem with the complete system controlled by software in a Control Subsystem which can include the user interface through a device comprised of monitor, embedded display, touch screen; or through audio commands through the system or an accessory devices such as a cell phone or microphone. In some instances the Control Subsystem can include interfaces to laboratory information management systems, other instruments, databases, analysis software, email, and other applications.

In some embodiments, the amount of dissociation is monitored at intervals during the dissociation and in some instances the viability determined during processing using a Measurement Subsystem. The degree of dissociation and/or viability can be determined inside the main dissociation compartment and/or in a separate compartment or channel, and/or in the external instrument.

In some embodiments, cell imaging solutions, such as cell type specific antibodies, stains, or other reagents, can be added to the tissue or single cells or nuclei for additional processing or imaging. The imaging can capture cells, subcellular structures, or histological or other data. In some embodiments the images can be analyzed to direct the operation and workflow of the Sample Processing System through decisions trees, hash tables, machine learning, or artificial intelligence.

In some embodiments, single cells or nuclei in suspension or on surfaces are further processed using magnetic bead or particle technologies using a Magnetic Processing module to purify or deplete cell types, nuclei, nucleic acids, or other biomolecules.

The term singulated cells is used to mean single cells in suspension or on a surface or in a well including a microwell or nanowell such that they can be processed as single cells. The term singulated cells is also used at times to encompass single nuclei.

In one embodiment, the specimen is added to a cartridge which performs both physical and enzymatic dissociation of the tissue. In some embodiments the Singulator System performs trituration and other physical dissociation modalities as a step or steps in the process of singulating cells. The physical dissociation modalities include passing the specimen through screens, filters, orifices, grinding, blending, sonication, smearing, bead beating, and other methods known to one skilled in the art to physically disrupt tissue to help produce single cells or nuclei or nucleic acids or other biomolecules.

In one embodiment, the Sample Processing System is a Singulator System embodiment. The Singulator System described can input raw, unprocessed samples, or other primary or secondary samples, and output single cells or nuclei ready for single cell or nuclei analysis or for additional processing, e.g., to purify specific cell types with antibodies or by cell sorting or growth, library preparation, or many other applications. A Singulator System embodiment dissociates single cells or nuclei from specimens such as tissue, blood, bodily fluid or other liquids or solids containing cells to produce single cells in suspensions or nuclei, or on surfaces, in matrices, or other output configurations. In a preferred Singulation System described embodiment, there is a cartridge that inputs tissue and/or other specimens and outputs single cells or nuclei, preferably of known titer in a buffer supplemented with media such as Hank's buffer with 2% fetal calf serum.

In some embodiments, the Sample Processing System, such as a Singulator System embodiment, uses enzymes to assist in the process of singulating cells including enzymes to preserve nucleic acids and prevent clumping. The enzymes are comprised of but not limited to collagenases (e.g., collagenases type I, II, III, IV, and others), elastase, trypsin, papain, tyrpLE, hyaluronidase, chymotrypsin, neutral protease, pronase, liberase, clostripain, caseinase, neutral protease (Dispase®), DNAse, protease XIV, RNase inhibitors, or other enzymes, biochemicals, or chemicals such as Triton X-100, Nonidet P40, detergents, surfactants, etc. In other embodiments, different reagents or mixtures of reagents are applied sequentially to dissociate the biological sample or specimen into single-cell suspensions.

In some embodiments the Singulator System produces cell suspensions of known titers and viability. In some embodiments the Singulator System monitors the viability and/or the amount of singulation of a sample and adjusts the treatment time and concentration of enzymes or other dissociation agents by monitoring of the dissociation, for example by the production of single cells or nuclei. The monitoring can be in real time, in intervals, or endpoints or any combinations thereof.

The Singulator System can in some embodiments select from sets of reagents to dissociate tissue and adjust according to production of single cells or viability of cells as monitored by the system, in some instances in real time, at intervals, or as an endpoint. The single-cell suspensions produced by the Singulator System can be used to generate cells with therapeutic application, e.g., re-grow new tissues and/or organs and/or organisms.

The Singulator System has advantages over existing technology and can produce single cells, nuclei, or biomolecules from tissue in an automated and standardized instrument that can in some embodiments process the specimens into NGS libraries or other preparations. The Singulator System will enable users, e.g., researchers, clinicians, forensic scientists, and many disciplines to perform identical processing on biosamples, reducing user variability, and throughput constraints of manual processing.

Embodiments of the Singulation System can prepare single-cells or nuclei or nucleic acids for analysis by methods comprised of DNA sequencing, DNA microarrays, RNA sequencing, mass spectrometry, Raman spectroscopy, electrophysiology, flow cytometry, mass cytometry, and many other analytical methods well known to one skilled in the art including multidimensional analysis (e.g., LC/MS, CE/MS, etc.). In addition, single-cell suspensions or on surfaces or matrices can be used to grow additional cells including genetically altered by methods such as CRISPR, engineered viral or nucleic acid sequences, in tissue culture, or to grow tissues or organs for research and therapeutic purposes.

The Singulator System embodiment described is compatible with commercially available downstream library preparation and analysis by both NGS and NNGS sequencers. The term NGS is used to connote either NGS or NNGS sequencers or sample preparation methods as appropriate. As contemplated herein, next generation sequencing or next-next generation sequencing refers to high-throughput sequencing, such as massively parallel sequencing, (e.g., simultaneously (or in rapid succession) sequencing any of at least 1,000, 100,000, 1 million, 10 million, 100 million, or 1 billion polynucleotide molecules). Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, Genius (GenapSys) or nanopore (e.g., Oxford Nanopore, Roche) platforms and any other sequencing methods known in the art.

In another aspect provided herein is an apparatus, composition of matter, or article of manufacture, and any improvements, enhancements, and modifications thereto, as described in part or in full herein and as shown in any applicable Figures, including one or more features in one or more embodiment.

In another aspect provided herein is an apparatus, composition of matter, or article of manufacture, and any improvements, enhancements, and modifications thereto, as described in part of in full herein and as shown in any applicable Figures, including each and every feature.

In another aspect provided herein is a method or process of operation or production, and any improvements, enhancements, and modifications thereto, as described in part or in full herein and as shown in any applicable Figures, including one or more feature in one or more embodiment.

In another aspect provided herein is a method or process of operation or production, and any improvements, enhancements, and modifications thereto, as described in part or in full herein and as shown in any applicable Figures, including each and every feature.

In another aspect provided herein is a product, composition of matter, or article of manufacture, and any improvements, enhancements, and modifications thereto, produced or resulting from any processes described in full or in part herein and as shown in any applicable Figures.

In one embodiment the single-cell suspension is prepared for a bioanalysis module for downstream analysis including but not limited to sequencing, next generation sequencing, next generation sequencing, proteomic, genomic, gene expression, gene mapping, carbohydrate characterization and profiling, lipid characterization and profiling, flow cytometry, imaging, DNA or RNA microarray analysis, metabolic profiling, functional, or mass spectrometry, or combinations thereof.

In another aspect provided herein is a data analysis system that correlates, analyzes, and visualizes the analytical information of a sample component such as its viability, degree of single cell or nuclei dissociation, with the processing step and measures the change over time, and/or amount of enzymatic activity, and/or physical disruptions of the original biological specimen.

In another aspect provided herein is a data analysis system that correlates, analyzes, and visualizes the analytical information of a sample component such as its viability, degree of single cell or nuclei dissociation, with the processing step and measures the change over time, and/or amount of enzymatic activity, and/or physical disruptions of the original biological specimen and adjusts the processing parameters from the analytical information.

The Singulator System is a novel platform that automates and standardizes the only portion of the single-cell NGS workflow that has not been automated. This will have broad impacts. Process standardization will be critical for comparison of data from lab to lab or research to researcher. The Human Cell Atlas project intends to freely share the multinational results in an open database. However, with no standardization of the complete process, direct comparisons will greatly suffer from widely varying impacts of the first processing step of producing single-cells or nuclei from tissue. Additionally, when single-cell or nuclei sequencing becomes clinically relevant, the standardization and de-skilling of the production of single-cells or nuclei will be required to be performed by an automated instrument such as the Singulator System.

In another aspect, provided herein is a system comprising: (a) an instrument comprising: (i) one or more cartridge interfaces configured to engage a cartridge; (ii) a fluidics module comprising: (1) one or more containers containing one or more liquids and/or gasses; (2) one or more fluid lines connecting the containers with fluid ports in the cartridge interface; and (3) one or more pumps configured to move liquids and/or gasses into and/or out of the fluid port(s); (iii) a mechanical module comprising an actuator; (iv) optionally, a magnetic processing module comprising a source of magnetic force, wherein the magnetic force is positioned to form a magnetic field in the processing chamber; (v) optionally, a measurement module; (vi) optionally, a control module comprising a processor and memory, wherein the memory comprises code that, when executed by the processor, operates the system; and (b) one or more cartridges, each engaged with one of the cartridge interfaces, wherein each cartridge comprises: (i) a sample inlet port; (ii) one or more cartridge ports communicating with the fluid ports in the cartridge interface; (iii) a preprocessing chamber communicating with the sample inlet port and with at least one cartridge port, and comprising a tissue disruptor configured for mechanical disruption of tissue, wherein the tissue disruptor engages with and is actuated by the actuator when the cartridge is engaged with the cartridge interface; (iv) a strain chamber communicating with the preprocessing chamber configured to separate cells and/or nuclei from disrupted tissue; (v) a processing chamber communicating with the strain chamber, optionally communicating with one or more cartridge ports and configured to perform one or more processing steps on separated cells and/or nuclei; and (vi) optionally, one or more waste chambers fluidically connected with the processing chamber. In one embodiment the tissue disruptor comprises a grinder, a pestle or a variable orifice. In another embodiment the system further comprises a barcode reader. In another embodiment the system comprises a measurement module (v) that performs optical imaging to measure titer, clumping, and/or viability of cells or nuclei or properties of biomolecules. In another embodiment the system comprises a measurement module (v) and a control system (vi), wherein the measurement module measures, and one or more time points, characteristics of a sample in the processing chamber, and control system comprises code that determines a state of the sample, e.g., viability or degree of single cell or nuclei dissociation, and that adjusts processing parameters. In another embodiment the system further comprises (c) an analysis module, wherein an input port of the analysis module is in fluid communication with the processing chamber. In another embodiment the analysis module performs an analysis selected from one or more of: DNA sequencing, next generation DNA sequencing, next generation DNA sequencing, proteomic analysis, genomic analysis, gene expression analysis, gene mapping, carbohydrate characterization and profiling, lipid characterization and profiling, flow cytometry, imaging, DNA or RNA microarray analysis, metabolic profiling, functional analysis, and mass spectrometry. In another embodiment the cartridge interface comprises a means of positioning the cartridge in the instrument that engages the fluidic module and the mechanical module and optionally is temperature controlled. In another embodiment the cartridge is disposable.

In another aspect provided herein is a method comprising: (a) providing a tissue sample to a preprocessing chamber; (b) automatically performing mechanical and enzymatic/chemical disruption of the tissue in the preprocessing chamber to produce disrupted tissue comprising released cells and/or nuclei and debris; (c) automatically moving the disrupted tissue into a strain chamber comprising a strainer and/or filter and separating the released cells and/or nuclei from the debris therein; and (d) automatically moving the released cells and/or nuclei into a processing chamber. In another embodiment (d) further comprises performing at least one processing step on the released cells and/or nuclei in the processing chamber. In another embodiment processing comprises one or more automatically performed processes selected from: (I) lysing cells; (II) capturing cells; (Ill) isolating nucleic acid; (IV) isolating protein; (V) converting RNA into cDNA; (VI) preparing one or more libraries of adapter tagged nucleic acids; (VII) performing PCR; (VIII) isolating individual cells or individual nuclei in nanodrops or nanoboluses; and (IX) outputting released cells and/or nuclei into output vessels such as 8 well strip tubes, microtiter plates, Eppendorf tubes, a chamber in the cartridge, or other vessels capable of receiving cell suspensions. In another embodiment the method further comprises: (e) automatically capturing the released cells and/or nuclei in the processing chamber by binding to magnetically attractable particles comprising moieties having affinity for the cells and/or nuclei and applying a magnetic force to the processing chamber to immobilize the captured cells and/or nuclei. In another embodiment the method further comprises: (e) automatically monitoring cell and/or nuclei titer in the processing chamber and, when the titer reaches a desired level, exchanging a dissociation solution used to dissociate the tissue for a buffer.

In another aspect provided herein is a cartridge comprising: (i) a sample inlet port; (ii) one or more cartridge ports configured to communicate with fluid ports in a cartridge interface; (iii) a preprocessing chamber communicating with the sample inlet port and with at least one cartridge port, and comprising a tissue disruptor configured for mechanical disruption of tissue, wherein the tissue disruptor engages with and is actuated by the actuator when the cartridge is engaged with the cartridge interface; (iv) a strain chamber communicating with the preprocessing chamber configured to separate cells from disrupted tissue; (v) a processing chamber communicating with the strain chamber, optionally communicating with one or more cartridge ports and configured to perform one or more processing steps on separated cells; and (vi) optionally, one or more waste chambers fluidically connected with the processing chamber. In another embodiment the cartridge further comprises a cap that opens and closes the sample inlet port. In another embodiment the cap comprises a tissue disruptor element that moves about rotationally and back and forth along an axis. In another embodiment the cartridge further comprises a holder. In another embodiment the cartridge further comprises a top piece and a bottom piece connected by collapsible element which allow the top piece and/or the bottom piece to move relative to the holder. In another embodiment the holder comprises a mesh screen. In another embodiment the cartridge further comprises a grinding element for grinding tissue in the preprocessing chamber. In another embodiment the cartridge further comprises a barcode comprising information about the cartridge and/or its use. In another embodiment the cartridge further comprises a plunger configured to move slideably within the preprocessing chamber.

In another aspect provided herein is a variable orifice device for disrupting tissue comprising: (a) a first container and a second container fluidically connected through a flexible tube comprising a lumen; (b) an adjustable clamp positioned to clamp the flexible tube, wherein adjusting the clamp alters the cross-sectional area of the lumen; and (c) one or more pumps or devices operatively coupled with the first and/or second containers configured to push liquid in one container through the flexible tubing into the other container. In another embodiment the adjustable clamp comprises an eccentric cam operatively coupled to a motor, wherein rotating the cam closes or opens the clamp.

In another aspect provided herein is a method for disrupting tissue comprising: (a) providing a variable orifice device comprising first container and a second container fluidically connected through a flexible tube comprising a lumen; (b) moving a sample comprising tissue from one of the containers through the flexible tube to another one of the containers; (c) decreasing the cross-sectional area of the lumen and moving the sample from one of the containers through the flexible tube to another one of the containers; (d) repeating step (c) one or more times to disrupt the tissue.

In another aspect provided herein is a method of determining an amount of amplification of a nucleic acid molecule comprising amplifying the nucleic acid molecule with primers comprising random barcode (e.g., a barcode wherein each round of amplification adds in additional barcode to an amplified nucleic acid molecule); and after amplification, counting incorporated barcodes, wherein the number of incorporated barcodes indicates the amount of amplification.

BRIEF DESCRIPTION OF THE DRAWINGS

The skilled artisan will understand that the drawings, described below, are for illustration purposes only. The drawings are not intended to limit the scope of the present teachings in any way.

FIG. 11 is an example of part of a cartridge designed to physically disrupt a specimen with a rotating plunger.

FIGS. 12A-C illustrates a rotating disruptor with staggered grinding features on a rotor and stator.

FIGS. 15A-D show designs of rotating disruptors with different pitches of spiral external features.

FIGS. 16A-E shows an example of a rotating disruptor with external spiral features and an example of a rotating disruptor with both internal and external spiral features.

FIGS. 17A-D illustrates a rotating disruptor assembly with a mesh top surface to grind the specimen and an internal spiral to circulate fluids.

FIG. 18 shows a three chamber cartridge with cap containing a plunger with two PreProcessing chambers and one Processing chamber for a variable orifice implementation.

FIG. 24A-B shows the titer and viability of processing a range of sizes of mouse tissues into single cells using the AutoSingulator instrument with a cartridge.

DETAILED DESCRIPTION OF THE INVENTION

Figure 1:
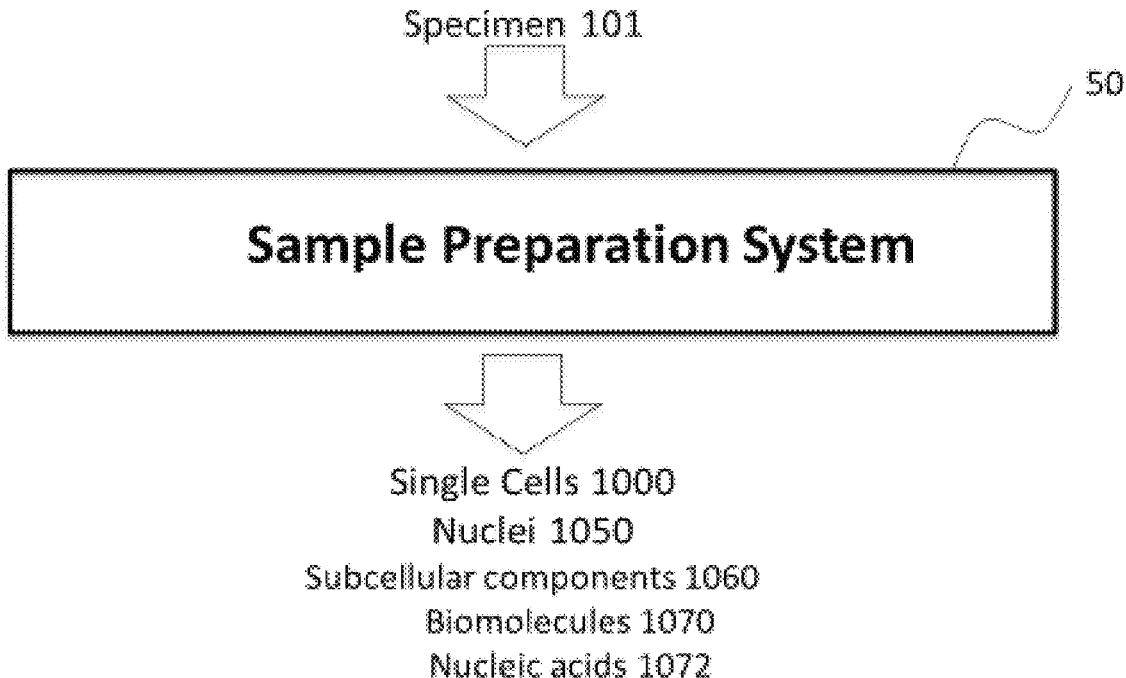
FIG. 1 shows a Sample Processing System that processes specimens or tissue specimens into biocomponents such as single cells or nuclei for bioanalysis.

NGS, mass spectrometry, FACS, and other modern high-throughput analysis systems have revolutionized life and medical sciences. The progression of information has been from the gross level of organism, to tissue, and now to single cell analysis. Single cell analysis of genomic, proteomic including protein expression, carbohydrate, lipid, and metabolism of individual cells is providing fundamental scientific knowledge and revolutionizing research and clinical capabilities.

All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). Both plural and singular means may be included.

Specimen: The term "specimen," as used herein, refers to an in vitro cell, cell culture, virus, bacterial cell, fungal cell, plant cell, bodily sample, or tissue sample that contains genetic material. In certain embodiments, the genetic material of the specimen comprises RNA. In other embodiments, the genetic material of the specimen is DNA, or both RNA and DNA. In certain embodiments the genetic material is modified. In certain embodiments, a tissue specimen includes a cell isolated from a subject. A subject includes any organism from which a specimen can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue specimen is a human tissue sample. The tissue specimen can be liquid, for example, a blood sample, red blood cells, white blood cells, platelets, plasma, serum. The specimen, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue specimen is a solid tissue sample or a frozen tissue sample or a biopsy sample such as a fine needle aspirate or a core biopsy or a resection or other clinical or veterinary specimen. In still further aspects, the specimen comprises a virus, bacteria, or fungus. The specimen can be an ex vivo tissue or sample or a specimen obtained by laser capture microdissection. The specimen can be a fixed specimen, including as set forth by U.S. Published Patent Application No. 2003/0170617 filed Jan. 28, 2003.

In some embodiments, the single cells can be analyzed further for biomolecules including one or more polynucleotides or polypeptides or other macromolecules. In some embodiments, the polynucleotides can include a single-stranded or double-stranded polynucleotide. In some embodiments, the polypeptide can include an enzyme, antigen, hormone or antibody. In some embodiments, the one or more biomolecules can include RNA, mRNA, cDNA, DNA, genomic DNA, microRNA, long noncoding RNA, ribosomal RNA, transfer RNA, chloroplast DNA, mitochondrial DNA, or other nucleic acids including modified nucleic acids and complexes of nucleic acids with proteins or other macromolecules.

It will be readily apparent to one of ordinary skill in the art that the embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

FIG. 1 shows a Sample Processing System 50 that can input specimen 101 and process them to produce biologicals such as single cells 1000 or nuclei 1050, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071: metabolites 1078; and other biological components, including natural products 1079 for bioanalysis.

Figure 2:
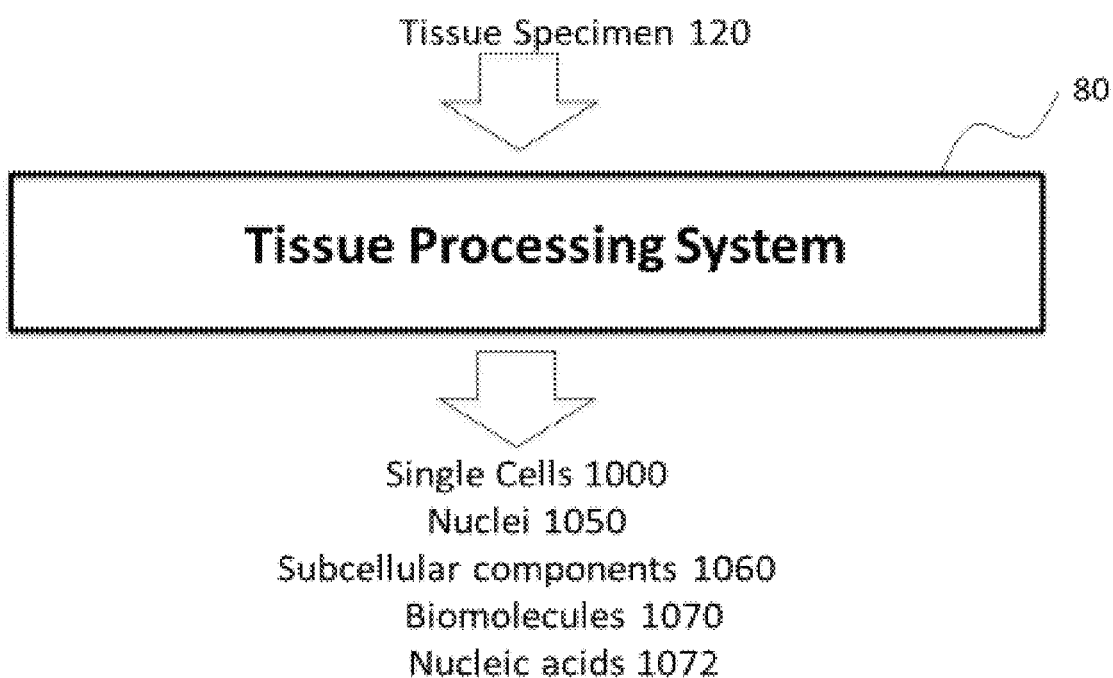
FIG. 2 shows a Tissue Processing System that processes tissue specimens into biocomponents such as single cells or nuclei or other for bioanalysis.

FIG. 2 shows a Tissue Processing System 80 that can input tissue specimens 120 and other specimens 101 and process them to produce biologicals such as single cells 1000 or nuclei 1050, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071; metabolites 1078; and other biological components, including natural products 1079 for bioanalysis.

Figure 3:
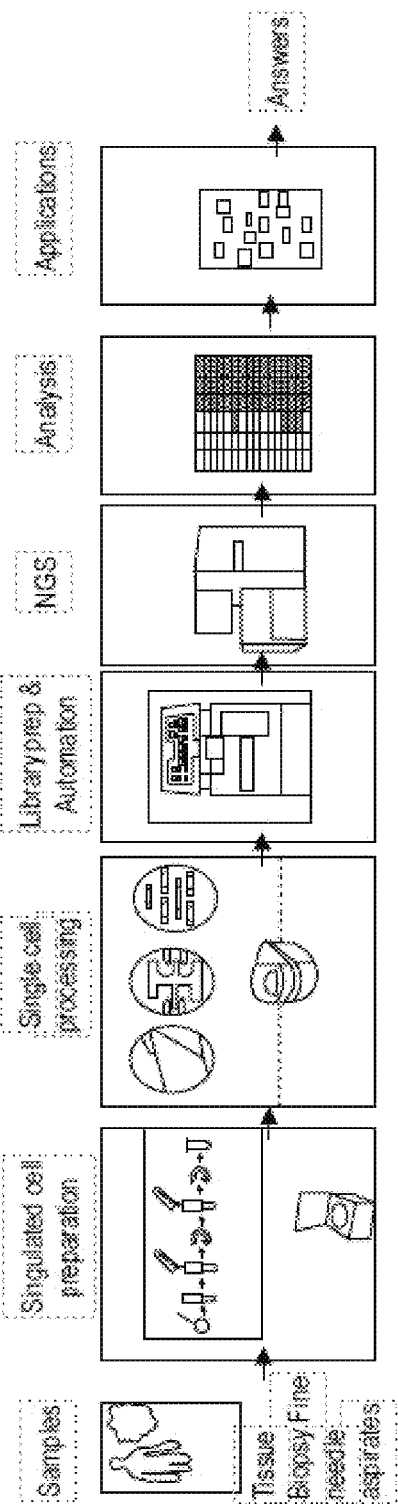
FIG. 3 shows an example of the workflow to prepare and analyze single cells or nuclei for NGS analysis. Tissue samples are dissociated into singulated cells before processing into typically single-cell cDNA when samples can be pooled for library preparation, sequencing, and analysis. Different embodiments of the implementation can integrate different segments of the workflow.

FIG. 3 shows the overall workflow for single-cell NGS sequencing from tissue through singulated cell preparation of single-cell suspensions to processing of the single-cells into cDNAs typically to library preparation, NGS sequencing, analysis, and applications. The first step is forming singulated cells in a suspension. In the workflow shown, this consists of mincing tissue, digesting extracellular matrix, filtering through a 70 □m filter, pelleting the cells, lysis of red blood cells with Ammonium-Chloride-Potassium (ACK) buffer, pelleting of the cells, and cryopreservation in fetal bovine serum with 10% DMSO. After the generation of droplets or capture of cells, the single-cell workflow shown in FIG. 3 is well integrated using the installed ultrahigh throughput, low cost, NGS infrastructure. The downstream sequencing process, sequence readout, and analysis has great capacity at a low cost. However, the upstream production of single cells 1000 or nuclei 1050 suspensions is not integrated and relies on manual processing of specimens 101.

Figure 4:
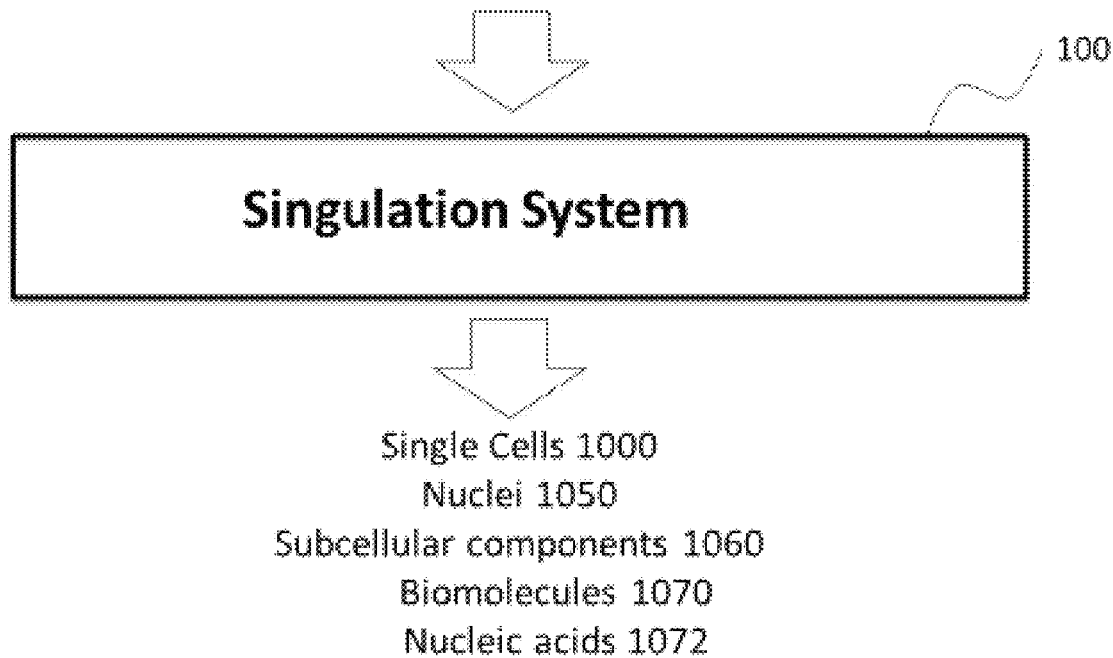
FIG. 4 shows a high level overview of the workflow for a Singulator System to generate for example single cell or nuclei or biomolecules from a specimen or tissue specimen.

Referring to FIG. 4, the Singulation System 100 accepts one or more specimens 101 or tissue specimens 120 and processes them to produce biologicals such as single cells 1000 or nuclei 1050, or other biocomponents comprised of subcellular components 1060, and biomolecules 1070 such as macromolecules 1071 and nucleic acids 1072, comprised of DNA 1073 and RNA 1074 and single cell libraries 1200 for bioanalysis.

Figure 5:
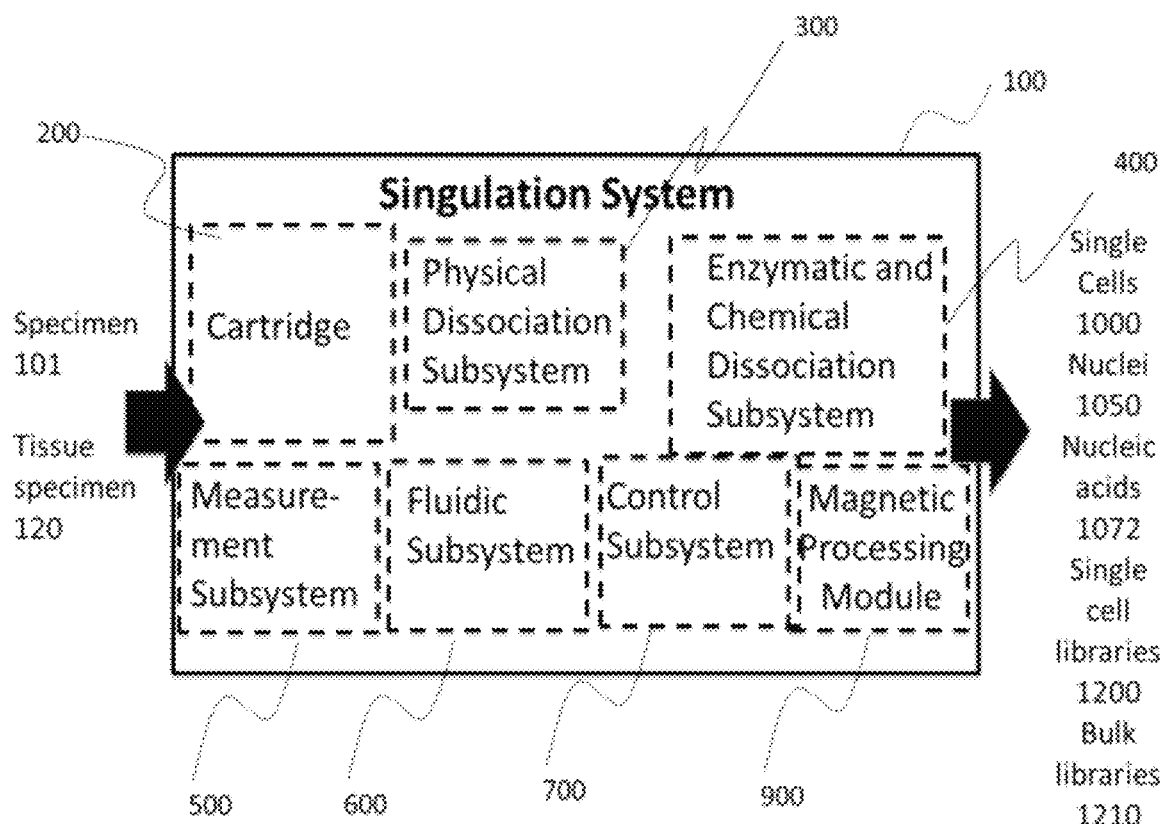
FIG. 5 shows an overview Singulator System and some exemplary modules. Tissue specimens or other specimens processed into single cells, nuclei, nucleic acids, single-cell libraries and other biologicals through the use of one or more cartridges and one or more of the Physical Dissociation Subsystem, the Enzymatic and Chemical Dissociation Subsystem, the Measurement Subsystem, the Fluidic Subsystem, the Control Subsystem, and a Magnetic Module.

Referring to FIG. 5, in many embodiments, the Singulation System 100 processing is performed in cartridges 200 in the system. Tissue specimens 120 or other specimens 101 are converted to single cells 1000 or nuclei 150 through the use of cartridge 200 with one or more of the Physical Dissociation Subsystem 300, the Enzymatic and Chemical Dissociation Subsystem 400, the Measurement Subsystem 500, the Fluidic Subsystem 600, the Control Subsystem 700, and the Magnetic Module 900.

The Physical Dissociation Subsystem 300 can perform physical disruption by passing the specimen through orifices, grinding, rotating a rotor with features to dissociate tissue, forcing tissue through screens or mesh, sonication, blending, homogenization, bead beating, and other methods known to one skilled in the art to physically disrupt tissue to help produce single cells.

The Enzymatic and Chemical Dissociation Subsystem 400 can perform enzymatic disruption by adding formulations of a reagents or mixture of components comprised of but not limited to collagenases (e.g., collagenases type I, II, III, IV, and others), elastase, trypsin, papain, hyaluronidase, chymotrypsin, neutral protease, clostripain, caseinase, neutral protease (Dispase®), DNAse, protease XIV, RNase inhibitors, or other enzymes, biochemicals, or chemicals such as EDTA, protease inhibitors, buffers, acids, or base.

Another aspect or the Enzymatic and Chemical Dissociation Subsystem 400 can perform chemical disruption or chemical and enzymatic disruption is by adding formulations of a chemicals that might disrupt tissue or cellular integrity such as Triton X-100, Tween, Nonident P40, other surfactants, or chemicals that can dissociate tissue into cells or produce nuclei or other organelles.

In other embodiments, different reagents or mixtures of reagents are applied sequentially to dissociate the biological sample or specimen into single cells. The physical and enzymatic/chemical dissociation systems can be separate from each other, or they can be co-located (e.g., acting upon the sample simultaneously or sequentially).

In some embodiments, the amount of dissociation is monitored at intervals during the dissociation or at the endpoint, and in some instances the viability is determined during processing using a Measurement Subsystem 500. The Measurement Subsystem 500 can be an optical imaging device to image cells using brightfield, phase contrast, fluorescence, chemiluminescence, near-field, or other optical readouts, or an electrical measurement, such as an impedance measurement of the change in conductivity, when a cell passes through a sensor, or other types of measurement.

The addition and movement of fluids can be performed by a Fluidic Subsystem 600. The Fluidic Subsystem 600 can use syringe pumps, piezopumps, on-cartridge pumps and valves, pressure, pneumatics, or other components well known to one skilled in the art.

The Singulation System 100 can be controlled by software in a Control Subsystem 700 which can be comprised of a user interface 740 through a monitor, embedded display, or a touch screen 730. In some instances the Control Subsystem 700 can include interfaces to laboratory information management systems, other instruments, analysis software, display software, databases, email, and other applications. The Control Subsystem 700 can include control software 725 and scripts that control the operation and in some embodiments the scripts can be revised, created, or edited by the operator.

In another aspect provided herein is a device for the dissociation of a biological sample, the device comprising: (i) a biological sample or specimen 101; (ii) a cartridge 200 capable of dissociating tissue; (iii) an instrument to operate the cartridge 200 and provide fluids as needed (iv) a measurement module 500 such as an optical imaging to measure titer, clumping, and/or viability, (v) exchange of dissociation solution for buffer or growth media at the desired titer, and (vi) output vessels such as a chamber in the cartridge, 8 well strip tubes, microtiter plates, Eppendorf tubes or other vessels capable of receiving cell suspensions.

In another aspect provided herein is a device for the dissociation of a biological sample and the production of single-cell 1000 or nuclei 1050 suspensions or matched bulk nucleic acids 1010 or single cell libraries 1200 or matched bulk libraries 1210, the device comprising: (i) a chamber or area to input a biological sample or specimen; (ii) a cartridge capable of dissociating tissue or specimen; (iii) an instrument to operate the cartridge and provide fluids as needed (iv) a measurement module such as an optical imaging to measure titer, clumping, and/or viability, (v) exchange of dissociation solution for buffer or growth media at the desired titer, (vi) the production of single-cell 1000 or nuclei 1050 suspensions or single cell libraries 1200, and matched bulk nucleic acid libraries 1210, in output vessels such as 8 well strip tubes, microtiter plates, Eppendorf tubes, a chamber in the cartridge, or other vessels capable of receiving cell suspensions.

Referring to FIG. 5, a Magnetic Processing module 900 can use magnetic processing of magnetic and paramagnetic particles or beads, referred to as beads, to separate single cells 1000, or cell types or nuclei 1050, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071, metabolites 1078; and other biological components, including natural products 1079 for bioanalysis. In some embodiments the beads have a surface chemistry that facilitates the purification of the biologicals in conjunction with the chemical conditions. In other embodiments the bead have affinity molecules comprised of antibodies, aptamers, biomolecules, etc. that specifically purify certain biologicals such as cell types, nucleic acids, nuclei 1050, or other components of tissue or samples.

In another aspect provided herein is a device for the dissociation and single-cell library preparation of a biological sample, the device comprising: (i) a chamber or area to input a biological sample or specimen; (ii) a cartridge 200 capable of dissociating tissue specimens 120 into single-cells 1000 and then produce single-cell libraries 1200; (iii) an instrument to operate the cartridge 200 and provide fluids as needed (iv) a measurement subsystem 500 such as an optical imaging to measure titer, clumping, and/or viability, (v) exchange of dissociation solution for buffer at the desired titer, (vi) a magnetic processing or other processing chamber or tubing to perform magnetic separations, normalizations, purifications, and other magnetic processes, for example, to purify nucleic acids, couple enzymatic reactions such as library preparation reactions, and other processes including producing single-cells or nuclei in isolation, such as nano-drops, nanoboluses, or physical separation, (vii) output vessels such as 8 well strip tubes, microtiter plates, Eppendorf tubes, a chamber in the cartridge, or other vessels capable of receiving cell suspensions.

The basic elements of the Singulation System 100 can be configured in multiple ways depending on the specimen(s) 101 and analytes to be analyzed. In the following examples, a few of the numerous configurations are described in detail but in no way is the invention limited to these configurations as will be obvious to one skilled in the art. The Singulation System 100 can accommodate many different types of specimens 101, comprised of fresh tissue; snap-frozen tissue; microtome slices (cryo, laser or vibrating) of tissue; fixed tissue; bulk material obtained by surgical excision, biopsies, fine needle aspirates; samples from surfaces, and other matrices.

There is a need to fill gap in the single-cell and nuclei NGS sample preparation pipeline by starting the workflow at processing raw solid tissues or liquids into single-cell 1000 and nuclei 1050 suspensions. The instant disclosure teaches how to produce a system that processes tissue specimens 120 and other samples into single-cells 1000 or nuclei 1050, and other samples types then extend the processing all the way to libraries, such as single cell libraries 1200, with little or no intervention by the operator once the process is started. This requires adapting to the widely varying starting types of tissue, with different requirements depending on the tissue, species, age, and state.

In the instant invention, many embodiments are possible. Systems with increasing capabilities can be developed as a series of embodiments, five are described: two embodiment as a Single Sample Singulator System 2000, a Four Sample Singulator System 2400, an Enhanced Singulator System 2500, and the Single Librarian 3000 embodiments.

Two embodiments of a Single Sample Singulator System 2000 embodiment are described to process tissue into single-cell suspensions and purified single-cell subtypes or nuclei for many tissues. A Four Sample Singulator System 2400 is described to process four specimens 101 into single-cell 1000 or nuclei 1050 suspensions. An Enhanced Singulator System 2500 is described with additional capabilities to titer, adjust the buffer, and purify or deplete cell types, nuclei, organelles, or biomolecules. A Single Librarian 3000 embodiment is described that integration with single-cell library preparation, and bulk nucleic acid and library preparation and adds QC capabilities. It will be obvious to one skilled in the art that the systems can continue to be expanded with additional capabilities or be configured in many other embodiments.

This disclosure describes how to automate, integrate, and importantly standardize the complete process for single-cell 1000 or nuclei 1050 suspensions in a single Singulator System 100 system embodiment. The Singulator System 100 will greatly enable basic researchers, students, and translational researchers as well as clinicians and others with its ease of use and high performance. Designed for genomics and easily adaptable to other applications, the Singulator System 100 performs the most upstream sample preparation steps—from tissue specimens 120 or other sample types—and standardize the complete sample preparation process for single-cell 1000 and nuclei 1050 suspensions.

Single-Use Cartridge Designs.

Cartridges 200 can be used to process tissue into single-cell 1000 suspensions or nuclei 1050 and are preferrably single-use. The major workflow steps to produce single-cell suspensions 1000 are mechanical disruption of tissue, enzymatic dissociation, and straining to remove clumps, and optional cell type isolation by magnetic bead capture.

Ideally, the cartridge 200 will input specimen 101 and output viable singulated cells 1000 or nuclei 1050 in suspension and can be designed to incorporate magnetic and other downstream processing to also allow production of biomolecules 1070 such as nucleic acids 1072. It is desirable that disposable cartridge 200 process multiple types of samples with mechanical disruption and enzymatic or chemical dissociation according to the tissue type and condition. The cartridge 200 can be designed to process tissue as quickly and as gently as possible, not expose the operator to the tissue being processed, and be manufacturable at low cost. Multiple mechanical methods may be needed to accommodate the wide range of tissues and their individual requirements: designs are shown that can be readily adapted to multiple different mechanical disruption methods comprising variable orifice 490, grinding with rotating plungers 336, pestles 361, and straining and filtering using a plunger 362 as well as other mechanical methods without limitation.

Cartridges 200 can be designed for 3D printing, injection molding in plastics with single or double pulls and low labor assembly, or layered assembly of fluidic and other layers, combinations of methods, and other methods well known to one skilled in the art. Fluids can be delivered to cartridge 200 by a syringe pump 2130 or can be preloaded onto cartridge 200 or many combinations. In some embodiments, flexible tubing 493 can connect chambers and creates simple pinch valves 491 to direct flow. In other embodiments, channels are created in the cartridge 200 and valves can be incorporated such as pneumatic valves, or other valves.

Example: Cartridge with Collapsible Features

In a preferred embodiment, referring to FIG. 6, cartridge 200 performs both a physical and enzymatic dissociation of the tissue. In this example, as shown in FIG. 6A the cartridge has a cap 210 which can be opened and closed, and a holder 235 for the operator to handle. This embodiment has collapsible features 215 which allow top piece 241 and bottom piece 242 to move relative to the holder 235. Other embodiments might use a plunger or have fixed walls. The holder 235 can have a mesh screen 225 and grinding features 220 which can be located on the cap 210 and the holder 235. The grinding features 220 can be solid or allow fluids to pass through. A barcode 240 on holder 235 encodes tracking information of the cartridge 200 and usage. Fluidic connections 230 engage with the instrument to allow the Fluidic Subsystem 600 to add or remove liquids from the cartridge 200. The Singulation System 100 can have pushbutton operation for either specialists or non-specialists to generate single-cell suspensions 1000 or other nuclei 1050 or other outputs from specimens 101 for medical, health, life science research, and other applications.

Figure 6A:
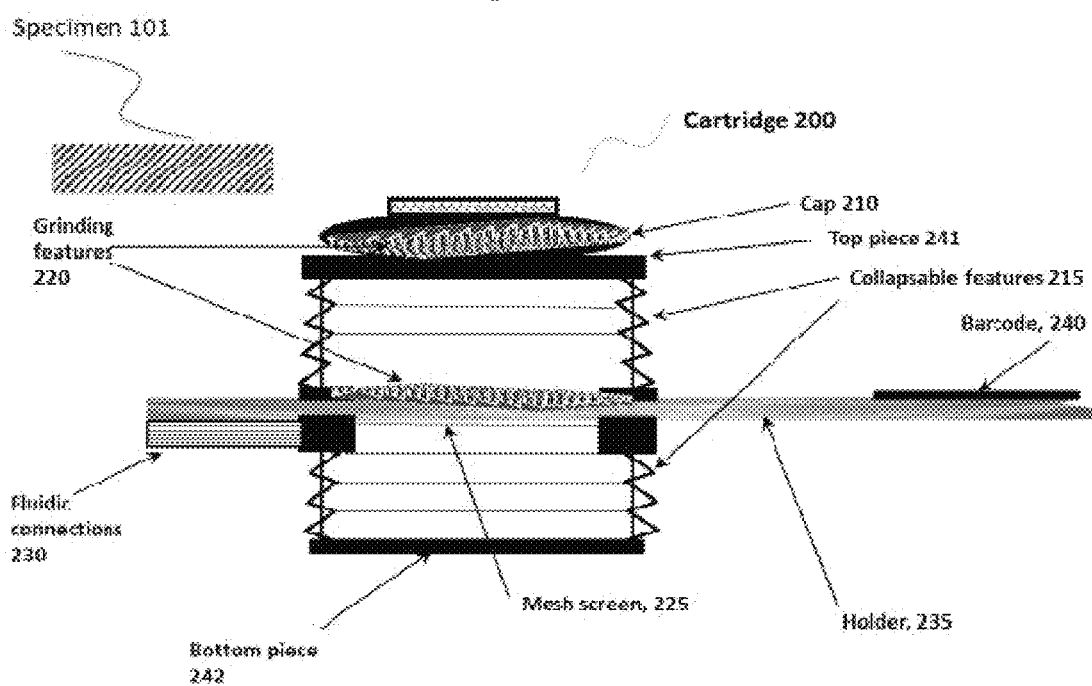
FIGS. 6A-K shows an example of a process with a cartridge that processes specimens into single cells, nuclei, or other biocomponents.
Figure 6B:
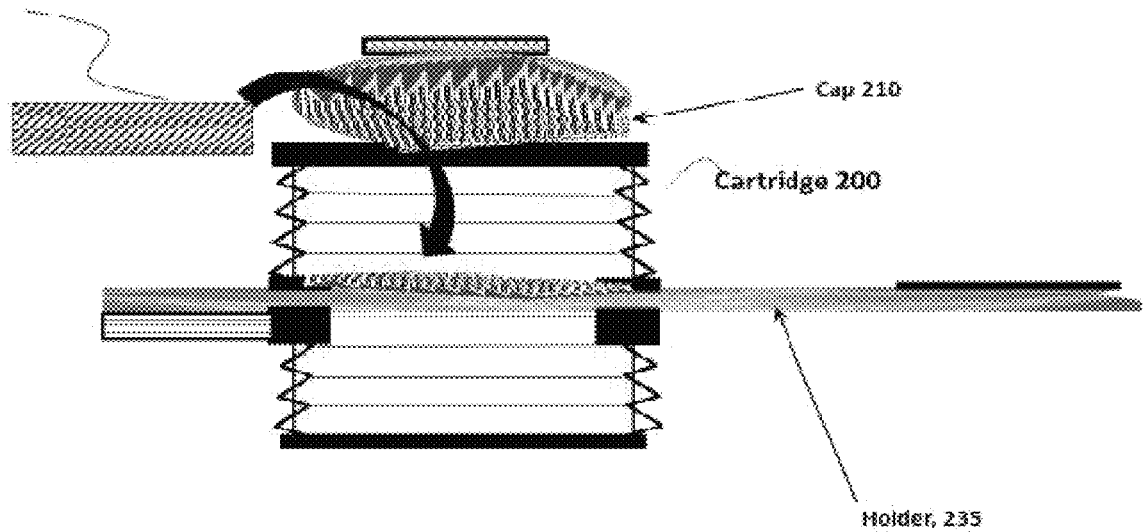
Figure 6C:
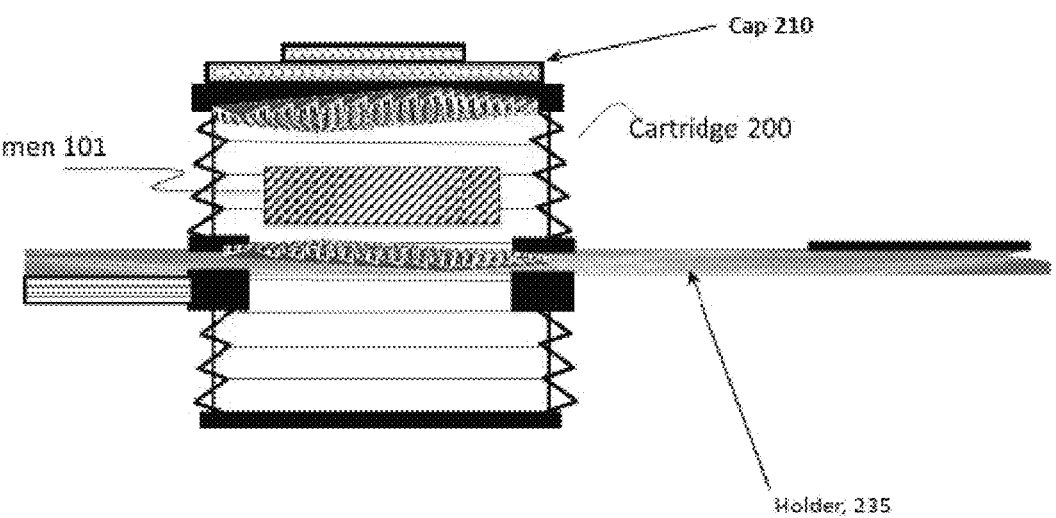

Referring to FIG. 6B, cartridge 200 has a cap 210 which can be opened in a top piece 241 to allow the specimen 101 to be added into cartridge 200 while securing cartridge 200 by gripping holder 235. Referring to FIG. 6C, once the specimen 100 is placed in the cartridge, the cap 210 can be closed or placed on the cartridge to isolate the specimen 101 in cartridge 200 for processing.

In some embodiments the fluidics of the Singulation System 100 are incorporated onto cartridge(s) 200. In some embodiments of the Singulation System 100, the valves for the subsystems are microvalves, which in some embodiments are created in microchips with microchannels. Microvalves are well know to those skilled in the art. Microvalves can be actuated by, for example, mechanical force, pneumatic pressure, electrostatic force, piezoelectric force, thermal expansion force, etc. They may be have internal or external actuators. Pneumatic valves include, for example, diaphragm valves that employ a flexible membrane of the pneumatic pressure or vacuum to close or open a fluid channel. Electrostatic valves may include, for example, a polysilicon membrane or a polyimide cantilever that is operable to cover a hole formed in a substrate. Piezoelectric valves may include external (or internal) piezoelectric disks that expand against a valve actuator. Thermal expansion valves may include a sealed pressure chamber bounded by a diaphragm. Heating the chamber causes the diaphragm to expand against a valve seat.

In some embodiments, cartridges 200 are used with functionality from a group of reagents, valves or microvalves, microchannels, syringe pumps, optical devices, integrated electronics for control of cartridge 200 functions, and lot tracking. In some embodiments microchips are used as parts of instrument or cartridges 200. The cartridges 200 in some embodiments hold kits to perform the chemistries including all needed reagents, stains, library preparation chemistry, and other consumables. In other embodiments, the reagents or parts of the reagents are on board the instrument or added manually by the user. In some embodiments the reagents are stabilized for long term room temperature storage by freeze drying or the addition of osmoprotectants.

Figure 6D:
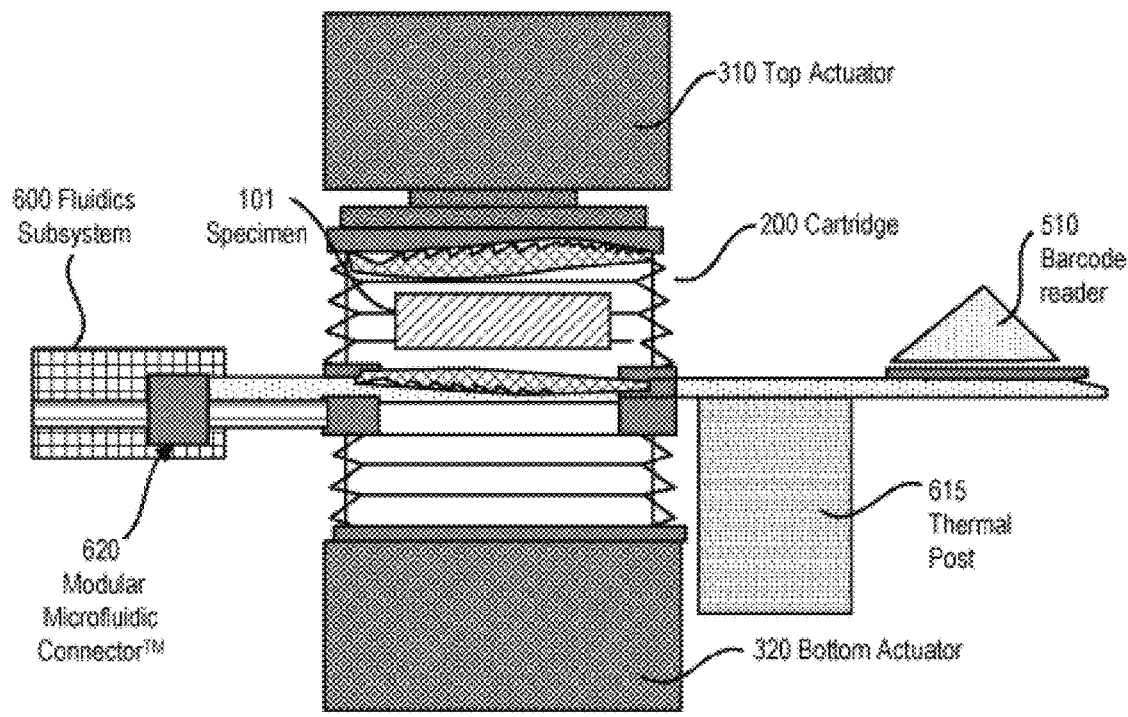

Referring to FIG. 6D, in a preferred embodiment, after specimen 101 has been added and the cap closed, cartridge 200 is placed into the Singulation System 100 which engages cartridge 200. The Physical Dissociation Subsystem 300 engages a top actuator 310 and a bottom actuator 320 with the top piece 241 and bottom piece 242 respectively. The actuators can move up and down (Z direction) and in some embodiments either rotate or move horizontally in the X and Y directions. A thermal post 615 can engage the holder 235 to control the temperature of the cartridge or in other implementations the cartridge is held in a chamber with temperature control or in other embodiments the temperature is not controlled. In some embodiments, a thermal cycling temperature device may be incorporated. In others embodiments, a Peltier may control the temperature of one or more chambers including lowering the temperature. In some embodiments, a barcode reader 510 interrogates barcode 240 to track cartridge 200 used for specimen 101.

The Fluidic Subsystem 600 engages with a modular microfluidic connector 620 located on the holder. The modular microfluidic connector 620 are true zero dead volume connectors and can join two or more capillaries to one, or join microchannels to microchips or cartridges, and be used as multiway microvalves. The modular microfluidic connectors 620 can have a linear array of microchannels, such as four, on both sides of the connection. The relative position of one side of the connection can be moved to line up different sets of microchannels or close off a microchannel as taught in U.S. Pat. No. 7,244,961. In the embodiment taught in this disclosure, the modular microfluidic connectors are used to open and close fluidics to cartridge 200 to take aliquots for measurement, change media, and output the single cells.

Figure 6E:
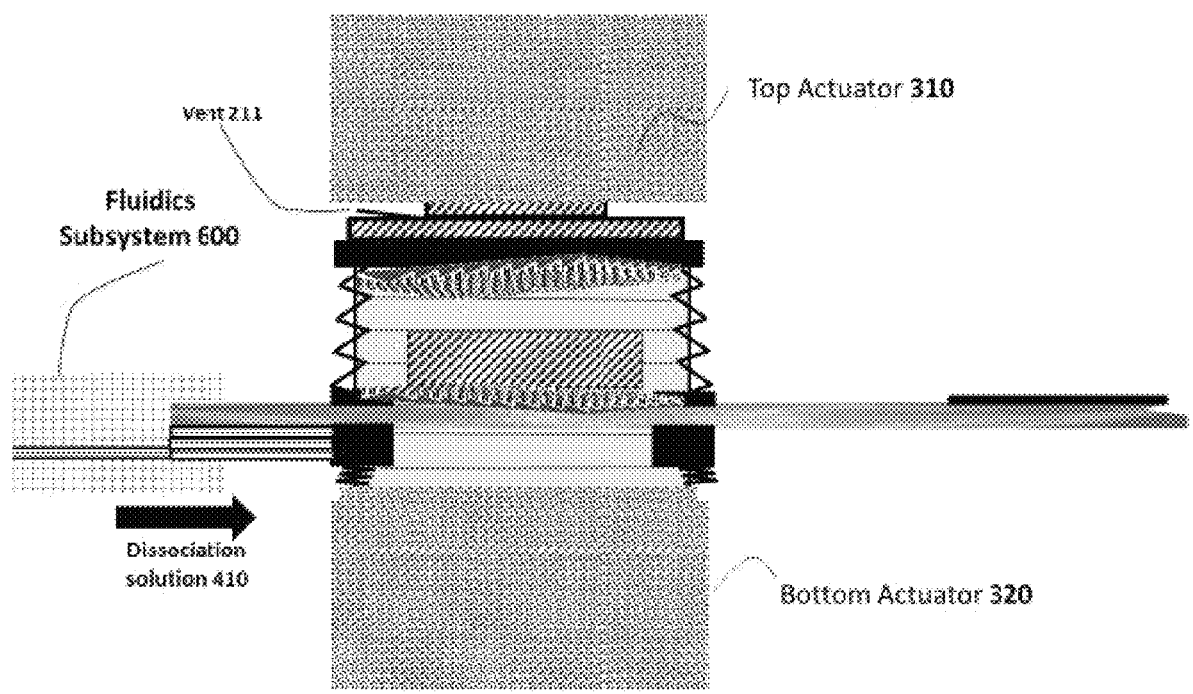

Referring to FIG. 6E, in one embodiment, the bottom actuator 320 is moved up towards the holder 235 and an enzymatic or chemical dissolution solution 410 can be added into the cartridge 200 through modular microfluidic connection 230 from Fluidic Subsystem 600. The dissociation solution can be commercially available, such as Liberase™ DH Research Grade Roche or equivalent products, or be custom formulations to dissociate intercellular adhesion between cells and free the cells from the extracellular matrix. The dissociation solutions to dissociate the tissue and prevent clumping of single cells 1000 or nuclei 1050 can be comprised of collagenases (e.g., collagenases type I, II, III, IV, and others), elastase, trypsin, papain, hyaluronidase, chymotrypsin, neutral protease, clostripain, caseinase, neutral protease (Dispase®), DNAse, protease XIV or other enzymes. The amount and concentration of the dissociation solution, time of contact, temperature, and other parameters can be optimized for particular tissue, organism, state of tissue, and age. As the dissociation solution is added, air can be released through vent 211 which can be an air-permeable, liquid-impermeable membrane.

Figure 6F:
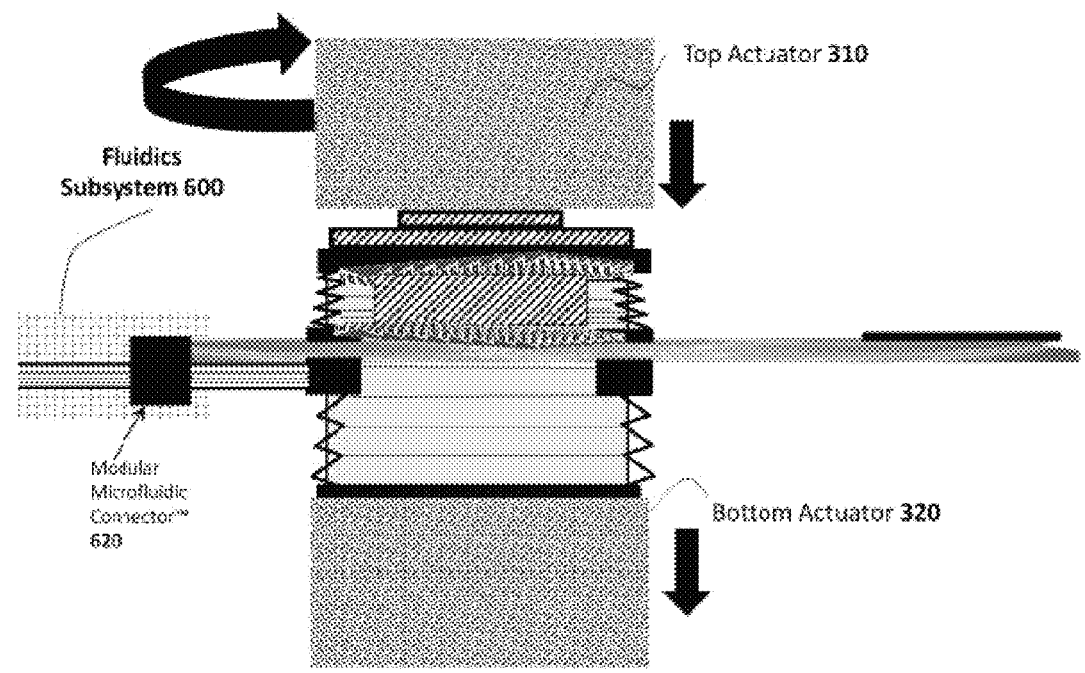
Figure 6G:
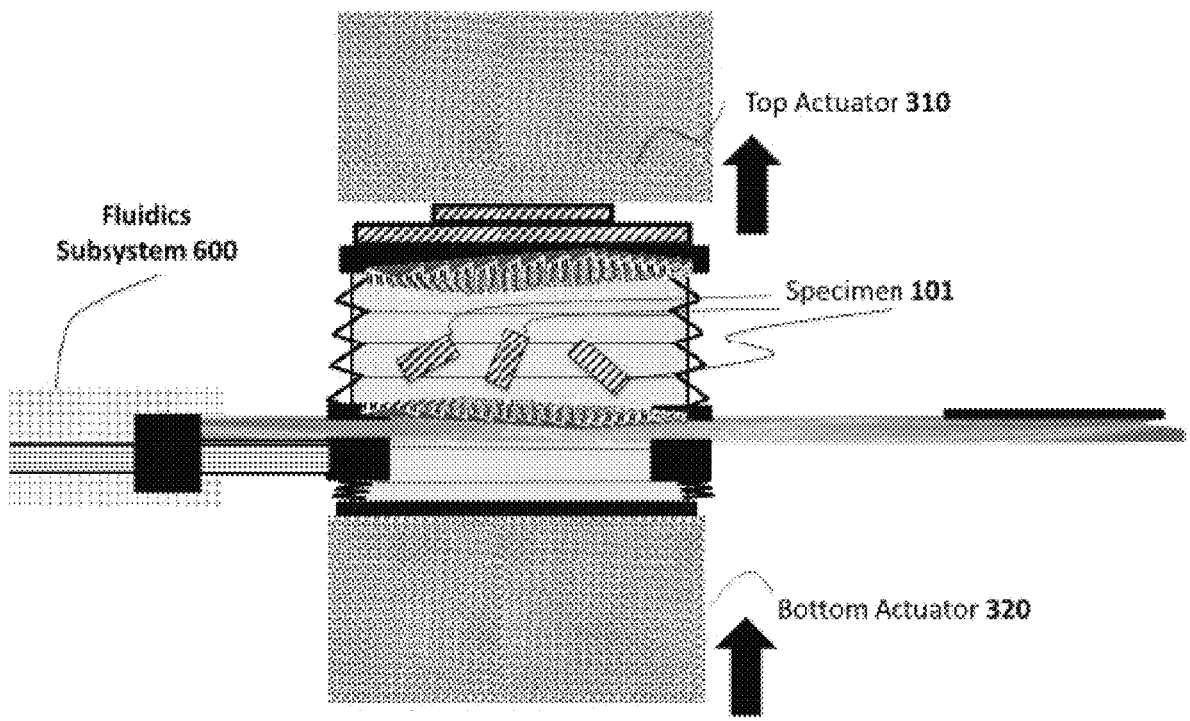
Figure 6H:
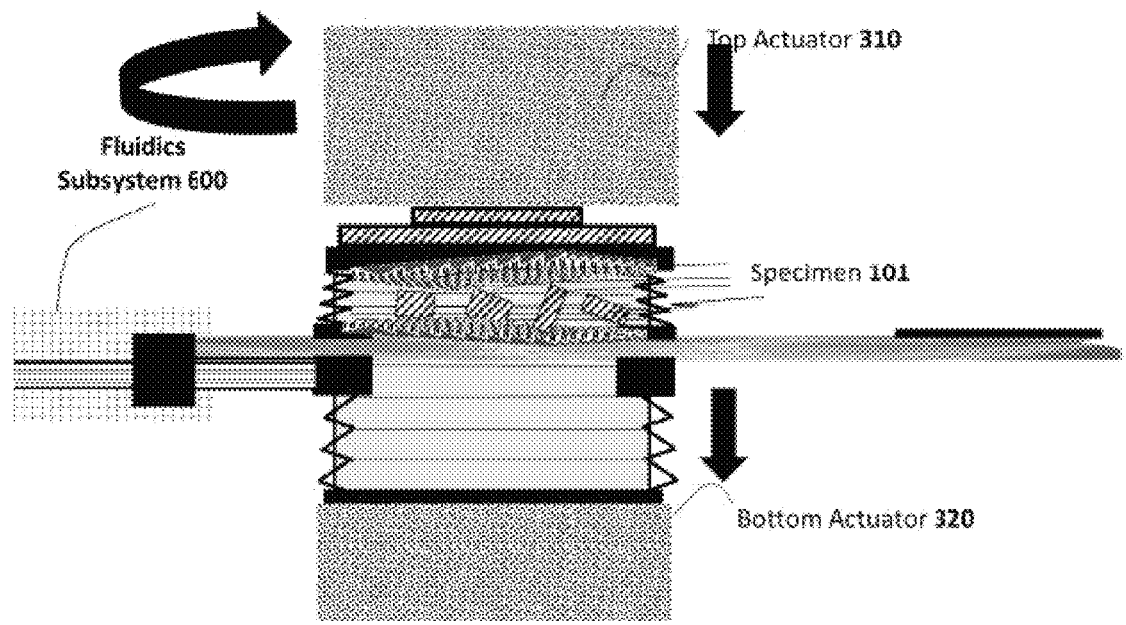

FIGS. 6F, G, and H show aspects of the cartridge 200 as it processes the specimen 101. FIG. 6F shows the bottom actuator 320 moving down at the same rate the top actuator 310 is moved down, forcing the dissolution solution through mesh 225 and into the bottom compartment of the cartridge 200. Top actuator 310 can in some embodiments rotate (as illustrated) or move in the x and y axes (not shown) to grind the specimen 101 between grinding features 220. FIG. 6G shows the actuators moved up, and FIG. 6H shows the actuators moved down again with specimen 101 being fragmented into smaller pieces or single cells 1000 and nuclei 1050 released. The timing of the movement of the actuators can be adjusted to the tissue type. The movement can titrate the specimen 101 through mesh 225.

At appropriate intervals, aliquots can optionally be withdrawn through modular microfluidic connector 610 or other fluidic connectors or by pipetting, and the number of cells or the viability determined by Measurement Subsystem 500. In some embodiments, a solution, such as a dye such as trypan blue, can be added to the aliquot to visualize live versus dead cells using a brightfield readout. The solutions can be imaging reagents, such as fluorescently directly conjugated antibodies or secondary antibodies, stains, fluorescent probes and dyes; imaging nanomaterials (including quantum dots and other nanoparticles), or other contrast or straining reagents. Many other compounds can be added if fluorescence or other imaging systems are used. In addition, in some embodiments, Measurement Subsystem 500 does not image the aliquot but measures light scattering or fluorescence of the aliquot to determine the number of cells, or the viability; in some instances, after an initial readout of the fluorescence assay of ATP or other intracellular components, all the cells in the aliquot can be lyzed to determine the total amount of ATP or other intracellular component to create a ratio of the percentage of viability. The Measurement Subsystem 500 can perform multiple readings as required and in some embodiments the amount of grinding, trituration, or enzymatic composition or concentrations can be adjusted based upon the measurements.

Figure 6I:
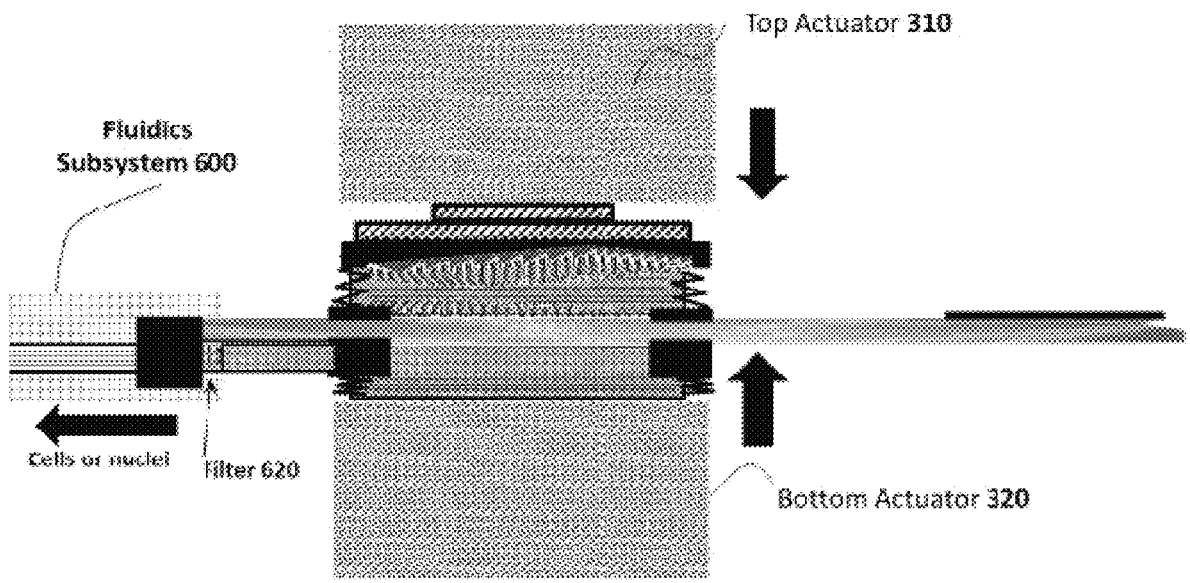

Referring to FIG. 6I, after the appropriate amount of processing, which can be determined optionally by Measurement Subsystem 500, both actuators are moved towards holder 235 to push the liquids through modular microfluidic connector and onto a filter 620 such as a 5 □m, or 10 □m, or 20 □m or other filter that retains the singulated cells. In some embodiments, tangential flow filtration is used.

Figure 6J:
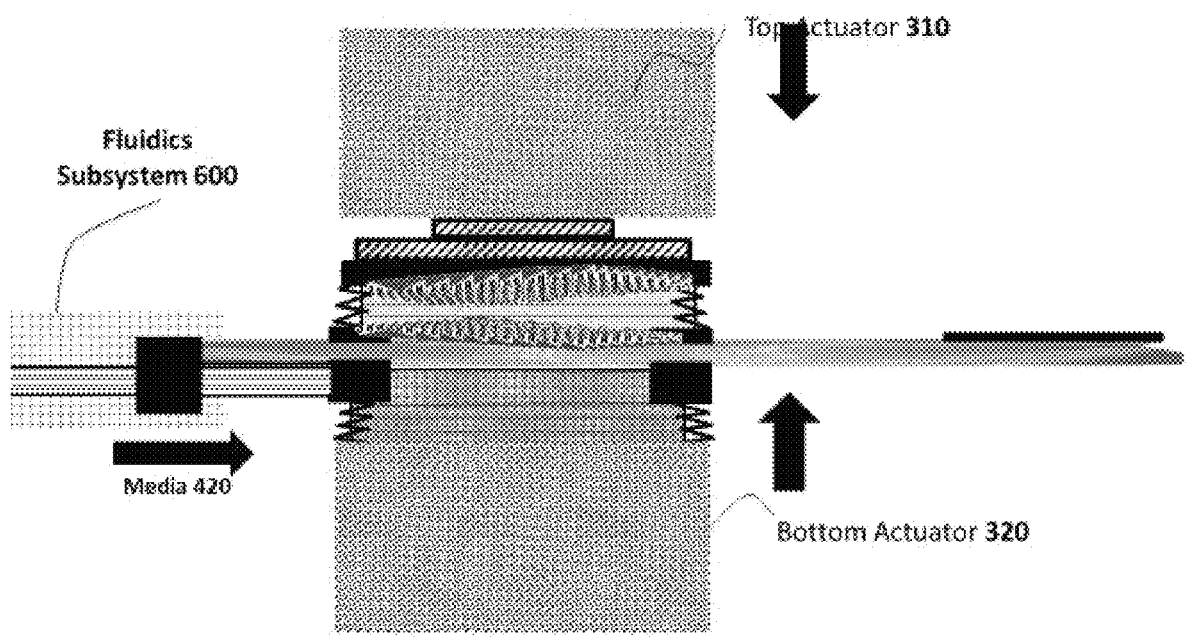

Referring to FIG. 6J, Fluidic Subsystem 600 can then deliver media 418 into the cartridge 200 through filter 620 to change the liquid from the dissolution solution 410 to the appropriate media 418 such as Hank's balance salt solution (HBSS) with 2% fetal calf serum or any other buffer, media, or solution. The amount of media 418 can be adjusted based upon the readout by Measurement Subsystem 500 to produce a desired titer such as 1, 10, 100, 1,000 or other numbers of cells/□L.

Figure 6K:
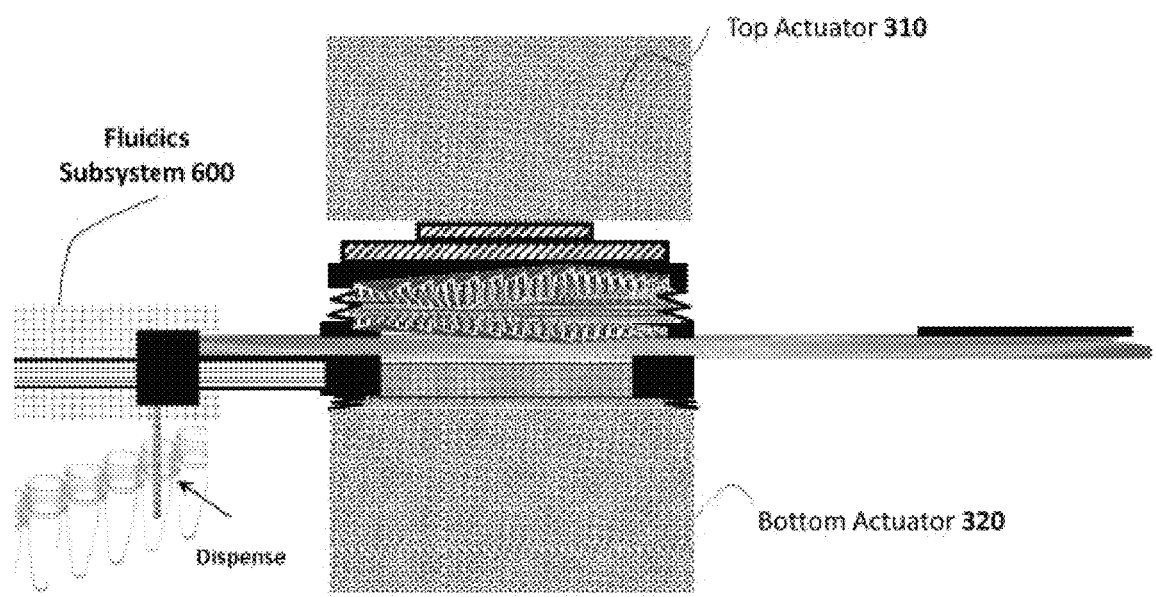

Referring to FIG. 6K, the resuspended single cells can then be output through modular microfluidic connector 230 to strip tubes, Eppendorfs, microtiter plates, or other vessels, or into the next module for a multistage process, such as preparing sequencing libraries.

In some embodiment, labeling solutions such as antibodies or particles, such as paramagnetic beads, can be added to cartridge 200. In other embodiments, the Fluidic Subsystem 600 is cleaned of debri, single cells, or tissue fragments by separate cleaning modules that operate in direct contact or non-contact mode utilizing various cleaning mechanisms including, but not limited to, mechanical brushes or chemical agents comprised of ethanol, alcohols, detergents, non-ionic detergents, surfactants, water, buffers, acidic solutions, basic solutions, and other chemicals.

In other embodiments, solutions that dissolve the cellular membrane, such as 0.1% Triton X-100 or 0.005% Nonident P40 are added either alone or in combination with physical, chemical, acoustic, enzymatic, thermal, or other methods to produce cellular organelles such as nuclei, mitochondria, ribosomes, long non-coding RNA, or other nucleic acids.

Example: Orifice Cartridge.

Figure 7A:
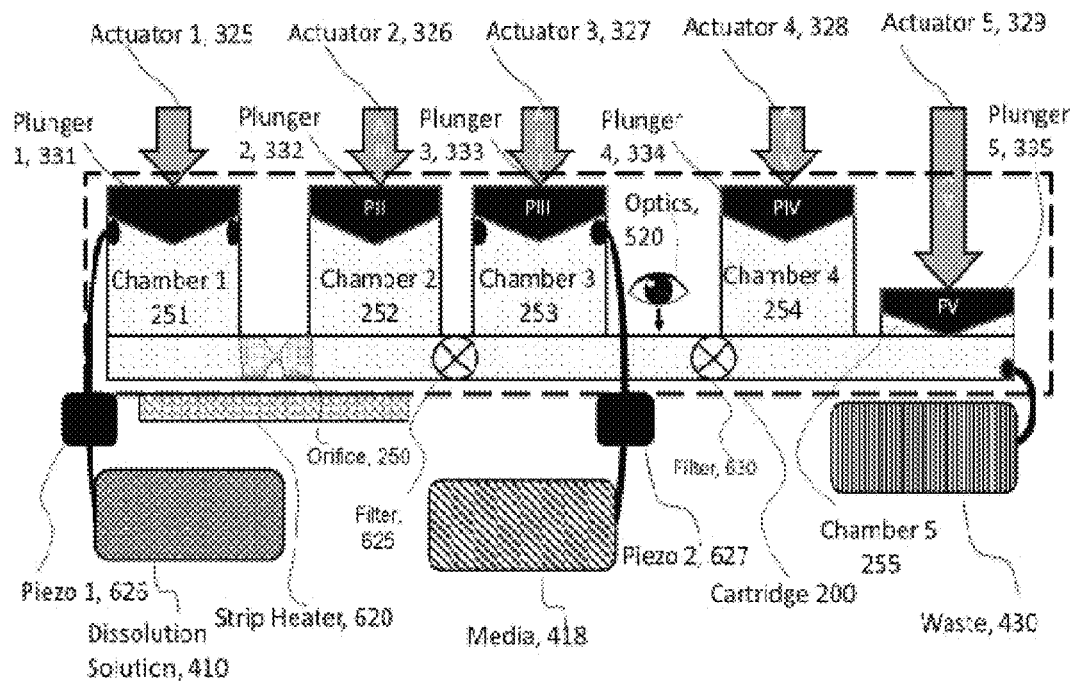
FIGS. 7A-G shows a cartridge with an orifice.
Figure 7B:
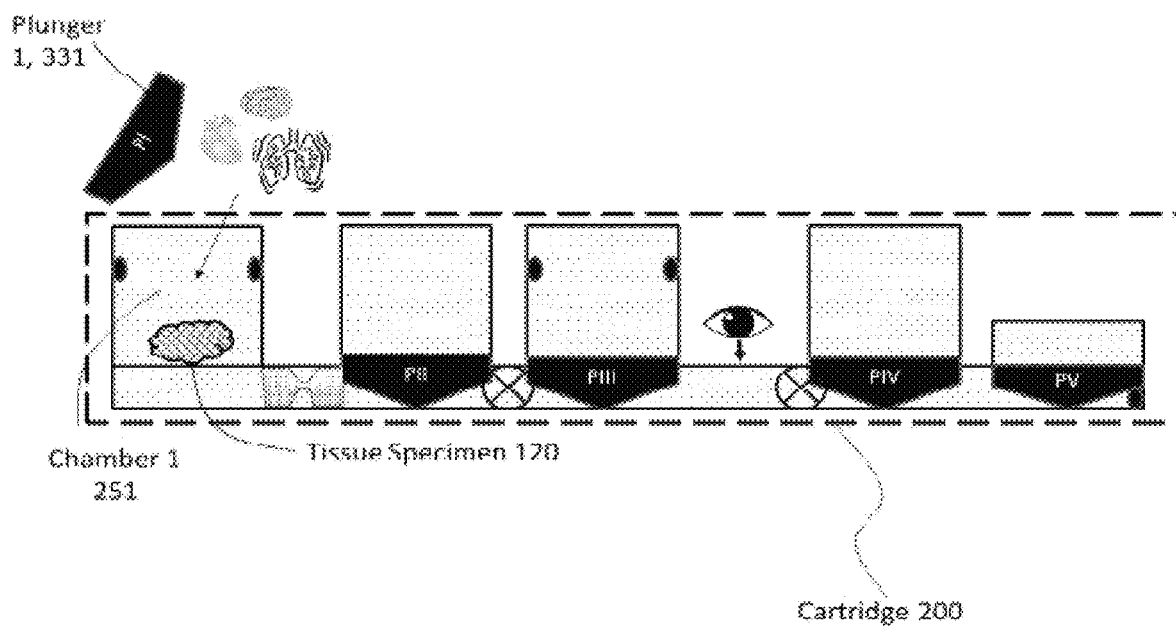

In another example, FIG. 7A shows a cartridge 200 designed to pass the specimen 101 through orifice 250 to physically disrupt tissue as well as relevant parts of the instrument. In a preferred embodiment, the cartridge 200 has four chambers with an orifice 250 located between chamber 1 251 and chamber 2 252 for tissue dissociation, a filter 625, such as a 70 □m, or 50 □m, or 30 □m or other filter, between chamber 2 252 and chamber 3 253 for separation of dissociated cells from rest of the tissue, and filter 630, such as a 5 □m, or 10 □m, or 20 □m or other filter, between chamber 3 253 and chamber 4 254 for removal of enzyme solution as well as debris.

In one embodiment, five actuators, 325, 326, 327, 328, and 329 in the instrument engage with plungers 331, 332, 333, 334, and 335 respectively on the cartridge in a manner to allow them to pull or push the plungers up or down. Piezoelectric pump 626 can access dissolution solution 410 from a reservoir and piezoelectric pump 627 can access media 418 from a reservoir. Strip heater 620 can control the temperature in the cartridge. Waste reservoir 430 collects waste from cartridge 200 as needed. The eye represents an optics imaging system 520 including illuminator and detector.

In some embodiments, the number of actuators can be one or more. In some embodiments, the actuators are syringe plungers, in others, on cartridge pumps, or off cartridge pressure or vacuum sources. In another embodiment one actuator such as a syringe plunger can move specimen 101 from chamber 1 251 through orifice 250 into chamber 2 252 which can have a plunger or be open to atmospheric or other pressure and serve as a reservoir for specimen 101 as it is processed through orifice 250. In some embodiment a strainer or filter to disrupt tissue or filter single-cells for clumps can be incorporated.

Figure 7C:
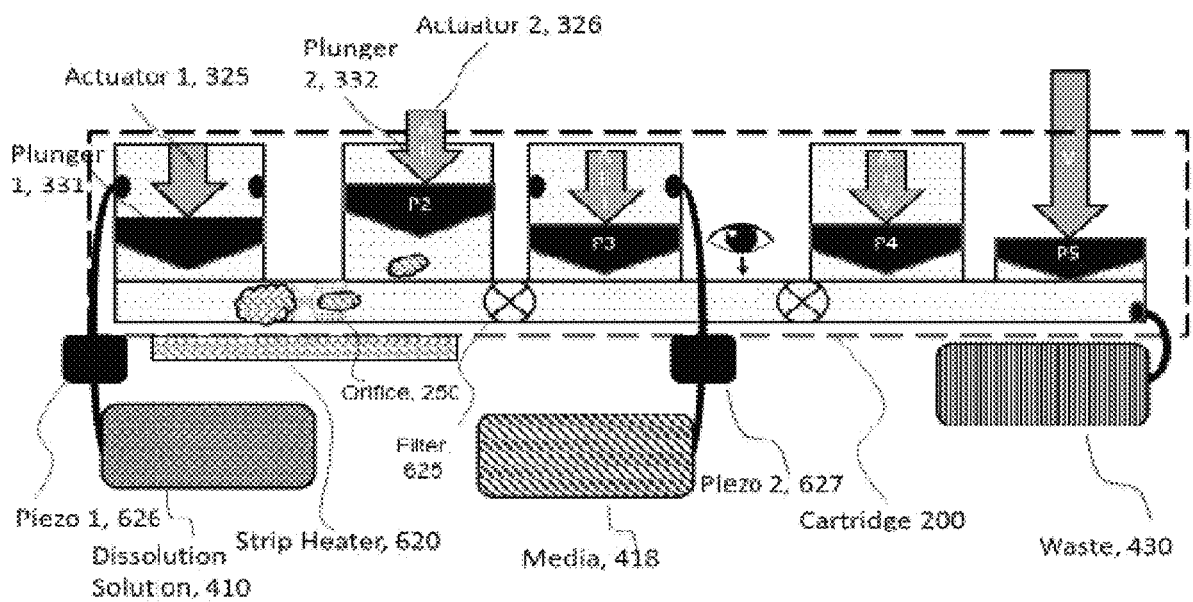

FIGS. 7B-G illustrates one embodiment of the workflow. In the first step, FIG. 7B, tissue specimen 120 is placed into chamber 1 251, either by removing plunger 1 331 or through a cap (not shown). FIG. 7C shows the lid/plunger 331 placed onto chamber 1 251 and the cartridge 200 inserted into the instrument. Dissolution solution 410 is added to chamber 1 251 using piezoelectric pump 626 and the solution is optionally heated using strip heater 620 to a constant temperature such as 37° C.; Peltiers or other temperature control elements can also be utilized. The specimen 101 can be held at the desired temperature to incubate the specimen 101 for the time required.

As shown in FIG. 7C, actuator 1 325 can push down on plunger 1 331 and actuator 2 326 can pull up on plunger 2 332 to force specimen 101 through orifice 250 which disrupts the tissue and into chamber 2 252. This can be reversed, with actuator 1 325 pulling up and actuator 2 326 pushing down to move the tissue back through orifice 250 into chamber 1 251 causing dissociation. The cycle can be repeated as often as desired.

Figure 7D:
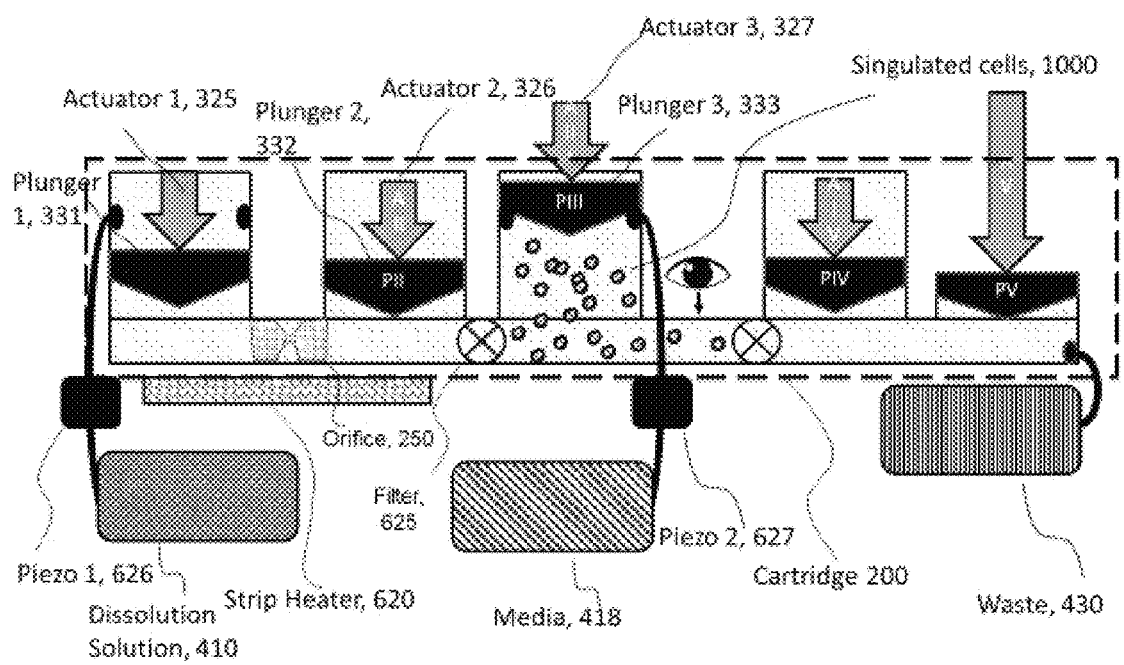

Referring to FIG. 7D, both actuator 1 325 and actuator 2 326 can be pushed down to force dissociated tissue through filter 625 which separates clumps and non-dissociated tissue from singulated cells 1000 and move the solution into chamber 3 253. Strip heater 620 can be turned off. To further move the Referring to FIG. 7E, actuator 3 327 pushes down on plunger 3 333 and actuator 4 328 pulls up plunger 4 334 to force dissociating solution as well as debris smaller than the pore size of filter 630 into chamber 4 254 while singulated cells 1000 remain on the chamber 3 253 side of filter 630.

Actuator 4 328 can then push down on plunger 4 334 while actuator 5 329 can pull up on plunger 5 335 to move the debris and enzyme solution to chamber 5 255. Actuator 5 329 can then push down on plunger 5 335 to move the debris and enzyme solution to waste 430.

Optics 520 can interrogate the solution to determine the titer of single cells 1000 or nuclei 1050 and when desired the viability. Referring to FIG. 7F, actuator 3 327 pulls plunger 3 333 up creating a temporary vacuum while piezoelectric pump 612 pumps media 418 into chamber 3 253. Media 418 can be a buffer, such as PBS, HBSS, etc, a solution to process the cell suspension such as red blood cell lysis solution or paramagnetic beads with antibodies, a growth media, an indicator solution or a combination.

To then change the media or wash the cells, actuator 3 327 pushes plunger 3 333 down while actuator 4 328 pulls up plunger 4 334 to move the added solution through filter 630 into chamber 3 253 while singulated cells 1000 remain on the Chamber 3 253 side of the filter 630. The solutions can be moved back and forth between chambers 3 253 and chamber 4 254 as needed using actuators 3 327 and 4 328.

Figure 7E:
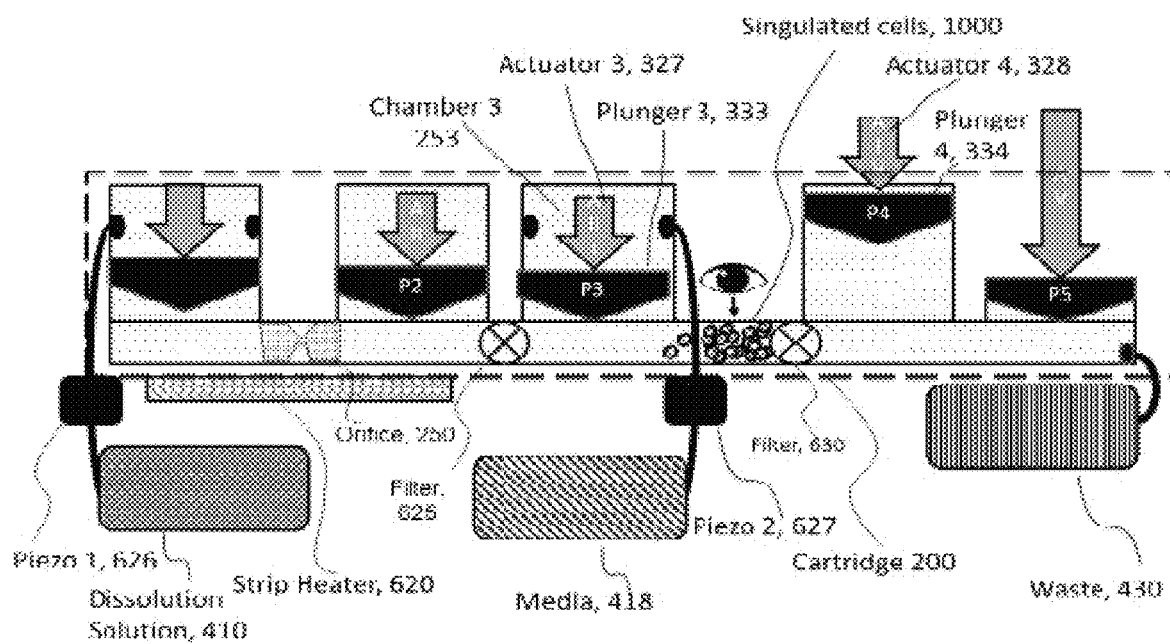
Figure 7F:
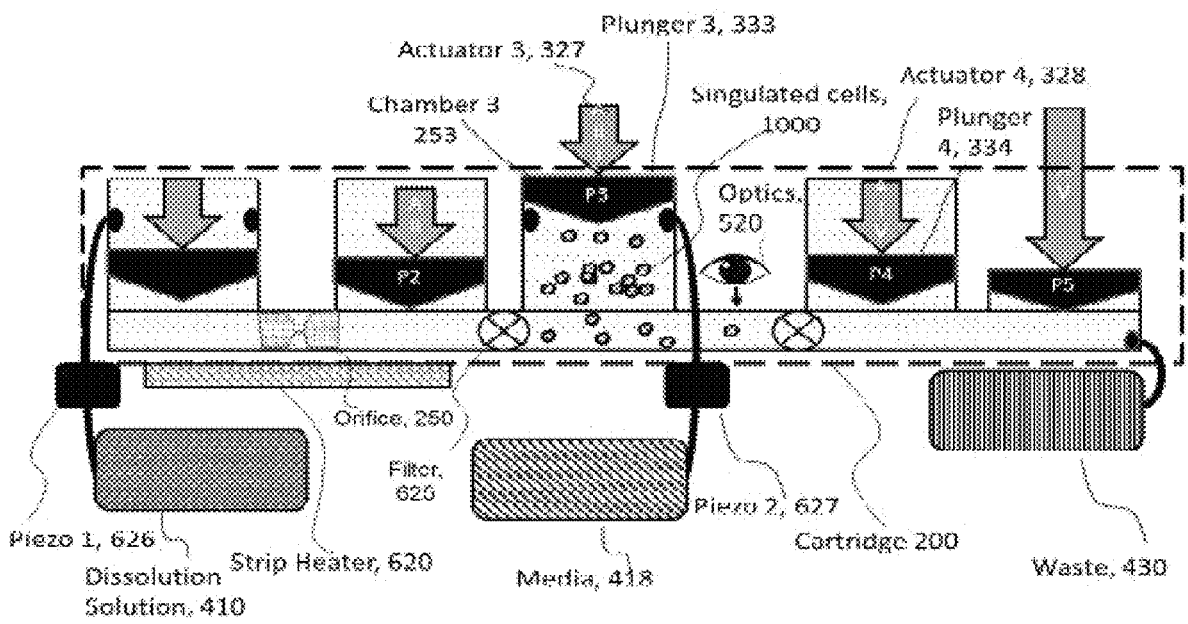

These steps illustrated in FIGS. 7D, 7E, and 7F can be repeated to perform additional cycles of either media change, enzymology, or processing, with the cells washed and the filtrate moved into waste 430.

Figure 7G:
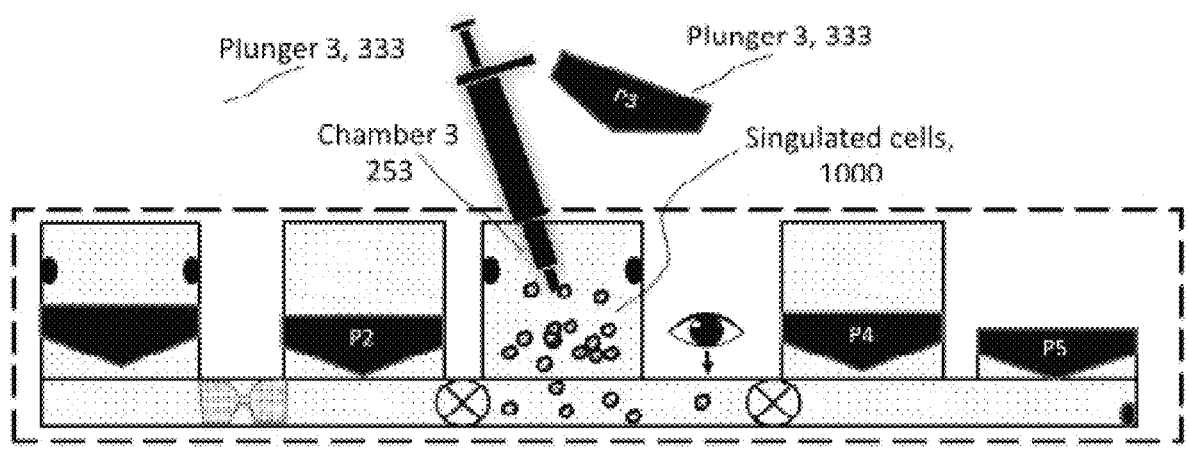

Referring to FIG. 7G, once the cells have been processed as desired, such as resuspension in the media of choice at the desired titer, cartridge 200 can be removed from the instrument and plunger 3 333 removed and allowing the single cell suspension 1000 to be pipetted out with a device such as a syringe 370. In other embodiments, the plunger 3 333 can be pierced by a needle to remove the single cells 1000 to prevent aerosol formation or a cap 210 can provide access to the processed tissue specimen 120.

Example: Automated Mechanical Device.

Figure 8:
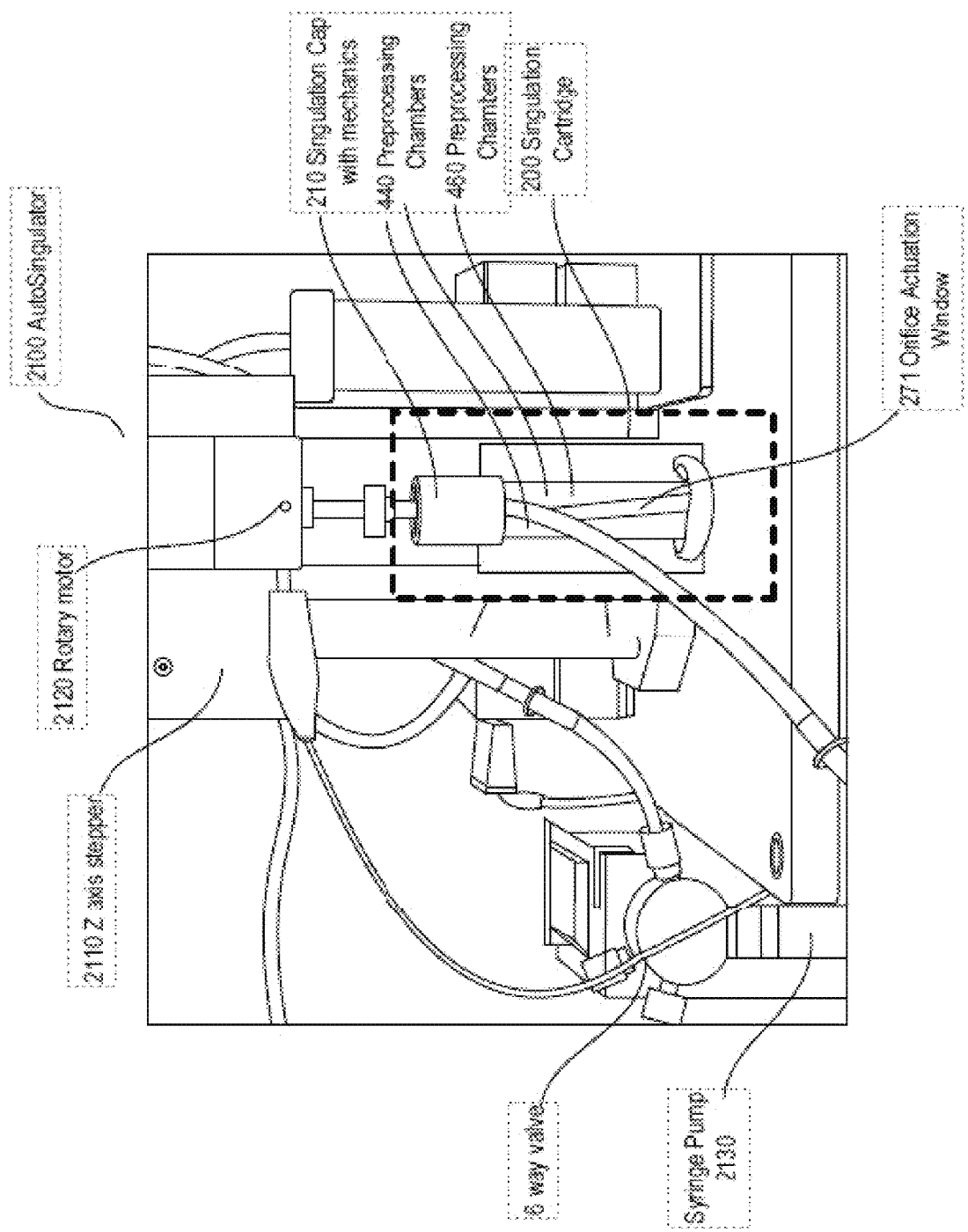
FIG. 8 shows a device that can perform mechanical processing of specimens with fluidic and mechanical control.

There are many ways to mechanically disrupt tissue. In one embodiment of a Singulator System 100, a mechanical device, the AutoSingulator™ 2100, automated and standardized multipled mechanical disruption methods. In one embodiment the device in FIG. 8 has a z-axis stepper 2110, a rotary motor 2120, and a syringe pump 2130 with a six-way valve 2140, all controlled by control software 725. FIG. 8 shows the AutoSingulator 2100 testing a-three-chamber cartridge 200 designed for a variable orifice mechanical disruption and mechanical processing with a cap 210 that has a mechanical device inside the cap 210.

Variable Orifice and Cartridge Example.

A standard disruption method is trituration, passaging tissue through orifices which can be of successively smaller diameters of fixed orifices, e.g., needles, Pasteur pipettes, etc. which works well for some tissues. However, the fundamental problems in developing a cartridge using orifices are incorporating the orifices in series, preventing clogging, and adapting the orifice sizes to the requirements of different tissue types. These problems are all solved by a variable orifice 490 that can be adjusted to create successively smaller orifices on demand or lumens of different sizes.

Figure 9:
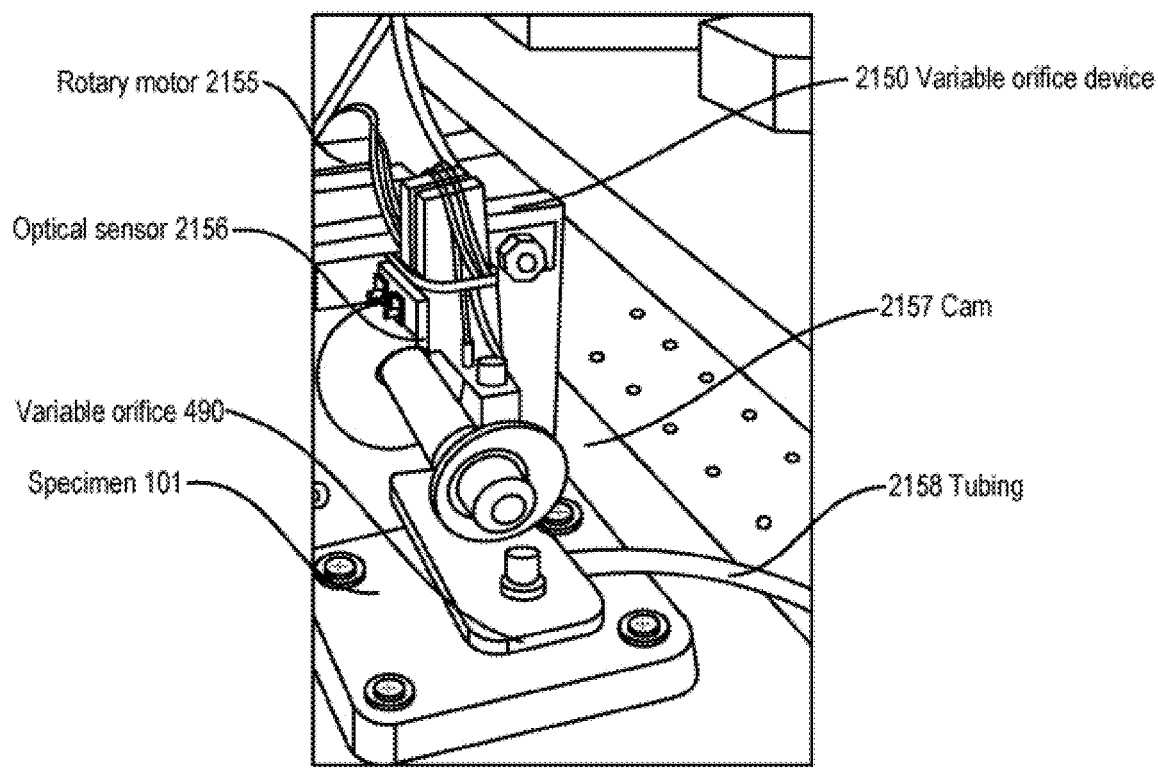
FIG. 9 shows an automated device to create a variable orifice.
Figure 10A:
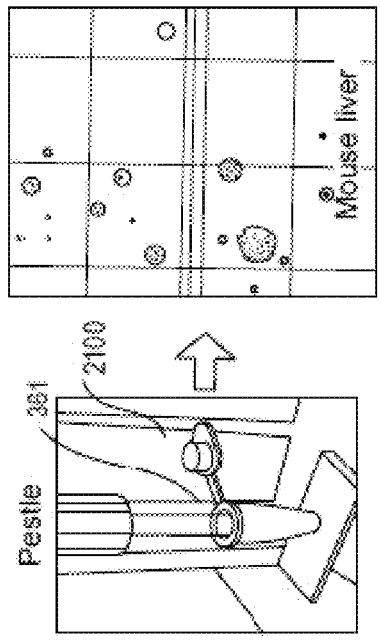
FIG. 10A-D shows four types of automated mechanical dissociation methods and examples of tissue processing.

As shown in FIG. 9, an automated variable orifice device 2150 has been designed, built, and tested integrated with the AutoSingulator 2100. A rotary motor 2155 with an optical sensor 2156 and a cam 2157 can compress a section of tubing 2158, e.g., 3 mm ID Tygon tubing, to change the internal cross-section of the tubing to create a variable orifice 490 (obscured by the mechanism). As shown in FIG. 10A, the automated variable orifice device 2150 has been tested with mouse lung with 0.1% Collagenase I and 0.05% DNAse and has produced viabilities up to 70% and titers of greater than $4 \times 10^6$ cells from tissue specimens 120 of approximately 100 mg.

Rotating Physical Dissociators

Rotation of one or more surfaces is a method to physically dissociate tissue and methods are herein disclosed. The rotating part can be directly driven by a mechanical coupling or use a magnetic coupling to achieve the rotation. The speed of rotation can be programmed by Control Subsystem 700 for example to 1, 10, or 100 rotations per minute or other speeds and the direction reversed as desired. In some embodiments, the rotation can create fluid flow which can be exploited to move specimen 101 into grinding or crushing features. The rotating physical dissociators can be combined with features described for the cartridge with collapsible features or the orifice cartridge as will be obvious to one skilled in the art.

Referring to FIG. 11, in a preferred embodiment, tissue specimen 120 is inserted into cartridge 200 with a chamber 340 where the physical disruption is performed. After the tissue specimen 120 is placed into chamber 340, enzymatic or chemical dissolution solution 410 can be added and rotating plunger 336 is inserted, which can be incorporated into cap 210, and cartridge 200 placed into the Singulator System instrument 100 where an actuator (not shown), that can rotate and move in the z direction, engages with the rotating plunger 336. In another embodiment, enzymatic or chemical dissolution solution 410 is added through channel 343. The rotating plunger 336 has grinding features 220 that can be molded or otherwise fabricated as a single piece or can be attached through adhesive 337. The actuator can rotate rotating plunger 336 to grind tissue specimen 120 on filter 341 which can be comprised of a filter or mesh such as a stainless mesh with 70 □m, 150 □m, 220 □m, or other mesh sizes and is held in place by filter support 342. The actuator can also push down or pull up on rotating plunger 336 to force tissue specimen 120 through filter 341 or a combination of rotation, and depressing and withdrawing rotating plunger 336 can be used to optimize performance for different tissue specimens 120. An actuator assembly can incorporate force gauges to provide feedback for the pressure the plunger or actuator is exerting on tissue specimens 120. In many instances, gentle pressure followed by withdrawal of the force will be appropriate with an incubation period to allow optional enzymatic activity to dissociate the loosened cells and aggregates. As singulated single-cell suspensions 1000 are produced, channel 343 can be used to move single cells 1000 or nuclei 1050 into other sections of the cartridge with functionality to wash the cells, titer, and determine viability.

FIG. 12 shows another preferred embodiment of rotating disruptor 344 with a grinder rotor 420 (FIG. 12A) and grinder stator 421 (FIG. 12B). Referring to FIG. 12C, grinder stator 421 is incorporated (or placed) into the bottom of chamber 340. Tissue specimen 120 and enzymatic of chemical dissolution solution 410 are added followed by grinder rotor 420 which can be part of cap 200. An optional stabilizer rod 252 can help maintain rotary alignment between grinder stator 421 and grinder rotor 420. In the presence of an external rotating magnetic field, magnetic impellers 348 on grinder rotor 420 can propel the grinder rotor 420 to spin and staggered grinding teeth 355 on grinder rotor 420 and grinder stator 421 disrupt tissue specimen 120. The force on the tissue specimen 120 can be adjusted by moving either the relative position of chamber 340 or magnetic stirrer 349.

Figure 10B:
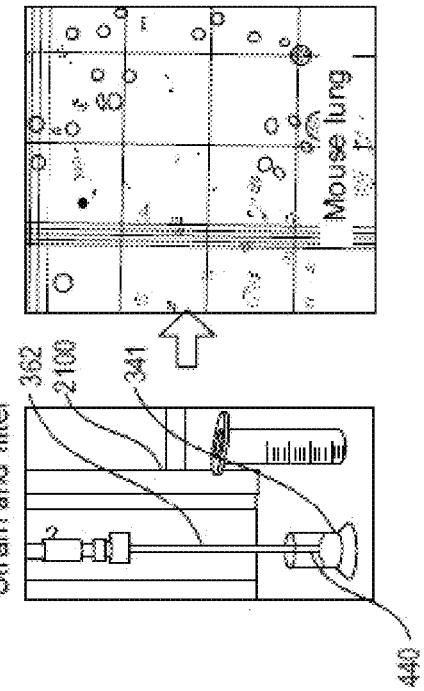
Figure 10C:
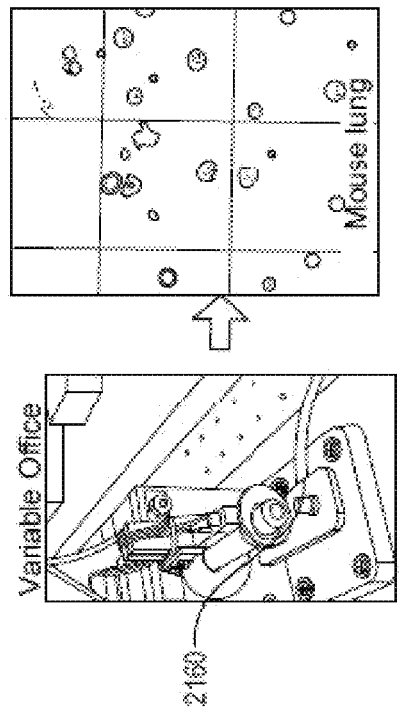

As shown in FIG. 10C, a rotating disruptor 344 or grinding device has been attached to the AutoSingulator 2100 and used with Pre-Processing Chambers 440 after incubation for 30 min off device in 0.1% Collagenase I and 0.05% DNAse at 37° C. to disrupt fresh mouse lung to produce single-cells with 90% viabilities and a titer of $1.20 \times 10^7$, sufficient for deep single-cell NGS.

FIG. 10B shows pestle 361 attached to the AutoSingulator 2100 with dissociation in an Eppendorf tube. The picture on the right side of FIG. 10C shows the dissociation of mouse liver using pestle 361 method to yield 33% viable single-cells in suspension at a titer of $3.8 \times 10^6$. The pestle method may be best suited for very hard tissues or producing nuclei or organelles.

Figure 10D:
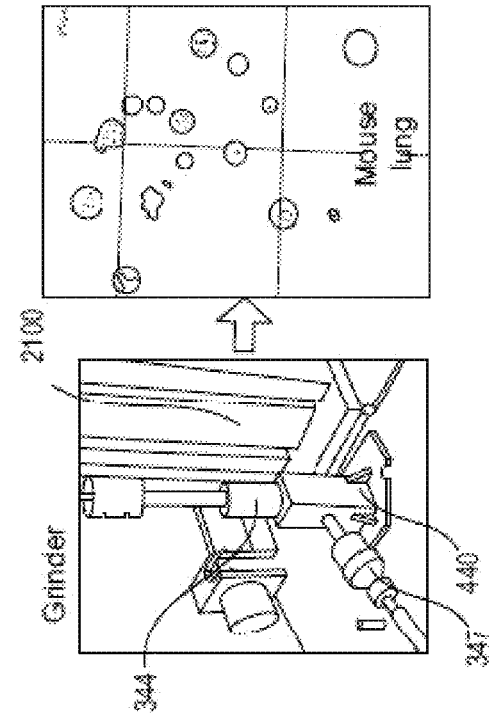

FIG. 10D shows plunger 362 attached to the AutoSingulator 2100 with dissociation of mouse lung through a 75 □m filter 341 in a simple cartridge 200; the right panel shows dissociation of mouse spleen into single-cell suspensions with 70% viability with a $5.67 \times 10^7$ titer using this setup.

Figure 13:
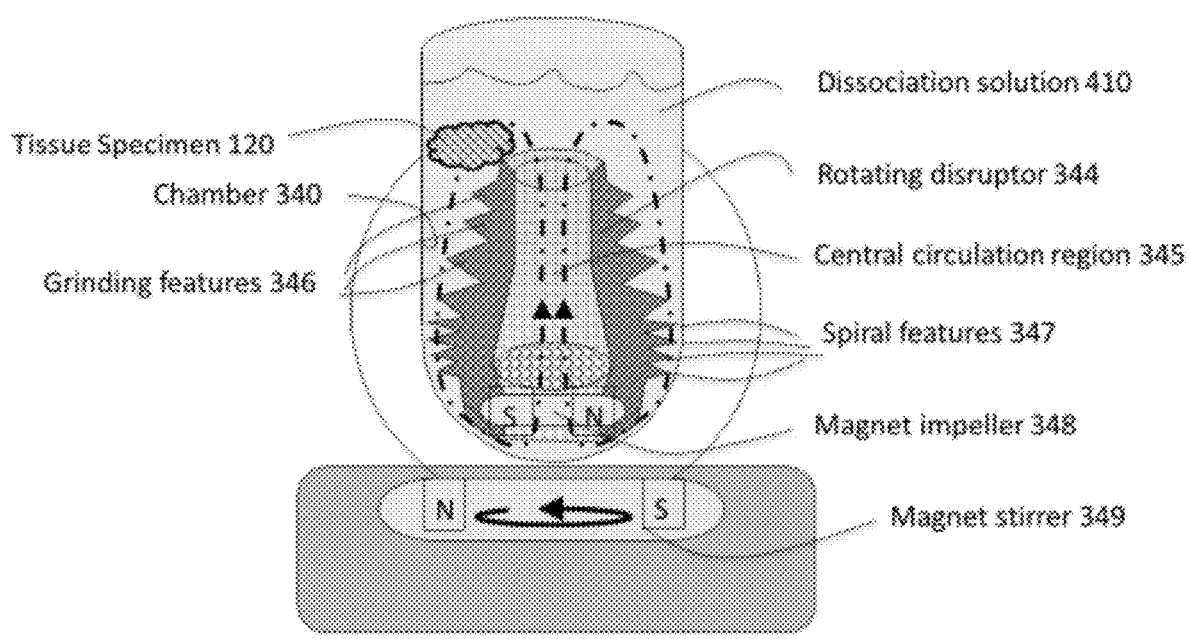
FIG. 13 is a design of a magnetically coupled rotating disruptor with external spiral features to circulate fluid through a central circulation region as grinding features disrupt the tissue specimen.

Referring to FIG. 13, an example of a rotating disruptor 344 is shown. Rotating disruptor 341 is placed in chamber 340 and tissue specimen 120 is added. Enzymatic or chemical dissociation solution 410 can be added before or after tissue specimen 120. The cartridge containing chamber 340 is engaged with the instrument which has a magnetic stirrer 349. Magnetic stirrer 349 is used to rotate the rotating disruptor 344 using magnet impeller 348 attached to rotating disrupter 344. As the rotating disrupter 344 spins, spiral features 347 pull tissue specimen 120 into the outside of rotating disrupter 344 where grinding features 346 can disrupt specimen 101 into smaller pieces. In some embodiments, grinding features 346 can have coarse and fine grinding features. In some embodiments, grinding features 346 can function as spiral features 347 to aid circulation of dissociation solution 410 and tissue specimen 120. As rotating disruptor 344 spins, enzymatic or chemical dissociation solution 410 is pulled down and into central circulation region 345 where the solution and any pieces of tissue specimen 120 flow up to the top of central circulation region 345. The rotation can be adjusted for speed and started and stopped as appropriate. Spiral features 347 can be designed to force the liquid either up and down depending on design intent.

Figure 14:
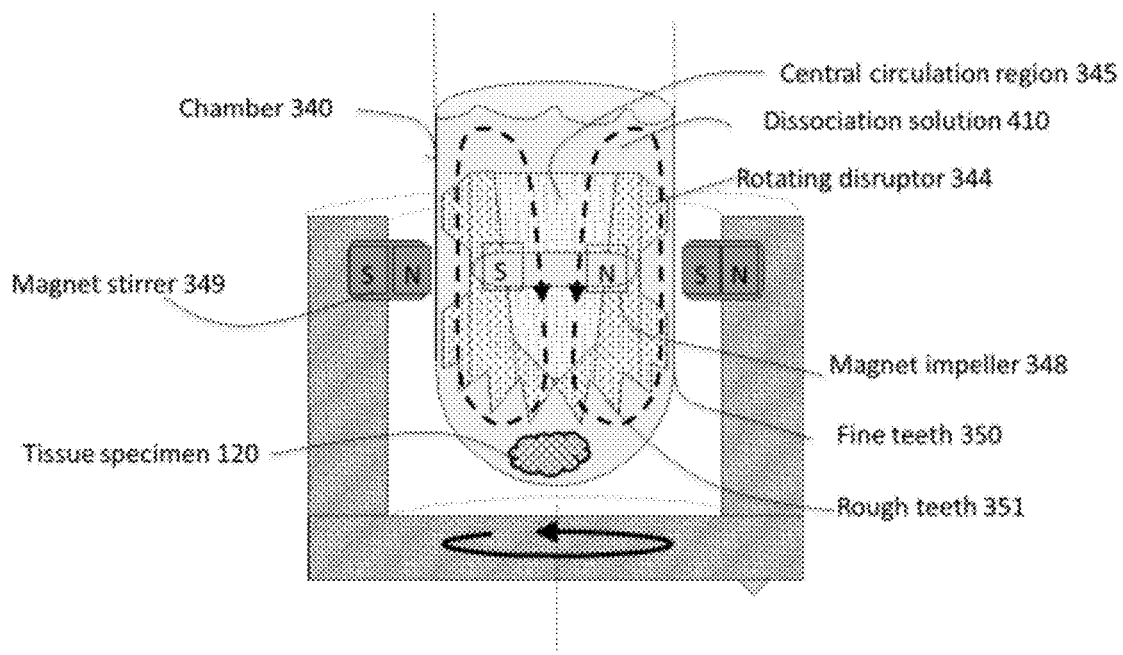
FIG. 14 is a design of a magnetically coupled rotating disruptor that can exert adjustable force on the specimen. The disruptor has external spiral features to circulate fluid through a central circulation region as grinding features disrupt the specimen which is initially placed below the rotating disruptor.

FIG. 14 shows a rotating disruptor 344 driven by a magnetic stirrer 349 which is elevated with respect to the bottom of chamber 340. In this example, tissue specimen 120 and enzymatic or chemical dissociation solution 410 are added to chamber 340 and rotating disruptor 341 is placed into the chamber. Magnetic impeller 348 will align to the height of magnetic stirrer 349. If chamber 340 is moved up or down, magnetic impeller 348 magnets will pull the rotating disruptor 344 up or down to exert adjustable pressure by fine teeth 350 and rough teeth 351 on tissue specimen 120. Liquid flow induced by rotory motion of rotating disruptor 344 forces smaller tissue fragments into and through the fine teeth 350.

FIG. 15A-D show two examples of rotating disruptors 344 with different pitches of spiral features 347 with large grinding features 346 on the bottom of the rotating disruptors 344. In this example the gaps in spiral features 347 also can disrupt the specimen 101.

FIGS. 16A and B show an embodiment where the rotating disruptor 344 is placed above specimen 101 and the liquid motion is induced by spiral features 347 on the outside of the rotating disruptor 344 with recirculation through central circulation region 345. In addition to disruption as specimen 101 interacts with spiral features 347, the bottom can be a grinding surface 357. Magnet holes 356 are shown that hold magnets to create the magnetic impeller 348. This example did not produce good yields or viabilities with mouse liver tissue. FIGS. 16C, D, and E show an embodiment where the rotating disruptor 344 is placed above specimen 101 and the liquid motion is induced by spiral features 347 on the outside of rotating disruptor 344 and by internal spiral 357 on the inside of rotating disruptor 344 with recirculation through central circulation region 345. In addition to disruption as specimen 101 interacts with spiral features 347 and internal spiral 357, the bottom can be a grinding surface 357. This embodiment can be 3D printed to create the internal spiral 357. This design worked better than the one shown in FIG. 16A with better circulation of the specimen 101 through the internal spiral 357 but also did not produce high yields and titers for mouse tissues.

FIG. 17 is an example of a multiple piece assembly to form rotating disruptor 344. FIG. 17B shows external piece 360. Mesh 358, such as a stainless mesh with 70 □m, 150 □m, 220 □m, or other mesh sizes, or filters, is inserted into the top of external piece 360 to form the assembly shown in FIG. 17A. FIG. 17C shows internal piece 359 which is then inserted and press fit into the assembly to form the completed rotating disruptor 344 shown in FIG. 17D. Internal piece 359 forms internal spiral 357. Specimen 101 is added on top of rotating disruptor 344 and the rotation of the mesh 358 and fine teeth 350 disrupt specimen 101 with internal spiral 357 creating circulation to pull the specimen 101 down onto the mesh 358. The speed of rotation can adjust the force of the pull onto mesh 358. Larger sizes of mesh 358 can produce larger pieces of the specimen 101. The fine teeth 350 can be supplemented with larger teeth as desired for different tissues.

Cartridge Examples

Cartridges 200 have been designed to accommodate multiple mechanical disruption methods—variable orifice, pestle, grinding, and straining—with mechanical transduction in many designs through the cartridge cap 210. The cartridges can be designed for tissue samples of different sizes, such as ~3 mm³ or larger and process the tissue in 0.3 to 1.0 mL of liquid, or for tissues<3 mm³ and process the tissue in volumes such as <0.1 mL, or in 0.1 to 0.3 mL, or in greater than 0.3 to 1.0 mL or larger of liquid.

Referring to FIG. 18, one embodiment of cartridge 200 has two basic functionalities: one or more Preprocessing Chambers 440, to produce single-cells 1000 or nuclei 1050 and Processing Chamber 460 to perform the optional additional processing such as magnetic pulldown, red blood cell lysis, or library preparation including on or off-cartridge but on instrument nanodroplet/nanobolus single-cell cDNA processing.

The embodiment shown in FIG. 18 implements a variable orifice 490 with a three-chamber cartridge: two Preprocessing Chambers 440 pass specimen 101 back and forth through variable orifice 490 in tubing using a syringe plunger designed into cap 210 to create pressure or vacuum to move specimen 101, and a Processing Chamber 460 that receives the single-cell 1000 or nuclei 1050 suspension which is strained through a 50 □m or other filter 341 as it enters Processing Chamber 460. Pinch valve 471 is employed to open or close the path to Processing Chamber 460. In a preferred embodiment, cap 210 can couple the mechanical motion from a Singulator System 100 such as the AutoSingulator 2100 to disrupt specimen 101 such as moving a plunger or spinning a rotating plunger 336. In a preferred implementation, shown in FIG. 18, the specimen 101 can be moved by a plunger that is coupled through the cap 210 and actuated by the Z-axis stepper 2130 on the instrument or rotated by the rotary motor 2120 as needed. In other implementations, syringe pump 2130 can deliver fluids to cartridge 200 to move the preprocessed single-cell suspension 1000 or nuclei suspensions 1200, nucleic acids 1072, biomolecules 1070, subcellular components 1060, or other products from pre-processing.

Figure 19:
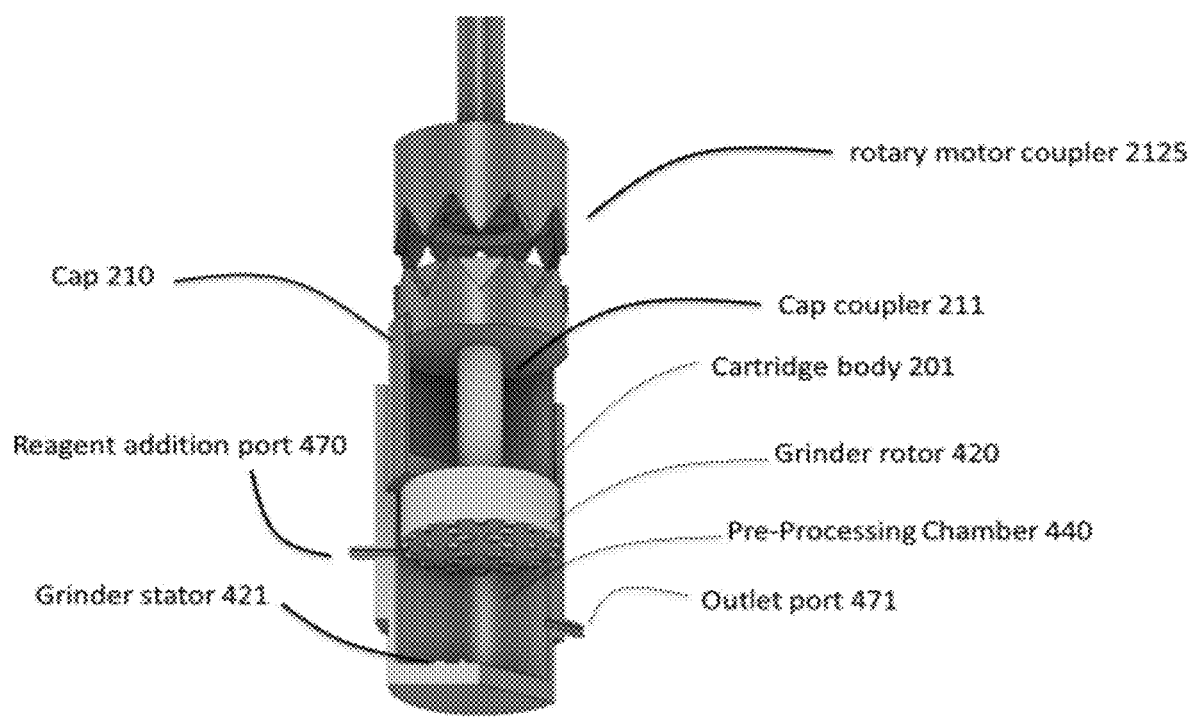
FIG. 19 shows a cutaway of a cap design for a grinding implementation.

FIG. 19 shows a design with a cap 210 that couples a mechanical grinder rotor 420 in the cap 210 using cap coupler 211 to connect to rotary motor coupler 2125 on the instrument. The rotation motion of rotary motor 2120 is transmitted through rotary motor coupler 2125 to cap coupler 211 to rotate mechanical grinder rotor 420 in either direction while the vertical position of grinder rotor 420 is controlled by z axis steper 2110. In some embodiments the grinder rotor 420 only travels downward to the bottom of the chamber while in others as described below it can be retracted by mechanisms such as magnetics, springs, or mechanical coupling.

Figure 20:
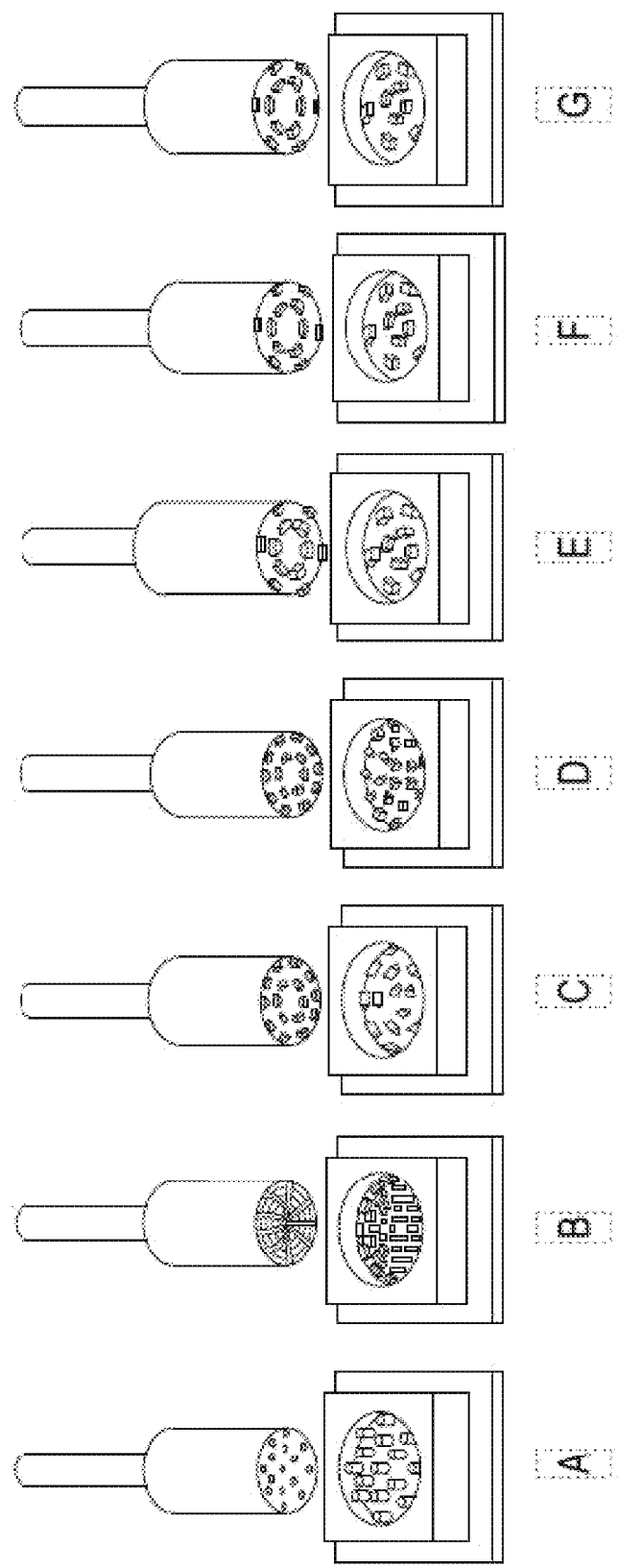
FIG. 20 shows seven paired grinder rotors and grinder stators.

FIG. 20 shows seven patterns of matching rotary grinders 420 and grinder stators 421 that have been designed and built. In add designs, the teeth on the rotary grinders 420 and grinder stators 421 are complementary and arranged in circular rows. FIG. 20A has a set with three rows of equally sized teeth with sharp edges. FIG. 20B has a set with five rows of successively smaller width of teeth as the center is approached on the rotary grinder 420 and the grinder stator 421. FIG. 20C has a set with three rows of equal sized sharp on the rotary grinder 420 and the grinder stator 421. FIG. 20D has a set with four rows of equal sized pointed 'shark's teeth' on the rotary grinder 420 and the grinder stator 421. FIG. 20E has a set with two rows of equal sized blunt 1.5 mm teeth on the rotary grinder 420 and the grinder stator 421. FIG. 20F has a set with two rows of equal sized blunt 1.0 mm teeth on the rotary grinder 420 and the grinder stator 421. FIG. 20G has a set with two rows of equal sized blunt 0.5 mm teeth on the rotary grinder 420 and the grinder stator 421. The design in FIG. 20G was used extensively and generated the highest titer and viability for the most types of tissues. In some embodiments, the spacing between the outside of the rotary grinder 420 and the grinder stator 421 is set to be 15 20, 25, 30, 35, 40, 45, or 50 □m or other spacing such that in some embodiments only single cells or nuclei can pass between the rotary grinder 420 and the grinder stator 421.

Figure 21:
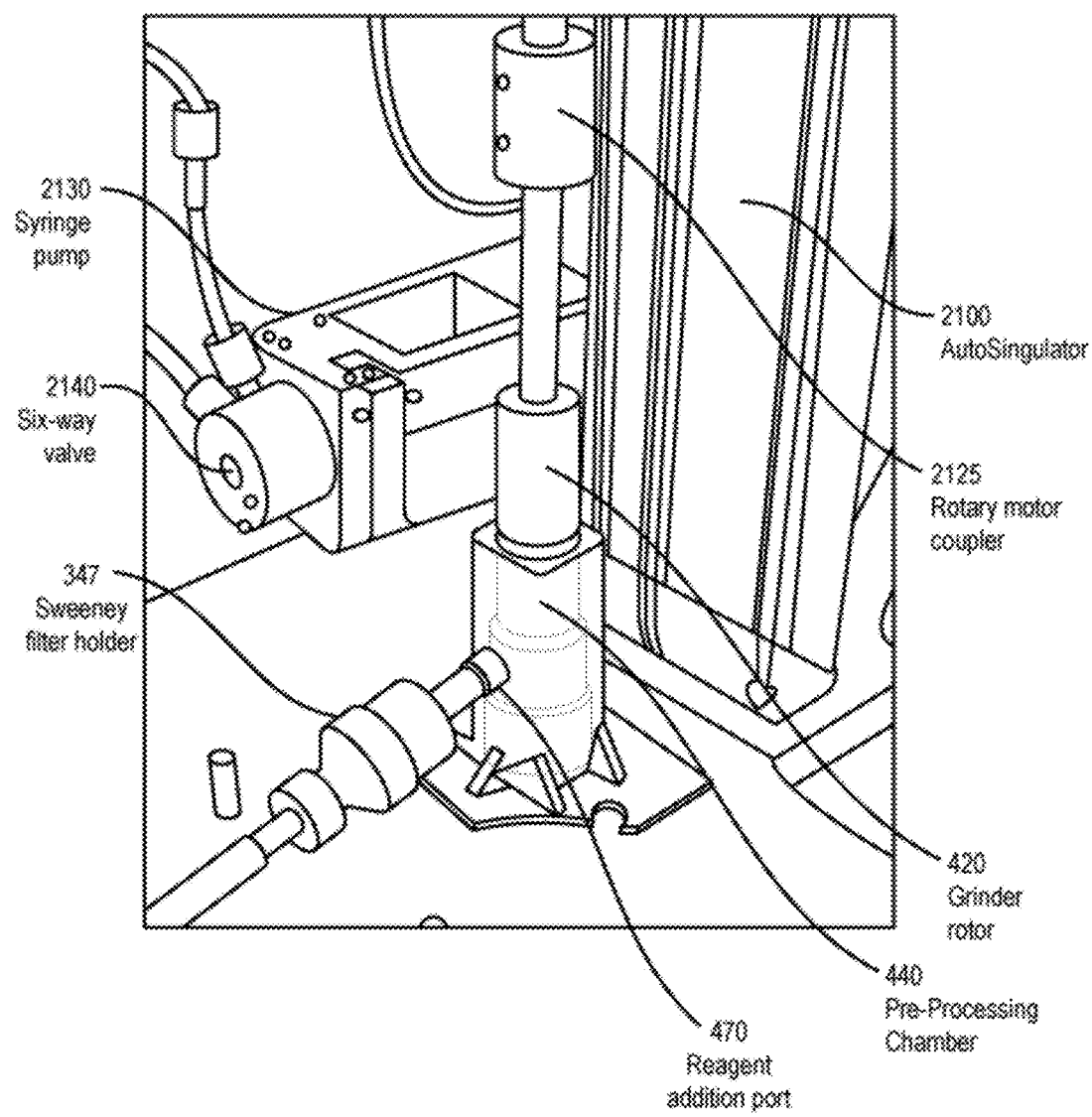
FIG. 21 shows an AutoSingulator instrument with a cartridge.

FIG. 21 shows a cartridge 200 embodiment with a Pre-Processing chamber 440 with the grinder stator 421 and a mechanical grinder rotor 420 (with the FIG. 20G design) connected through rotary motor coupler 2125 to rotary motor 2120 of the AutoSingulator 2100. Rotary motor 2120 can control the rotation of the grinder rotor 420 against fixed stator 421 in the bottom of the Pre-Processing chamber 440 and the Z axis stepper 2110 controls the vertical position of grinder rotor 420. The AutoSingulator 2100 delivers fluids, e.g., enzymatic or chemical dissolution solution 410, from syringe pump 2130 and six-way valve 2140 through Sweeney filter holder 347 holding a filter 341 to a reagent addition port 470 in Pre-Processing Chambers 440 through and can pull the pre-processed specimen 101 through Sweeney filter holder 347 holding a filter 341 such as a 70 □m filter. The setup in FIG. 21 has been tested for the singulation of cells and for the production of nuclei.

Examples of Tissue-Specific Workflows for Cell Singulation and Nuclei Production Using the AutoSingulator.

FIG. 22 shows the results of producing single cells 1000 in suspension from five different mouse tissues using AutoSingulator 2100 setup as shown in FIG. 21. A fresh tissue specimen 120 was placed in Pre-Processing Chamber 440 and positioned below the grinder rotor 420 attached to the AutoSingulator 2100. Control software 725 then lowered the grinder rotor 420 into the Pre-Processing Chamber 440. Dissolution enzymes added by syringe pump 2130 from 15 mL Falcon tubes to reagent addition port 470 on cartridge 200.

Preferred embodiments for formulation of enzymes for each mouse tissue were used in HBBS without Ca or Mg. For lung 0.1% Collagenase II with 5 u/mL Dispase and 0.03% DNase was used; for kidney 0.05% Collegenase I with 0.075% Papain and 0.03% DNase was used; for spleen, 0.05% Collagenase I with 0.03% DNase was used; for liver, 0.1% Collagenase IV with 0.05% Hyaluronidase and 0.03% DNase was used; for brain, 0.2% Papain with 0.03% DNase was used; and for gut, 0.1% Collagenase I with 0.025% Hyaluronidase and 0.03% DNase was used.

Figure 22A:
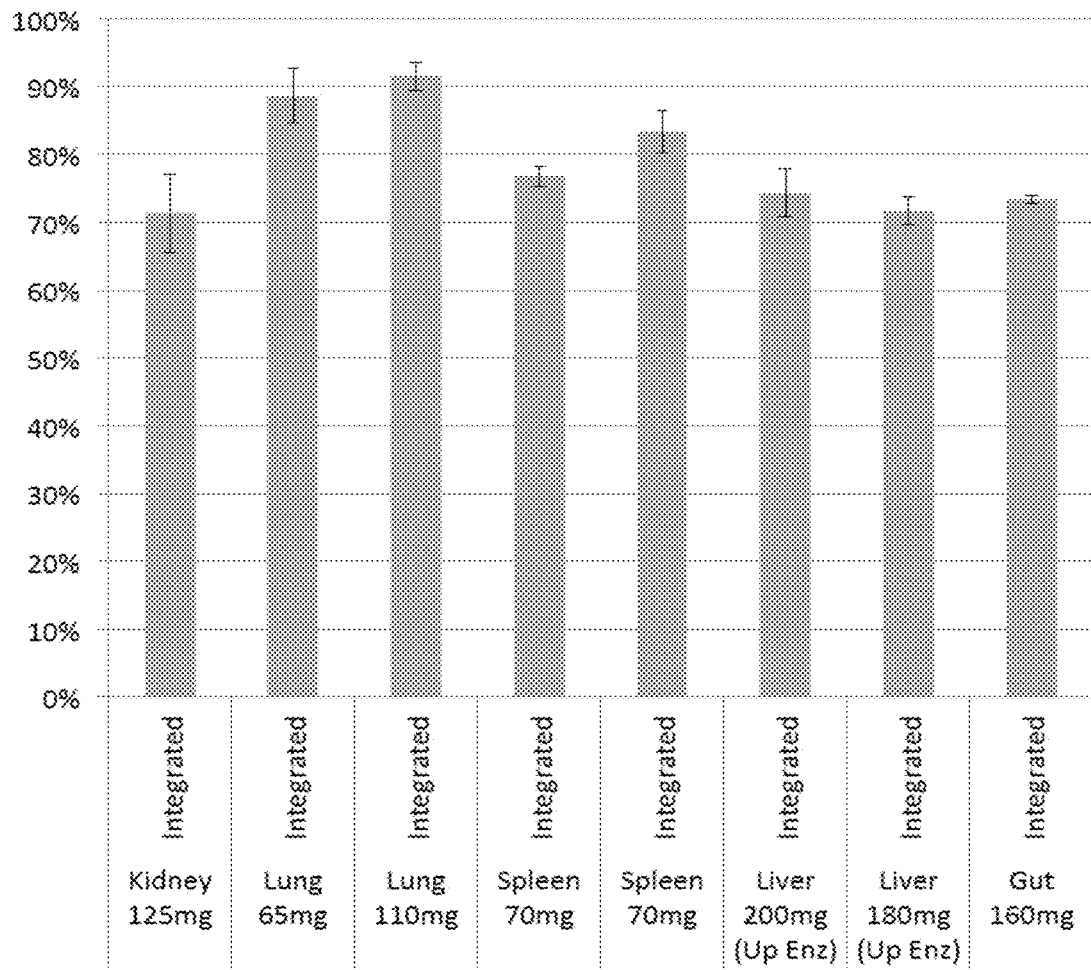
FIG. 22A-B shows the titer and viability of processing eight fresh mouse tissues into single cells using the AutoSingulator instrument with a cartridge.
Figure 22B:
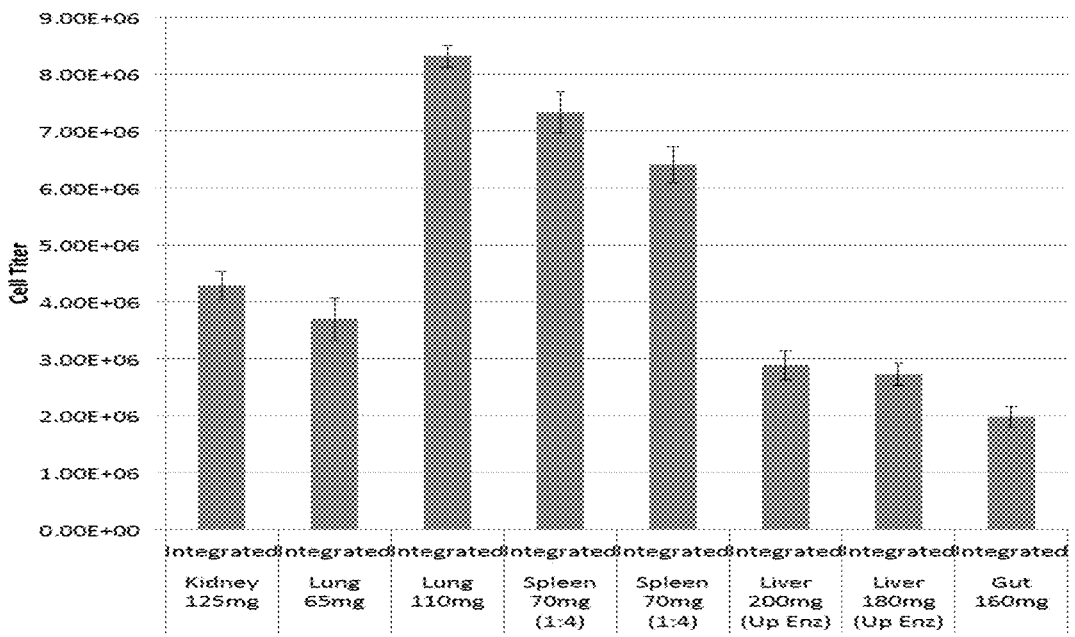

The operator then lowered grinder rotor 420 until it contacted the tissue. The rest of the operation was automated. The tissue specimen 120 was incubated for 30 min with the grinder rotor 420 moved up and down every 5 min to mix. After a 30 min incubation at room temperature, the grinder rotor 420 was rotated seven times forward and seven times backward at 75 rpm against the tissue specimen 120 with fixed stator 421 in the bottom of the Pre-Processing Chamber 440. The grinder rotor 420 was moved by the Z stepper 2110 about 200 □m down and the process repeated six to seven times until the grinder rotor 420 reached the bottom of the Pre-Processing Chamber 440 which had grinder stator 421. When the grinder rotor 420 reached the bottom of Pre-Processing Chamber 440, the dissociated sample was displaced through reagent addition port 470 through a 100 □m filter 341 held in a Sweeney filter holder 347 followed by a rinse with 3 mL of HBSS delivered backflushing through the 100 um filter 341 held in a Sweeney filter holder 347 into reagent addition port 470 and withdrawn back through 100 um filter 341 held in a Sweeney filter holder 347 and the output collected. The samples were centrifuged at 300 g for 5 min, the supernatant discarded, and the cells resuspended in RBC lysis buffer (G-Biosciences) for 3 min and then centrifuged at 300 g for 5 min and the pellet resuspended in 1 mL of HBSS. The viability and titer were determined on a Countess FL using Trypan blue. As shown in FIG. 22A, the single cells had viabilities ranging 72 to 92%, and as shown in FIG. 22B with yields of $2\times10^6$ to $8.3\times10^6$ cells for tissue specimens 120 from left to right of 125 mg of kidney, 65 mg of lung, 110 mg of lung, 70 mg of spleen, 170 mg of spleen, 180 mg of liver, and 160 mg of gut. The label of integrated on the X axis indicates that the complete process after lowering the grinder rotor 420 was performed by control software 725.

Figure 23:
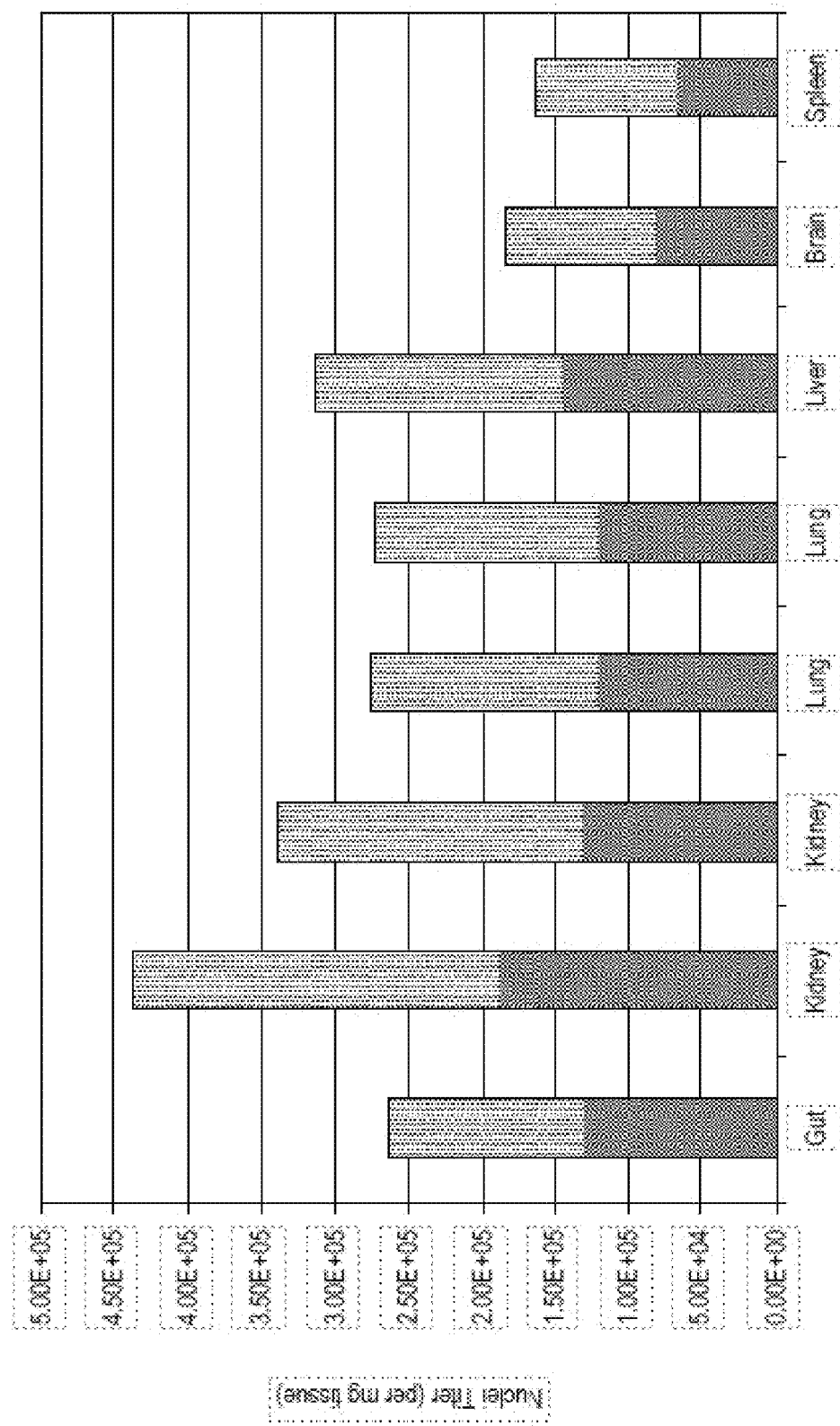
FIG. 23 shows the titer of processing mouse tissue into nuclei using the AutoSingulator instrument with a cartridge.

FIG. 23 shows the production of nuclei 1050 from six mouse tissues, gut, kidney, lung, liver, brain, and spleen, using the AutoSingulator 2100 setup as shown in FIG. 21. Tissue specimen 120 was added to the Pre-Processing Chamber 440 and then the Pre-Processing Chamber 440 was inserted under the grinder rotor 420 which was lowered by the software. The program then delivered Nuclei Homogenization Buffer (250 mM Sucrose, 25 mM KCl, 5 mM $MgCl_2$, 10 mM Tris-HCl, and 0.1% Triton-X) reagent from a 15 mL Falcon tube using syringe pump 2130 through sweeney filter holder 347 to reagent addition port 470 on cartridge 200. The AutoSingulator 2100 then immediately rotated grinder rotor 420 seven times forward and seven times backward at 75 rpm. The grinder rotor 420 was moved by the Z stepper 2110 200 □m down and the process is repeated six to seven times until the grinder rotor 420 reached the bottom of Pre-Processing Chambers 440 which contained grinder stator 421. When the grinder rotor 420 was at bottom of the chamber, the dissociated sample was displaced through reagent addition port 470 and through a 30 um filter 341 held in a Sweeney filter holder 347 followed by a rinse with 1 mL of Nuclei Homogenization Buffer delivered backflushing through the 30 um filter 341 held in a Sweeney filter holder 347 into reagent addition port 470 and withdrawn back through 30 um filter 341 held in a Sweeney filter holder 347 and the output collected. The samples were then centrifuged at 500 g for 5 min at 4° C. and the supernatant discarded. The nuclei 1050 pellet was resuspended in ice-cold Nuclei Storage Buffer (166.5 mM Sucrose, 5 mM $MgCl_2$, 10 mM Tris-HCl) and the titer determined on a Countess FL with Trypan blue staining. As shown in FIG. 23, with tissue specimens 120 from left to right of gut, kidney, kidney, lung, lung, liver, and brain, the most tissues had yields of $1.7\times10^5$ to $4.4\times10^5$ nuclei per mg of tissue input while spleen yielded $1.6\times10^6$ nuclei per mg of tissue input (note the spleen sample is a 1:10 dilution to enable plotting on the same chart). Similar results were obtained when 0.1% Nonident P40 was used in place of the Triton-X.

Example: Processing of Small Tissue Samples.

Many tissue samples are only present in small amounts, such as core biopsies or fine needle aspirates, where 5 to 25 mg of tissue may be obtained. The AutoSingulator 2100 was shown to be able to process these small samples effectively using the setup as shown in FIG. 21 for the production of both single cells 1000 and nuclei 1050.

FIG. 24 shows the results of processing a range of masses of four tissues to produce single cells 1000. The processing was as described above for FIG. 21 except the filtration was performed manually using a 70 □m filter. Lung, kidney, and gut tissues from 100 mg to 20 mg had viabilities of 70-94% for most samples (FIG. 24A) with yields over $10^5$ viable cells per 5 mg of tissue (FIG. 24B). The viability was similar until the mass was ~10 mg or less when the viability decreased. While the 5 mg specimens gave enough cell titer for downstream processing, the viabilities were low, indicating damage. Liver had generally lower viabilities and lower titers. The results demonstrate the cartridge 200 and AutoSingulator 2100 as shown in FIG. 21 can process tissue samples as small as 5 mg to produce single cells 1000 for single cell sequencing or cell biology or other applications.

Figure 25:
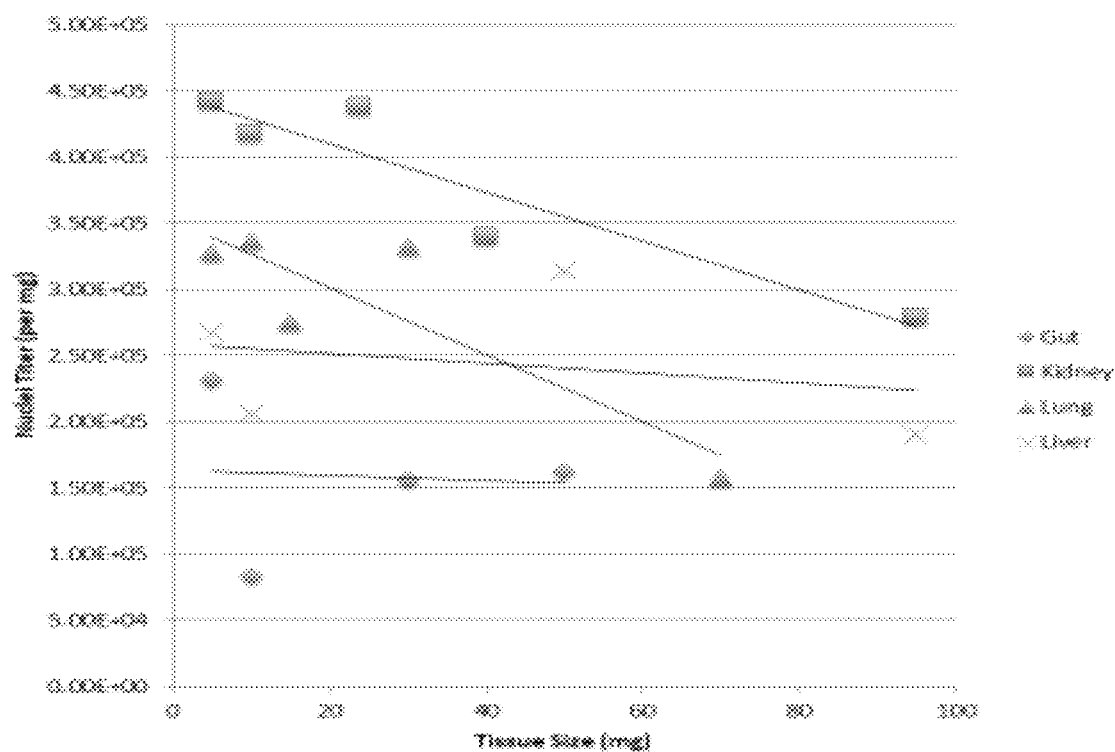
FIG. 25 shows the titer and viability of processing a range of sizes of mouse tissues into nuclei.

FIG. 25 shows the results of processing a range of masses of four tissues to produce single nuclei 1050. The processing was as described above for FIG. 23 except the filtration was performed manually using a 30 □m filter. The titers obtained were generally from 1.5 to $4.5\times10^5$ nuclei per mg of input tissue, yielding over 1,000,000 nuclei from a 5 mg tissue specimen 120 for most samples, ample for downstream single nuclei sequencing.

The results shown in FIGS. 23 and 24 demonstrate the utility of the Singulator System 100 for processing tissue specimens 120 into single cells 1000 and nuclei 1050 for small samples such as core biopsy samples or fine needle aspirates. These results show the Singulator System 100 can be applied to prepare clinical samples for single cell NGS and single nuclei NGS applications.

Quality control metrics.

Speed, yield, viability, and cellular damage are key first QC metrics for high quality, reproducible workflows. As manual and automated disruption methods are refined, after initial screening, additional quality metrics of qPCR of IEG and other transcripts, RIN determination using capillary electrophoresis, and single-cell NGS can be used as more sophisticated metrics.

It is important to identify enzymatic methods to produce single cells 1000 or nuclei 1050 with minimal alterations of gene expression as a major improvement to the state-of-the-art. Combinations of less digestive enzymes into formulations with less cellular reactions can be tested. Additives can help freeze the state of the cell, such as transcription, membrane, or other inhibitors, to prevent clumping, and to preserve RNA.

Figure 26:
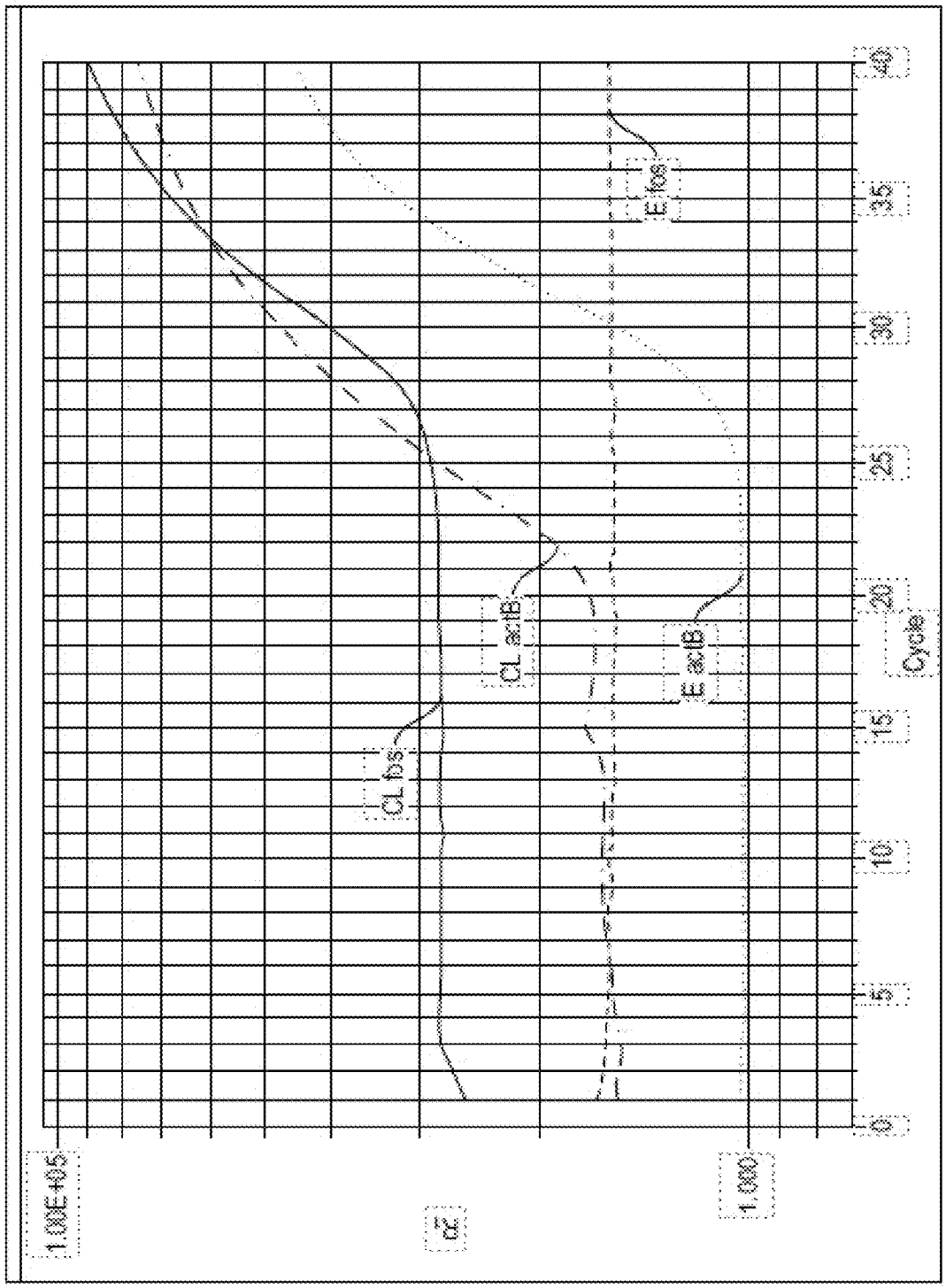
FIG. 26 illustrates using gene expression to monitor and develop processes on cartridges.

FIG. 26 shows examples of where two different processing methods to extract RNA have either induced the IEG gene fos or not induced it. In this experiment, mouse lung was pre-processed using rotating disruptor 344, as shown in FIG. 21 after incubation for 30 min at 37° C. in lung dissociation kit solution (Miltenyi 130-095-927). After the production of single cells 1000 in suspension, the cells were spun down at 300 g for 5 min and resuspended in HBSS. Aliquots of 10 □L were either lysed to release RNA by addition of 100 □L of the Extracta DNA kit (QuantaBio) with incubation at 95° C. for 30 min followed by addition of 100 □L of stabilization buffer or by addition of 200 uL CL buffer (10 mM Tris pH 8, 0.025% Igepal CA-630 (Sigma 18896-50), 150 mM NaCl) (adapted from K. Shatzkes, B. Teferedegne, and H. Murata. A simple, inexpensive method for preparing cell lysates suitable for downstream reverse transcription quantitative PCR. Sci Rep. 2014; 4: 4659. PMCID: PMC3983595) with incubation for 5 min at room temperature. 1 □L of each sample was added to 5 □L of qScript XLT One-Step RT-PCR Tough Mix, ROX reagent (QuantaBio) with 4.5 □L of molecular biology grade water, and 0.5 □L of actB primer (Thermo Fisher, m01205647_g1) or 0.5 □L of fos primer (Thermo Fisher, Mm00487425_m1).

FIG. 26 shows actB was expressed in spleen for both treatments (E actB was the Extracta processed sample with actB primers and CL actB was the CL buffer processed sample with actB primers). For the IEG fos gene, the lysis using the CL buffer induced fos while the Extracta kit processing did not. Because the Extracta kit shows no induction of fos, the production of single cells in suspension 1000 by rotating disruptor 344 did not induce fos, demonstrating the method is gentle with this enzymatic processing.

Singulator System Embodiment

Figure 27:
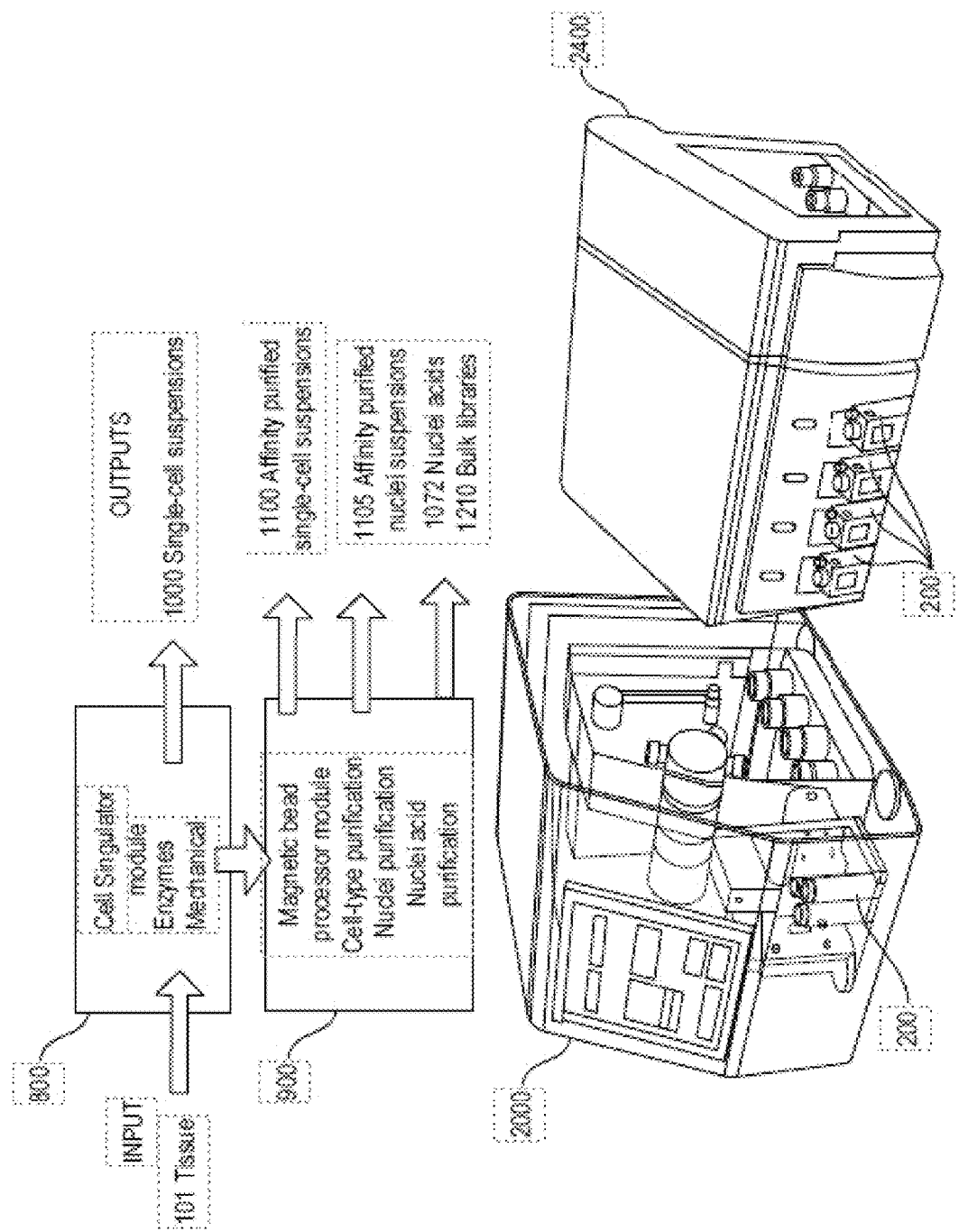
FIG. 27 shows the workflow for a Singulator System embodiment in the upper part of the figure, a single-sample design in the bottom left and a four-sample system design in the bottom right.

In one embodiment of the Sample Processing System 50 as a Tissue Processing System 80, as shown in FIG. 27, the Singulator System 100 can perform powerful integrated tissue-to-genomics functionality for genomic scientists to simply and standardize the production of single-cell 1000 or nuclei 1050 suspensions, affinity purified single cells 1100, affinity purified nuclei 1105, nucleic acids 1072, and bulk libraries 1210 from solid or liquid tissues. As will be obvious to one skilled in the art, the single cells 1000 and nuclei 1050 can also be used for cell biology, proteomics, metabolomics, and other analytical methods.

In this preferred embodiment a Cell Singulation module 800 and a Magnetic Processing module 900 are integrated into a Single-Sample Singulator System 2000 or into a Four-Sample Singulator System 2400. Mechanical and enzymatic dissociation is performed in single-use cartridges 200 in the Pre-Processing chamber 440 to produce single-cell suspension 1000 or nuclei suspensions 1200, nucleic acids 1072, biomolecules 1070, subcellular components 1060, or other products from pre-processing. The samples can then be processed in the Processing chamber 460 by optional bead-based affinity purification of cell types by surface antigens to produce affinity purified single-cell suspensions 1100 or nuclear suspension by nuclear antigens 1105 or nucleic acids 1072, biomolecules 1070, subcellular components 1060 can be further processed into purified mRNA, NGS libraries, or other sample types.

To accomplish this, in a preferred embodiment, a Single-Sample Singulator System 2000 was designed with reagents 411 on-board the instrument and with cartridges 200 potentially with tissue-specific mechanical disruption modalities to accommodate the wide diversity of processing needs. The system can input raw, unprocessed tissue samples and output single-cells 1000 or nuclei 1050 in suspension, ready for processing into single cell NGS libraries off device or can process the single cells 1000 or nuclei 1050 into bulk libraries on the system.

Example: A Single-Sample Singulation System.

The Singulator System 100 can mechanically disrupt tissue and enzymatically dissociate the disrupted tissue in a cartridge 200 into single-cells 1000 or nuclei 1050 in suspension. As shown in the top of FIG. 27, in one embodiment, a Cell Singulation module 800 combines the Physical Dissociation Subsystem 300 and the Enzymatic and Chemical Dissociation Subsystem 400 to produce single-cell 1000 or nuclei 1050 suspensions. The instrument provides the mechanical motion and fluidics to the cartridge which in turn mechanically and enzymatically or chemically processes the tissue into single cells 1000 or nuclei 1050. Multiple reagents 431 can be stored on the instrument with cooling as needed.

Figure 28:
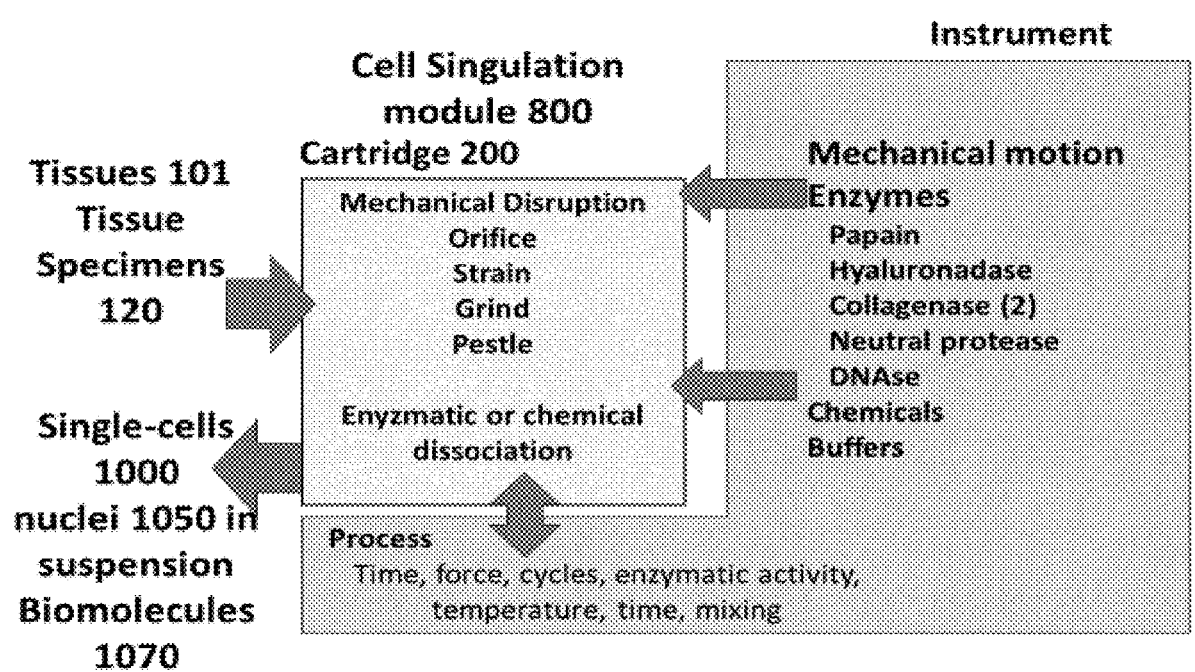
FIG. 28 shows the overall design concept of the Cell Singulation module for a prototype showing functional modules.

The Cell Singulation module 800 as shown in FIG. 28 combines the mechanical disruption of specimen 101 on cartridge 200, adds enzymatic or chemical dissolution solution 410 and other fluids according to the protocols, and controls sample movement, pressures, and temperature. The Cell Singulation module 800 can move or rotate a syringe plunger, pestle, or grinder, using a z axis stepper 2110 with a rotary motor 2120 coupled through the cap 210.

Referring to FIG. 27, magnetic purification of cell types and nuclei using affinity capture reagents attached to paramagnetic beads using Magnetic Processing module 900 integrates the capabilities to produce affinity purified cell types 1100 and affinity purified nuclei 1105 or other organelles comprised mitochondria, transcription complexes, nucleosomes, ribosomes, and other subcellular structures starting from tissues or specimen 101.

Figure 29:
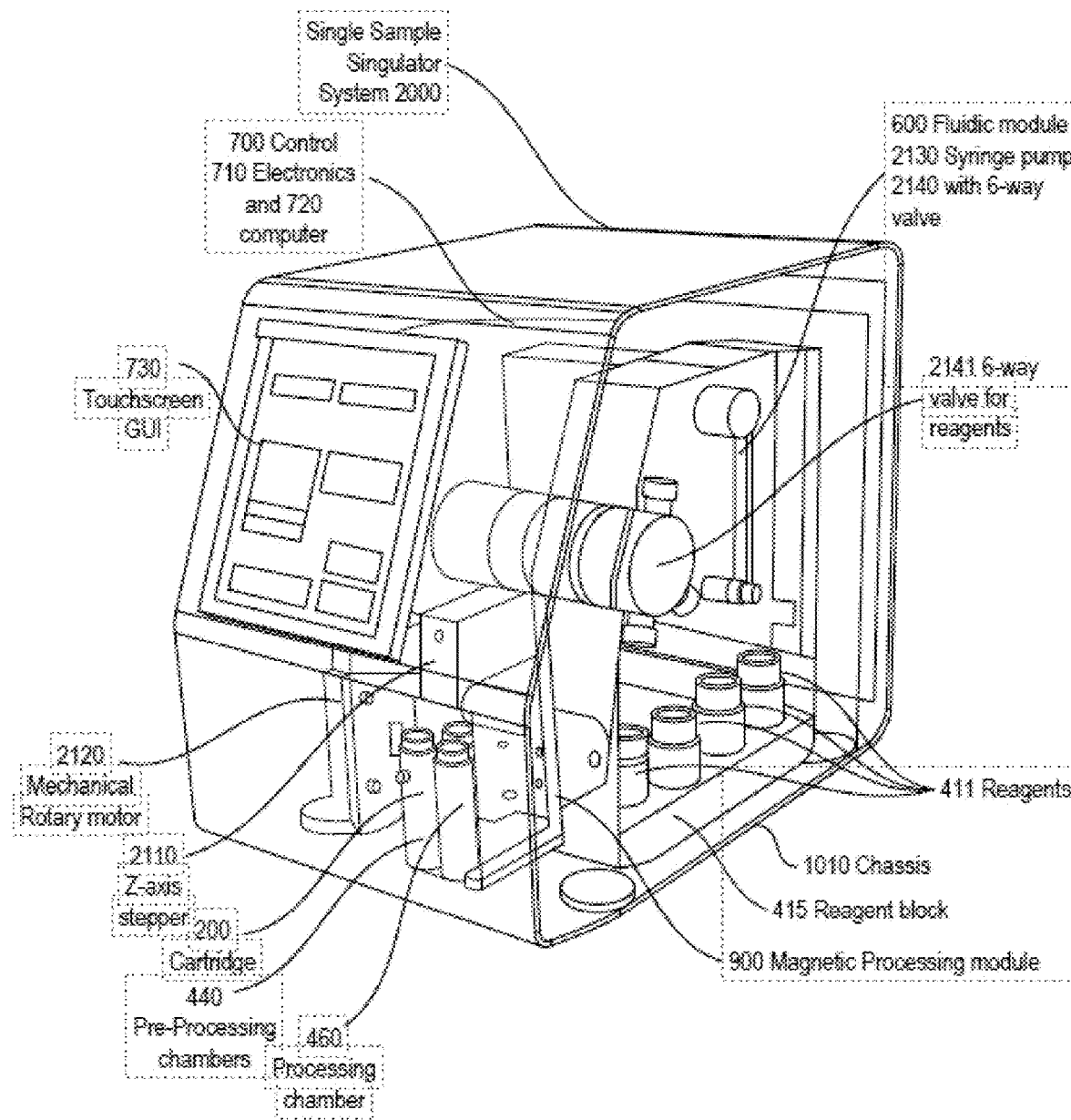
FIG. 29 shows an example of a Single-Sample Singulation System with mechanical disruption in the cartridge with a bank of enzymes and reagents on the instrument.

A 3D CAD representation of one embodiment of a Single-Sample Singulator System 2000 design packaged with a 'skin' is shown in FIG. 29. The design is based upon the AutoSingulator 2100 and has two axis mechanical motion (Z axis stepper 2110 and rotary motor 2120) integrated with fluidics based on a syringe pump with 1.6 □L resolution with a six-way valve (C2400MP, TriContinent) controlled by control software 725. A small (~16 in$^3$) OEM computer 720 with Windows 10 and 85 Gbytes HD (Beelink, AP42) can run control software 725 to control the system with display on a 10" touchscreen 730 (eleduino, Raspberry Pi10). Chassis 1010 provides the framework to mount components and the exterior of the system.

This embodiment of the Single-Sample Singulator System 2000 has one syringe pump 2130 with a six-way valve 2140 to supply liquids, pressure, or vacuum to cartridge 200. The cartridge 200 shown is similar to FIG. 18 with two Pre-Processing Chambers 440 and a single Processing Chamber 460. Cartridge valves can be pinch valves 491, which the instrument actuates, or other valves or have no valves on the cartridge 200 with all fluidic control from the instrument. A second six-way valve 2141 can access reagents (such as four digestive enzymes, magnetic beads, three buffers, two cleaning solution if two six-way valves 2140 are used) in small bottles through connecting tubing such as 1/16 ID tygon tubing or other tubing, capillaries, or fluidic lines. Actuators (not shown) can open and pinch close tubing in the cartridge 200, and operate the variable orifice 490 using variable orifice device 2150 when desired. Two strip resistive heaters or Peltiers and controllers (not shown) can set the cartridge temperature in the Pre-Processing Chamber 440 and Processing Chamber 460. A force gauge can be incorporated into the z-stage stepper 2110 to provide force-feedback control of the mechanical force on the specimen 101; this can help develop very gentle mechanical processing steps. The interface with the cartridge 200 can be standardized by the development of a cartridge adapter that will be designed with each cartridge 200 to ensure simple insertion into the system. Reagents 411 are held in a ragent block 415 which can be cooled with a Peltier to minimize degradation of reagents 411. This embodiment of the single-sample Singulator System 2000 has a Magnetic Processing Module 900.

Magnetic Processing Module.

Figure 30:
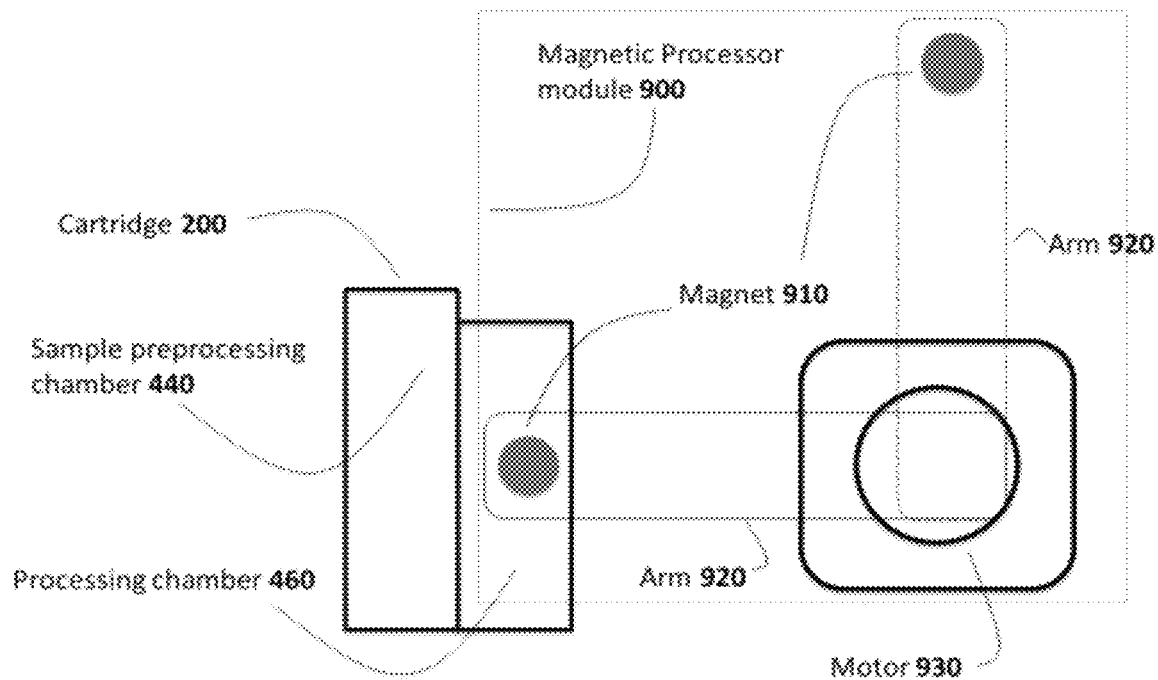
FIG. 30 shows a layout for a Magnetic Module.

Referring to FIG. 30, the Magnetic Processing module 900 can perform magnetic bead enrichment or depletion of cell types or organelles, capture nucleic acids to change buffers, and integrate downstream enzymatic workflows in Processing Chamber 460 or other locations such as in channels or tubing. Beads and wash solutions can be delivered to the Processing Chamber 460 from reagents 411 using six-way valve 2141 via a six-way valve 2140 in turn connected to syringe pump 2130. While nanoparticles stay in solution, larger beads will settle out. This can be solved by resuspension of beads, e.g., 1-30 □m beads, using a rapid mechanical vibration of the bead container.

A single-sample Magnetic Processing module 900 can have a motor 930 moving a magnet 910 such as a neodymium magnet on an arm 920 to capture paramagnetic beads inside Processing Chamber 460 when the arm is in the horizontal position as shown or release the beads when it is in the raised vertical position (shown in a dashed outline). It will be obvious to one skilled in the art that many other configurations are possible, with in some embodiments magnet 910 moving in a linear fashion, or in a circle, or other geometries. Features can be incorporated into the cartridge 200 to improve magnetic processing performance such as having a region with a smaller distal distance to increase the magnetic field locally to improve bead capture. The field of the magnet 910 can also be directed by blocking certain regions with non-magnetic materials and enhanced in other areas of the field. Sensing devices such as optical sensors or magnetic sensors can be implemented for positional feedback. Motor 930 can be controlled using Control Subsystem 700. Magnetic fields can also be produced using electromagnetic coils.

The Magnetic Processing module 900 can capture and purify cell types from eukaryotic, prokaryotics, or archea. Following creation of a single-cell suspensions, antibodies against cell surface components or other targets coupled to nanoparticles or paramagnetic beads, using standard coupling chemistries or commercially available beads with antibodies to cell surface proteins, can be added from reagents 411 by syringe pump 2130 and six-way valves 2140 and 2141 to Processing Chamber 460 containing the single-cell suspensions. Mixing can be by bubbling air through the Processing Chamber 460 or application of a 'stirring' magnetic field, or use of fluidics to agitate the single-cell suspensions and beads, or moving the sample with beads back and forth in tubing or channels, or between the two Pre-Processing Chambers 440 or other methods well known to one skilled in the art. The antibodies or other affinity agent will then bind target cells with the target antigen. The Magnetic Processing module 900 can move arm 920 to the horizontal position with magnet 910 positioned at the Processing Chamber 460. The beads with captured cells, including from a media 418 such as containing enzymes or chemicals used to dissociated specimen 101, are in turn captured by magnet 910. The media 418 can be pumped out by syringe pump 2130 and as desired captured beads can be washed to remove cell debris, enzymes, buffer, and uncaptured cells with reagents 411 or to change buffers. The Magnetic Processing module 900 can then move arm 920 to the vertical position with magnet 910 positioned away from the Processing Chamber 460 to release the beads captured by the magnetic field of magnet 910. The beads are then attached to single-cell suspensions that are now affinity purified for a desired subtype or depleted for a cell-subtype 1100. Resuspending the beads in a different buffer or media 418 is an effective way to change buffer. It will be obvious to one skilled in the art that the beads can be used to deplete cell types, debris, or other material from a cell suspension by holding the beads on the magnet and moving the now depleted fluid to a different chamber or output it to a tube or other device.

The Magnetic Processing module 900 can capture and purify nuclei 1050 or other subcellular components 1060 including organelles from eukaryotic organisms. Following creation of a suspension of nuclei 1050, antibodies against nuclear surface components, such as biotinylated anti-nuclear protein NeuN antibodies or other nuclear targets, can coupled to nanoparticles or paramagnetic beads, using standard coupling chemistries such as streptavidin nanoparticles or commercially available beads with antibodies to nuclear proteins, can be added by syringe pump 2130 to Processing Chamber 460 containing the nuclei 1050 suspension. Mixing can be by bubbling air through the Processing Chamber 460 or application of a 'stirring' magnetic field, or use of fluidics to agitate the single-cell suspensions and beads, or moving the sample with beads back and forth in tubing or channels or other methods well known to one skilled in the art. The antibodies or other affinity agent will bind nuclei 1050 or other target organelles with the target antigen(s). The Magnetic Processing module 900 can move arm 920 to the horizontal position with magnet 910 positioned at the Processing Chamber 460. The beads can then capture the nuclei 1050 bound to beads, including from a media such as containing chemicals or enzymes used to dissociated specimen 101 into nuclei 1050. The captured nuclei, now bound to the beads, can be washed to remove cell debris, enzymes, buffer, and other unbound components or to change buffers. The Magnetic Processing module 900 can then move arm 920 to the vertical position with magnet 910 positioned away from the Processing Chamber 460, which will release any beads captured in the magnetic field of magnet 910. The beads are attached to affinity purified nuclei suspensions 1105.

Figure 44:
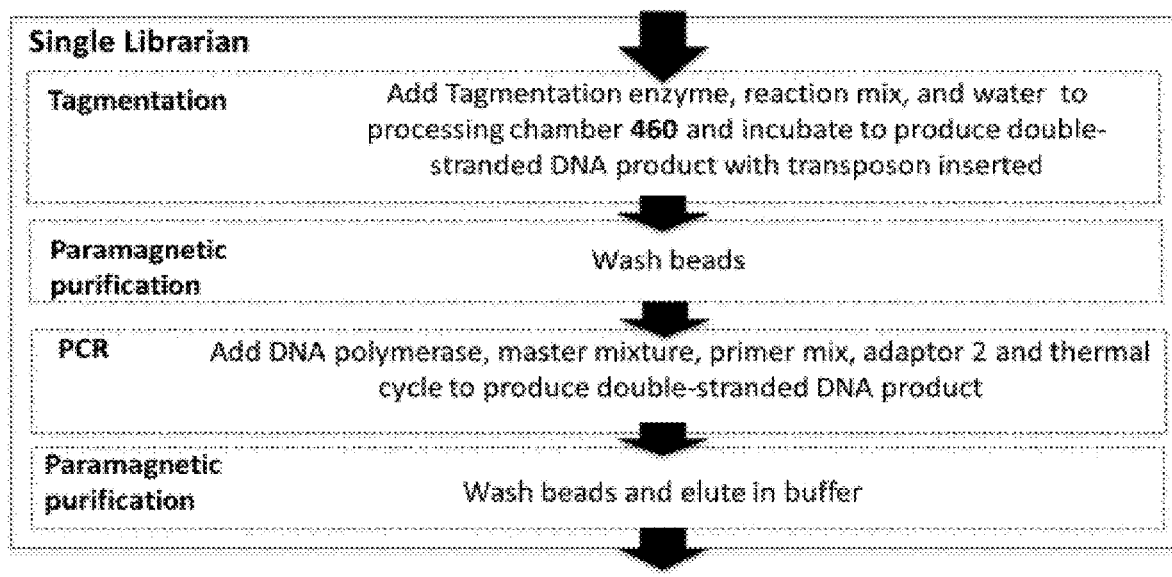
FIG. 44 shows an example of using transposons to produce a sequencing library from double stranded DNA from a specimen.

The Magnetic Processing module 900 can also be applied to process single cells 1000 or nuclei 1050 or tissue specimens 120 into nucleic acids 1072 and to further process the nucleic acids 1072 into bulk libraries. Tissue specimens can be lysed in Pre-Processing Chamber 440 by addition of chaotrophs, as described below, and the lysate can be strained through strainer 450, and moved into Processing Chamber 460. The lyzed tissue is then processed by magnetic beads to purify nucleic acids 1072. In another embodiment, the single cells 1000 or nuclei 1050 in Processing Chamber 460 are lysed by addition of chaotrophs processed with magnetic beads to purify nucleic acids 1072. In some embodiments, the purified nucleic acids 1072 are further processed into bulk libraries 1210 as described in FIGS. 44, 45, and 46 or other librarian methods well known to one skilled in the art.

Control Subsystem

The systems are controlled by a Control Subsystem 700 that uses control software 725 to control electronics 710 that actuates modules and devices. Control software 725 runs on a computer 720 which can be a standalone computer 725 or a tablet 750. The control software 725 is a rapid development software platform designed to accelerate development and commercialization. The software has support for IoT-based protocols, cloud-based protocols, Microsoft development tools and libraries, and machine learning technologies. The control software 725 Host provides a standardized scripting interface to develop, maintain, and run scripts, with a range of utilities to allow scripts to interact with the user and to interoperate with other software.

Control software 725 scripts are coded in any .Net languages and compiled to standardized DLL's; other languages are within the scope of the present invention. Once the scripting logic is developed, the scripting host layer is replaced with a dedicated executable that references the same DLL and that executes the script, dramatically shortening the development cycle.

The control software 725 Library has precompiled DLL's that provide critical functionalities including scripting interface and base libraries, support for ZMQ and other IoT libraries for intercommunication, real-time scheduling engine for autonomously optimized non-deterministic scheduling of operations, databasing, image analysis, statistical analysis, data storage, and HDF5 numerical storage libraries. Supported hardware components include: a) pumps and valves using Cavro communication protocols, b) Tecan RSP/MSP robots, c) motor controllers and I/O devices (quadrature encoders, optical sensors, etc.), d) RS232, RS485, USB HID, and other generic interface devices, e) CAN devices using the KVASER™ Communication Library, f) LabSmith pProcess devices, including micropumps, valves, and pressure sensors, and g) Arduino based devices. Control software 725 can support hardware device added and integrate overall protocols through scripting. Other software can be substituted for the control software 725.

Example of Another Preferred Embodiment of a Single-Sample Singulator System.

Figure 31:
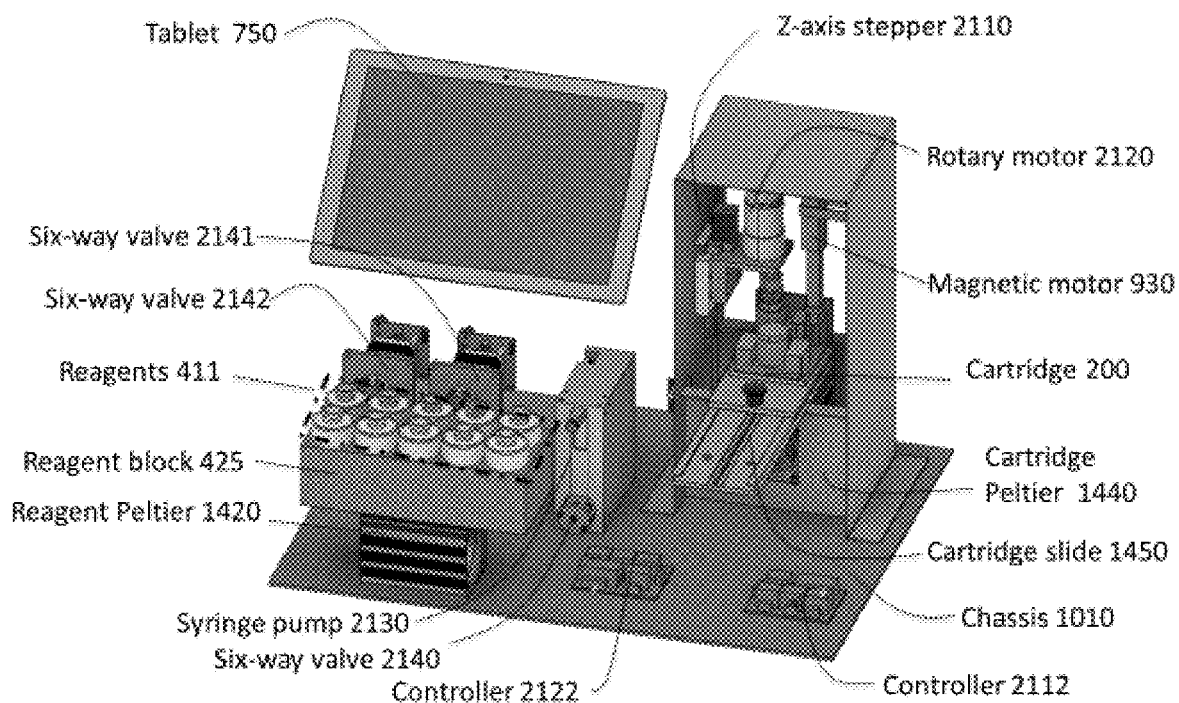
FIG. 31 shows an example of a Single-Sample Singulation System with mechanical disruption in the cartridge with a bank of enzymes and reagents on the instrument with temperature control and a cartridge insertion mechanism.

FIG. 31 shows the main functional elements of another preferred embodiment of single-sample Singulator System 2000, the enclosure, fluidic, and electrical wiring are not shown on the figure for clarity. The fluidic circuits with a cartridge 200 are shown in FIG. 34 and the electronics in FIG. 35.

Referring to FIG. 31, the main functional parts are the fluidic subsystem 600 comprised of cartridge 200 inserted on cartridge slide 1450, with temperature control by cartridge Peltier 1440, the instrument fluidics comprised of syringe pump 2130 with six-way valve 2140, two six-way valves 2141 and 2142, to access reagents 411 held in reagent block 425 with temperature regulation by reagent peltier 1420, and to connect to cartridge 200, and mechanical motion by rotary motor 2120 and z axis stepper 2110, with movement of magnet 910 by magnetic motor 930.

Example of Processing a Sample in a Cartridge Using a Single-Sample Singulator System.

Figure 34:
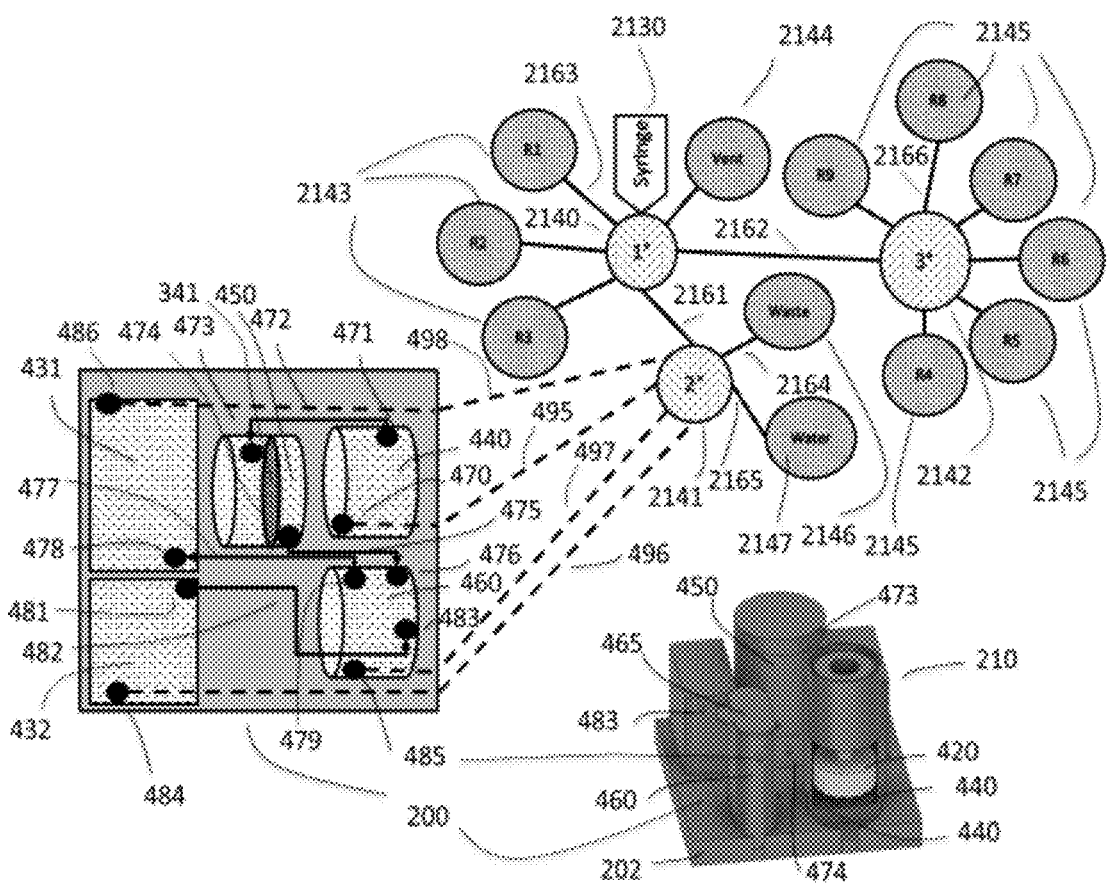
FIG. 34 shows a cartridge and how the Fluidic Subsystem delivers reagents to the cartridge.

FIG. 34 shows a design of a cartridge that incorporates a cap 210 that couples a mechanical grinder rotor 420. The cap is inserted into a Pre-Processing Chamber 440 which has a grinder stator 421 at the bottom of the chamber. The process to utilize this embodiment of cartridge 200 is as follows.

Figure 32:
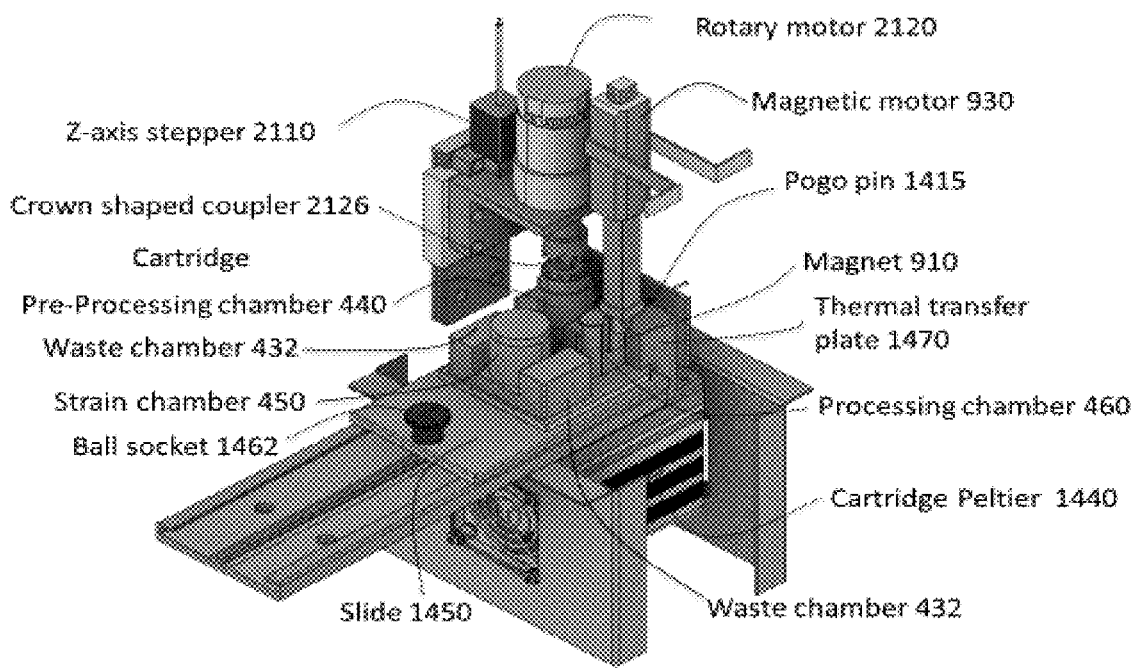
FIG. 32 shows a detail of the cartridge insertion of a Single-Sample Singulation System.

FIG. 32 shows the detail of the cartridge interface 1500 with cartridge 200 on mechanical cartridge slide 1450 in cartridge detent 1455. The operator inserts tissue specimen 120 into cartridge 200 and then cap 210 is placed on cartridge 200. In some embodiments the cap 210 is keyed to only be placed in certain orientations and can lock onto cartridge 200 permanently, preventing inadvertant spillage of tissue specimen 120 or release of material from cartridge 200 during or after processing.

In a preferred embodiment, cartridge 200 and the cartridge interface 1500 have features for 'click-in docking' to the instrument and self-aligning connections to the instrument fluidic system. In the embodiment shown in FIG. 32, cartridge 200 on cartridge slide 1450 is pushed into the instrument. Side brackets 1460 and slide 1450 align the cartridge 200. When the slide 1450 is fully inserted, a mechanism such as a retractable ball socket 1462 engages with hole and locks cartridge 200 in the proper position against thermal transfer plate 1470 and docks cartridge ports 470, 484, 485, and 486 with and spring-loaded fluidic connections 1410 such as 'pogo pins' 1415 or modular microfluidic connectors or other connectors 1417 with spring forces of, for example, 2 kg.

Figure 33:
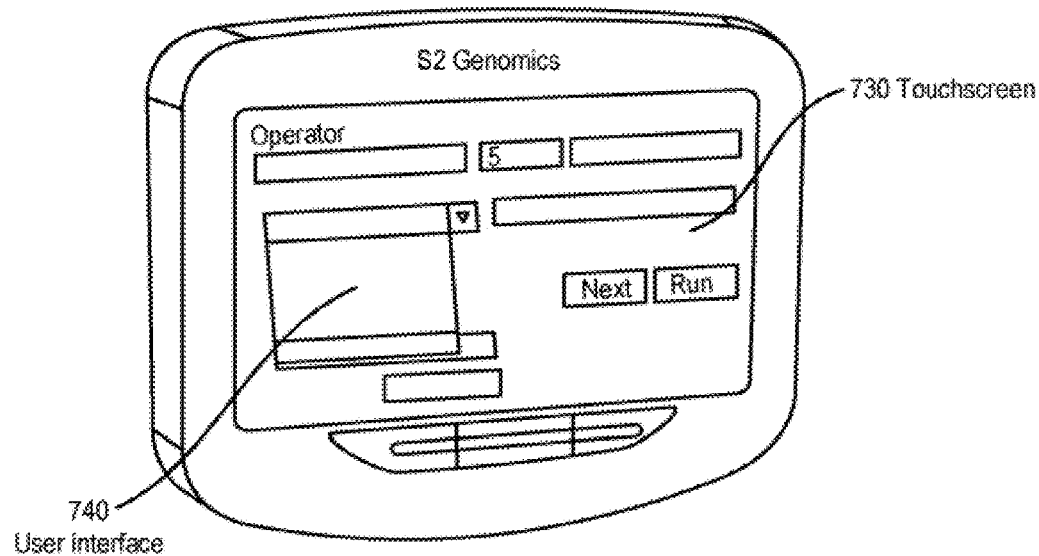
FIG. 33 is an example of a user interface for a Singulation System.

The operator can select a program to process tissue specimen 120 through user interface 740 on touchscreen 730 of tablet 750. As shown in FIG. 33, the operator can enter on user interface 740 a sample number and name, and select attributes such as the tissue type, organism (hidden behind dropdown menu), condition of tissue (e.g., normal, cancerous, degraded, etc.), and to run a pre-programmed script. Other fields can be filled automatically by the software or a LIMS system such as date, cartridge ID (from a barcode), system ID, and software version.

FIG. 33 is an illustrative example of one of many embodiments of the user interface 740. In some embodiments, the operator can adjust the processing enzymatic or chemical solution for their tissue, or the processing time, temperature, or details of the mechanical disruption, or other attributes of the preprocessing and any processing steps such as magnetic bead purifications or enzymatic reactions such as library preparation, PCR amplification, or other molecular biology, chemistry, or quality control steps. In some embodiments, Singulator System 100 can monitor the processing and adjust the processing according to rules set by the operator or preprogrammed into control software 725. Once the operator has selected the appropriate conditions and attributes for the tissue specimen 120, the operator will direct the control software 725 to run and the instrument can run automatically.

Figure 35:
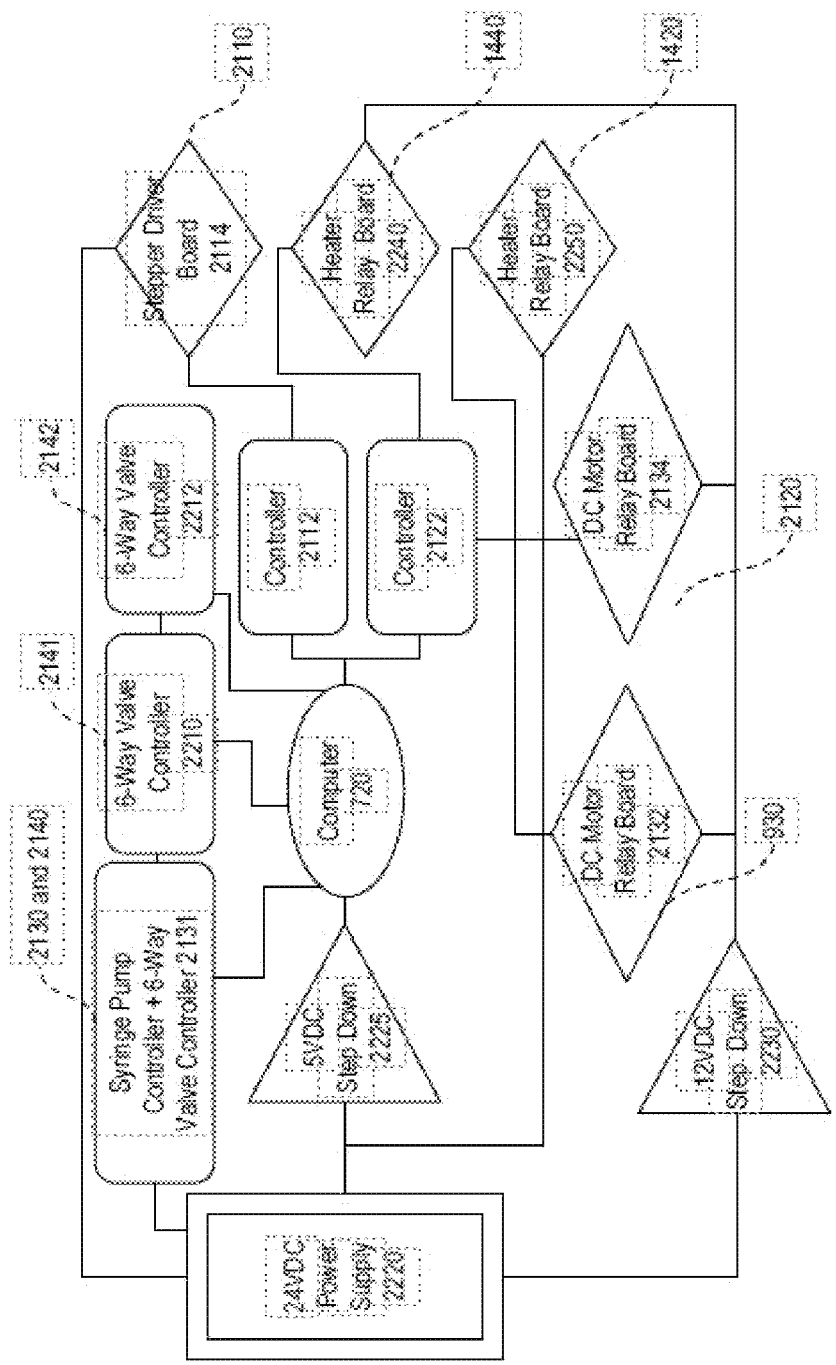
FIG. 35 shows electronics diagram and the hardware controlled by the electronics.

Referring to FIG. 35, control software 725 runs on computer 720 which in this embodiment is a tablet 750. The figure shows power lines as heavy solid lines, control lines to electronics as light lines, and the hardware devices as dashed lines. This embodiment is supplied power (shown in heavy solid lines) from 24V DC power supply 2220 which drives 5V DC step down 2225 and 12 V DC stepdown 2230 as well as stepper driver board 2114, heater relay board 2250, and syringe pump and six-way valve controller 2131 with power daisy-chained to six-way valve controller 2210 and six-way valve controller 2212. 5V DC step down 2225 powers computer 720 which in turn powers controller 2112 and controller 2122. 12 V DC stepdown 2230 powers DC motor board relay board 2132, DC motor board relay board 2134, and heater relay board 2240.

Computer 720 controls all devices. It has direct connections to syringe pump and six-way valve controller 2131 which in turn controls syringe pump 2130 and six-way valve 2140; six-way valve controller 2210 which in turn controls six-way valve 2141, and six-way valve controller 2212 which in turn controls six-way valve 2142. Computer 720 connects to controller 2112 (control line not shown) which controls stepper driver board 2114 which in turn drives z-axis stepper 2110. Computer 720 connects to controller 2114 (control line not shown) which controls DC motor relay board 2132 which drives magnetic motor 930, DC motor relay board 2134 which drives rotary motor 2120, heater relay board 2250 which drives reagent Peltier 1420, and heater relay board 2240 which drives cartridge Peltier 1440. Many other embodiments are within the scope of the invention and are obvious to one skilled in the art.

Referring to FIG. 34, enzymatic or chemical dissolution solution 410 is delivered to Pre-Processing Chamber 440 from the appropriate reagent reservoir 2143 for example R1 through tubing 2163, six-way valve 2140 using syringe pump 2130 through tubing 261 connected to six-way valve 2141 to line 495 to reagent addition port 470 on cartridge 200. The temperature of cartridge 200 is controlled by cartridge Peltier 1440 by tablet 750. The temperature of Pre-Processing Chambers 440 may be set to 37° C. for processing tissue specimens 120 into cells and 4° C. to process tissue specimens 120 into nuclei 1050 or other temperatures as the operator desires.

Figure 36:
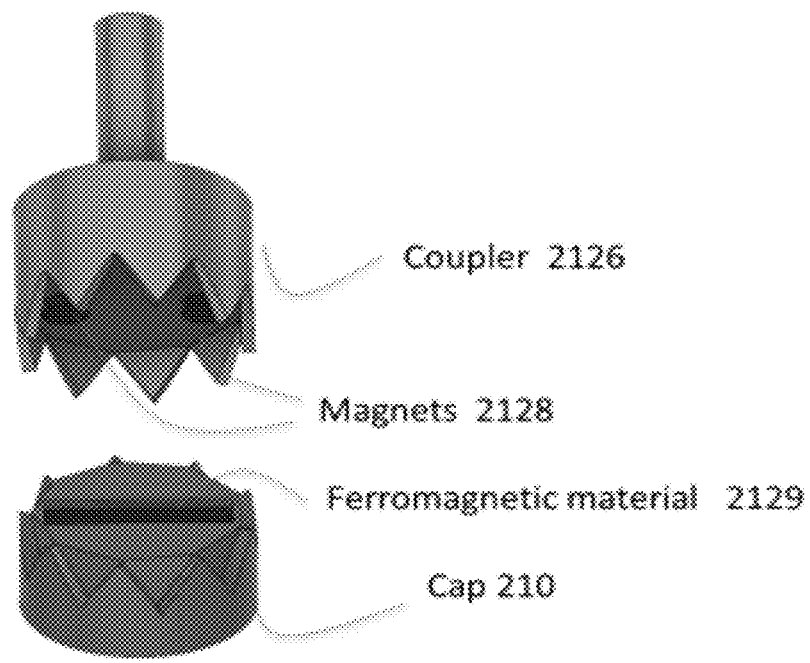
FIG. 36 illustrates an example of a cartridge cap and means of coupling to the instrument.

Using Z-axis stepper 2110, rotary motor coupler 2125 is lowered until it engages with cap 210. In some embodiments the engagement is using a locking mechanism such as a crown shaped coupler 2126 shown in FIG. 36. In a preferred embodiment two magnets 2128 are located on rotary motor coupler 2126 and two magnets or a bar of ferromagnetic material 2129 on cap 210 is attracted; this embodiments rotationally aligns cap 210 and rotary motor coupler 2126. In another embodiment rotary motor coupler 2126 has a single embedded permanent magnet 2128 which attracts a magnet or ferromagnetic material 2129 including iron, nickel, cobalt, or other materials. In some embodiments this attraction is used to raise grinder rotor 420 after it has been depressed. In other embodiments, cap 210 has a spring inside the cap to raise grinder rotor 420 when desired when Z-axis stepper 2110 is raised. Other mechanism such as using a hex shaped coupler with a matching hexagon receptor on cap 210 with a spring load, or a gripping chuck, or many other configurations are possible without limitation.

When the cap 210 has been engaged by the rotary motor coupler 2125 and the appropriate enzymatic or chemical dissolution solution 410 has been delivered to Pre-Processing Chamber 440, Z-axis stepper 2110 can move rotary grinder 420 down. In some embodiments a force sensor monitors the force used to move rotary grinder 420 down to ascertain when tissue specimen 120 is encountered. In some embodiments rotary motor 2120 is rotating as Z-axis stepper 2110 is lowered and the current draw is monitored to to ascertain when tissue specimen 120 is encountered. In other embodiment, rotary grinder 2120 is moved to a position without any force feedback. Rotary motor 2120 can be actuated and the tissue disrupted according to the desired program for the tissue.

The program may include many variations of moving in one direction, then reversing direction. In some versions, the grinder may move downward during the grinding and then move upwards to relieve pressure on the tissue. In some embodiments rotary grinder 420 can be rotated at slow speeds such as 25, 50, or 75 rpm or slower; in other embodiments at speeds such as 100, 200, 500, or 1,000 rpm or more. The speed of the rotation can be changed or the direction reversed and the position controlled by Z-axis stepper 2110. In other embodiments, cartridge 200 has a plunger, variable orifice, pestle or other mechanical disruption device.

The Pre-Processing chamber 440 can be temperature controlled by thermal transfer plate 1470 which is controlled by cartridge Peltier 1440. In many cell singulation protocols, the tissue is incubated at 37° C. for 30 min and for many nuclei 1050 protocols, the tissue is incubated at 4° C. The system can accommodate a wide range of temperatures, incubation times, and mechanical disruption protocols.

Referring to FIG. 34, after mechanical and enzymatic disruption, the rotary grinder 420 can be moved to the bottom of Pre-Processing Chamber 440 which displaces the now dissociated tissue specimen 120 to the level of outlet port 471. Vacuum can be applied to waste chamber 431 using syringe pump 2130 through six-way valve 2140 and line 2161 through six-way valve 2141 and line 498 to upper port 486 of waste chamber 431 of cartridge 200; the vacuum in waste chamber 431 pulls through line 477 connected to port 478 and port 479 to Processing Chamber 460 and line 475 connected to port 476 and port 474 on strainer 450, through line 472 connected to outlet port 471 and port 473 to pull the now dissociated tissue specimen 120 through line 472 into strain chamber 450 and through a filter 341, such as a 70 □m or a 50 □m or 30 □m or other filter, to remove clumps of cells 1000, nuclei 1050, or debris. The filtered sample is then pulled by the vacuum through port 474 and line 475 and port 476 into Processing Chamber 460. The amount of vacuum can be minimized to lessen shearing by filter 341 if desired. For the production of single cells 1000 and nuclei 1050, the user can remove Processing Chamber cap 465 and pipette out the processed sample.

Waste chambers 431 and 432 are designed to be connected to the top and the bottom of Processing Chamber 460 respectively. This allows waste chamber 432 to withdraw liquid from the bottom of Processing Chamber 460 when vacuum is applied while waste chamber 431 will not withdraw liquid from Processing Chamber 460 in most circumstances. Waste chambers 431 and 432 can optionally contain a liquid absorbent or solid absorbent.

In some instances, the operator will have selected a program that further processes the dissociated tissue specimen 120 in Processing Chamber 460. For example, the sample can be further processed by magnetic processing with the Magnetic Processing Module 900. For cells, antibodies to capture specific cell types coupled to magnetic beads or particles can be added to Processing Chamber 460 by syringe pump 2130 from a reagent reservoir such as magnetic beads in 2145 R8 through line 2166 and six-way valve 2142 through line 2162 and six-way valve 2140 to line 2161 to six-way valve 2141 and line 497 to reagent addition port 485 on Processing Chamber 460. The beads and cells can be mixed by moving them back and forth in line 475 into the bottom of strain chamber 450 by applying vacuum or pressure through lines 472 and 495 and 2161 using syringe pump 2130 and six-way valves 2141 and 2140. After mixing and incubation for the desired time, the specific cells for the antibodies attached to the magnetic beads can be collected by using Magnetic Processing module 900 to move magnet 910 close to Processing Chamber 460, such as within 1 mm, or 5 mm, or 1 cm, and waiting for 1 min, or 2 min, or 5 min or other times. The magnetic beads are captured on the side of Processing Chamber 460 or in a line such as 475. The uncaptured cells in the enzymatic or chemical dissolution solution 410 can be then removed by applying vacuum to the lower port 483 on processing chamber 460 through line 482 to port 481 on waste chamber 432 by using port 484 and line 496 through six-way valve 2141 and line 2161 and six-way valve 2140 with syringe pump 2130. The desired buffer can then be added from a reagent reservoir such as 2145 R7 through port 485 and line 497 and the magnet 910 moved away from Processing Chamber 460. The cells can be resuspended by again mixing in line 475 as described. Additional cycles of wash can be applied when desired. The purified cells attached to the magnetic beads through the antibodies or other affinity reagents can then be removed through Processing Chamber cap 465.

It will be obvious to one skilled in the art that many variations of magnetic bead processing can be used including depletion of types of cells, removal of cellular debris or tissue debris, capture of nuclei 1050 or subcellular components 1060, processing of nucleic acids 1072, or other biomolecules 1070. Other processes can also be performed in Processing Chamber 460 such as library preparation or other reactions as described herein.

Example Using a Vertical Cartridge in the Singulator System.

Figure 37:
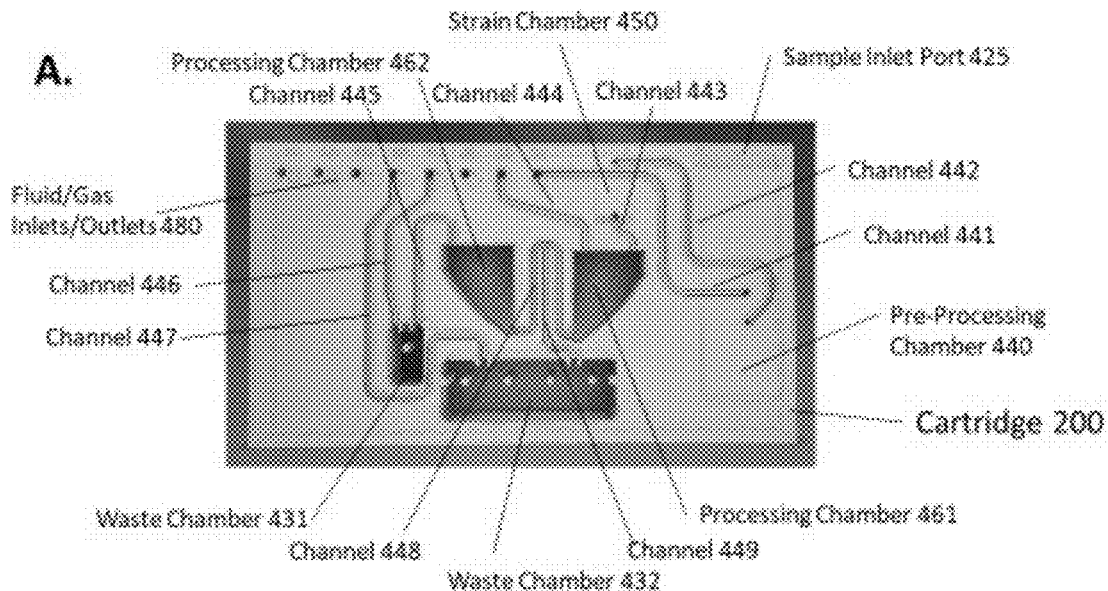
FIGS. 37A-C shows an example of a vertical cartridge that integrates processing of tissue.
Figure 37:
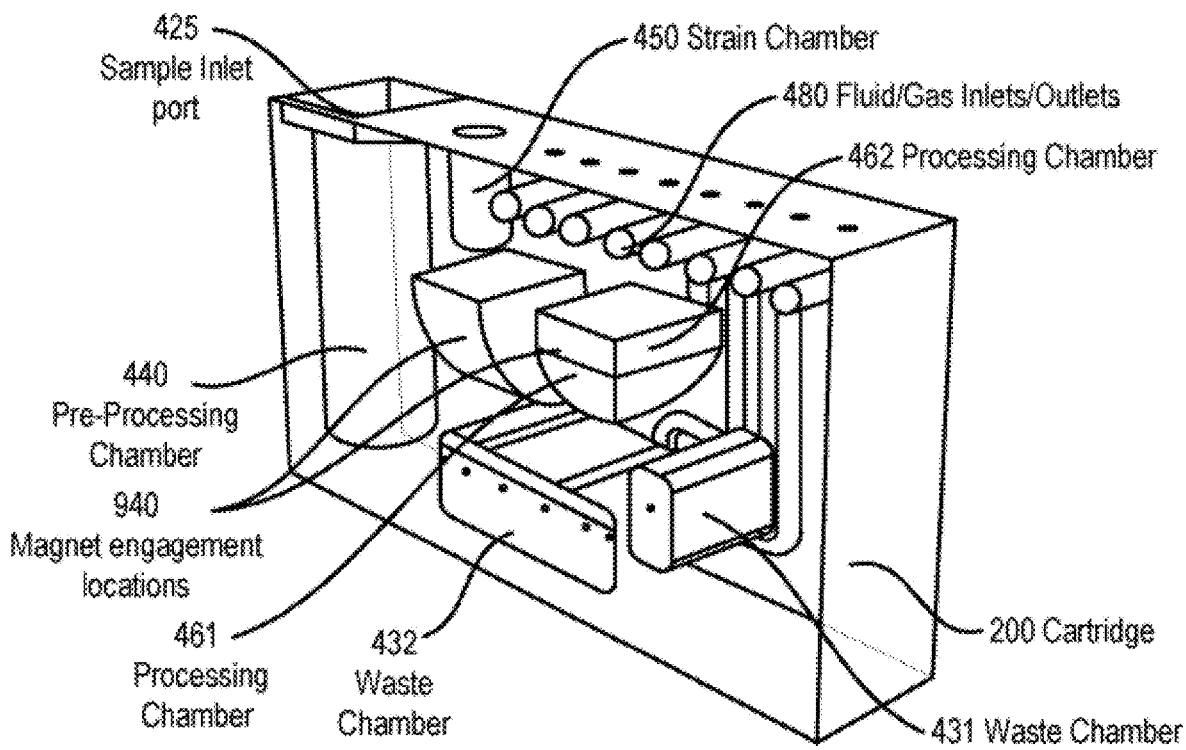
Figure 37C:
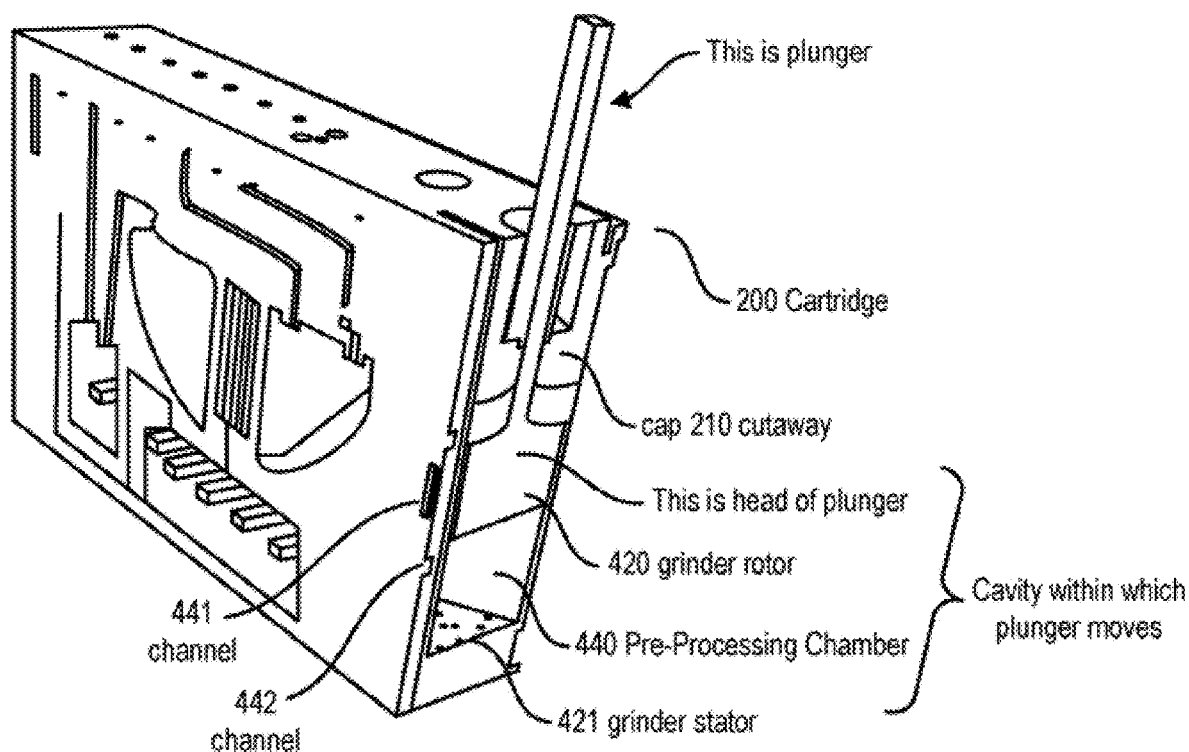

Another preferred embodiment of cartridge 200 is shown in FIGS. 37 A-C. This vertical cartridge 200 is designed to be injection molded and then sealed with a material such as a heat sealable plastic or laser welded, ultrasonically welded or other means to seal cartridge 200. It has two chambers for processing samples which facilitates improved mixing during processing steps.

Referring to FIGS. 37 A-C, a typical Process Flow is as follows. The operator inserts tissue specimen 120 into the Pre-Processing Chambers 440 through sample inlet port 425 and places cap 210 (not shown) onto cartridge 200 and inserts cartridge 200 into the Singulator System 100, Tissue Processing System 80, or Sample Processing System 50 as described above. After selection of the appropriate program, the instrument makes the mechanical connection to cap 210 through rotary motor coupler 2125 and fluid/gas connections to the Fluid/Gas Inlets/Outlets 480. The instrument also contacts the Pre-Processing Chambers 440 and the two Processing Chambers 441 and 442 from the back of cartridge 200 with elements such as cartridge Peltier 1440 which can heat or cool said fluid chambers.

Enzymatic or chemical dissolution solution 410 is injected into the Pre-Processing Chamber 440 through the fluid channel 441. The solution may be heated or cooled by the action of the temperature regulation elements engaged with Pre-Processing Chamber 440. The enzymatic or chemical dissolution solution 410 can contain enzymes or chemicals to help dissociate the tissue specimen 120 or convert cells to nuclei 1050. The grinder rotor 420 is then mechanically rotated and brought up/down by the Singulator System 100 whereby tissue specimen 120 is separated into smaller and smaller pieces by the action of the grinding features on the grinder rotor 420 and grinder stator 421 Single cell 1000 or nuclei 1050 production is achieved by the combined action of the grinding elements and incubation/exposure of the tissue specimen 120 to reagents 411, e.g., enzymes, or chemicals, or combinations of enzymes and chemicals as described herein. After the tissue disruption is sufficiently advanced, the grinder rotor 420 is brought completely down until it touches the grinder stator 421 whereby the singulated cells 1000 or nuclei 1050 in the enzymatic or chemical dissolution solution 410 are pushed around and above the grinder rotor 420.

All the Fluid/Gas Inlets/Outlets 480 are then sealed and the singulated cells 1000 or nuclei 1050 suspension, or nucleic acids 1072 are pulled from the Pre-Processing Chambers 440 through channel 442 to Strain Chamber 450 and then through channel 443 into the Processing Chamber 461 by applying negative pressure through channels 446 or 444. A filter 431 in Strain Chamber 450 prevents undissociated tissue, cell aggregates, and debris from entering the Processing Chamber 461. Waste Chamber 431 can containing a liquid absorbent or solid absorbent to prevent any liquid from exiting through the Fluid/Gas Inlets/Outlets 480 and into the Singulator System 100.

If desired, the single cell 1000 or nuclei 1050 suspension or other prepared tissue specimen 120 can then be mixed through Channel 448 by applying alternative negative (and or positive) pressure to channels 444 and 445 to move the sample back and forth from Processing Chamber 461 to Processing Chamber 462. If no further processing is desired, the operator can pull out the single cell 1000 or nuclei 1050 suspension or other processed sample through an opening or processing chamber cap 465 (not shown) in the top wall of Processing Chamber 461 or Processing Chamber 462.

For the positive selection or depletion of specific cell types, or nuclei 1050, or subcellular components 1060, or biomolecules 1070, or for washing the cells and/or for exchanging the buffer, the single cell 1000 or nuclei 1050 suspensions can be further processed by using cell-specific, or nuclei-specific, or other affinity reagents coupled to magnetic beads or using paramagnetic bead purification of nucleic acids 1072 or other methods. For example, cell-type specific or nuclei-specific, or other affinity magnetic beads and reaction solutions are injected through Channel 444 into Processing Chamber 461. The beads are incubated with the single cell 1000 or nuclei 1050 suspension by mixing though channel 448 as described above, whereby the magnetic beads bind to their target cells. Then, magnet(s) 910 is/are applied to the backside of Processing Chambers 461 and/or 462 depending where the sample is moved to, whereby the magnetic beads (and attached cells or nuclei or other biocomponents) are attracted to and held at the Processing Chamber 461 or 462 wall(s). The single cell 1000 or nuclei 1050 solution now depleted of specific targets is pulled into Processing Chamber 461 by applying negative pressure to channel 444 (and/or positive pressure to channels 445 and 446 and then sequentially into the Waste Chamber 432 containing a liquid or solid absorbent substance by applying a negative pressure through channels 447 and 449.

Simultaneously or subsequently, washing solution can be injected through channel 444 and the beads attached to magnet 910 can be washed with a wash buffer by combinations of mixing, magnetic release/application and pulling liquid to the Waste Chamber 432. This process can be repeated one or more times. Similar processing can also be used to resuspend the single cells 1000 or nuclei 1050 in a specific buffer or growth solution.

After the single cells 1000 or nuclei 1050 are in the desired output buffer, the magnet 910 is released, the cells homogeneously resuspended by mixing in channel 448, and then the single cell 1000 or nuclei 1050 suspension is pulled either into Processing Chamber 461 or 462. The operator can then pull out the single cell 1000 or nuclei 1050 suspension through an opening in the top wall of Processing Chamber 461 or 462 covered by a foil-seal, or septum, or processing chamber cap 465 or other mechanism (not shown). Other processing/reaction/fluidic elements can be added to the cartridge as desired to enable additional processing modes in including without limitation tangential flow filtration, optical interrogation, library preparation, and nucleic acid purification.

Four-Sample Singulator System

A Four-Sample Singulator System 2400 is shown in FIG. 27 bottom right. Tissue specimens 120 are loaded into any of four cartridges 200, the appropriate program selected on the touchscreen 730 graphical user interface 740, and the system executes the appropriate workflow for the tissue and genomic application. The core of the Four-Sample Singulator System 2400 can be the Single-Sample Singulator System 2000, expanded to accept four cartridges. The expansion can be comprised of the addition of cartridge interface assemblies with cartridge Peltier 1440, fluidic connections, a Z-axis stepper 2110, rotary motor 2120, a six-way valve 2142, control boards, and other components for each additional cartridge added. In one embodiment one or up to four cartridges 200 can be run at the same time with the same or different programs.

Enhanced Singulator System

Figure 38:
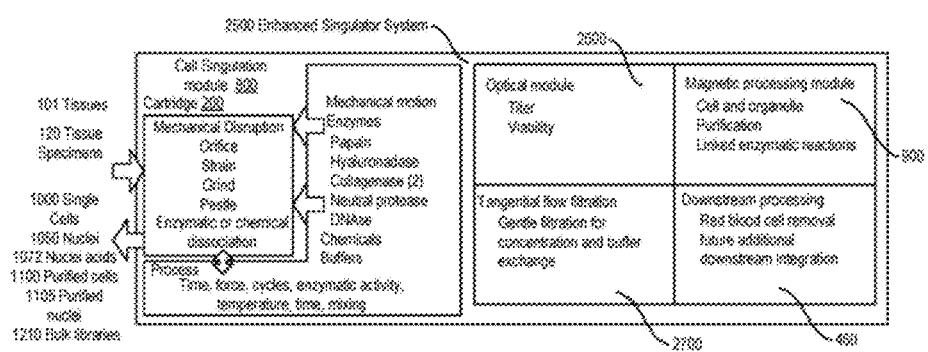
FIG. 38 shows the modules in an Enhanced Singulator System.
Figure 38:
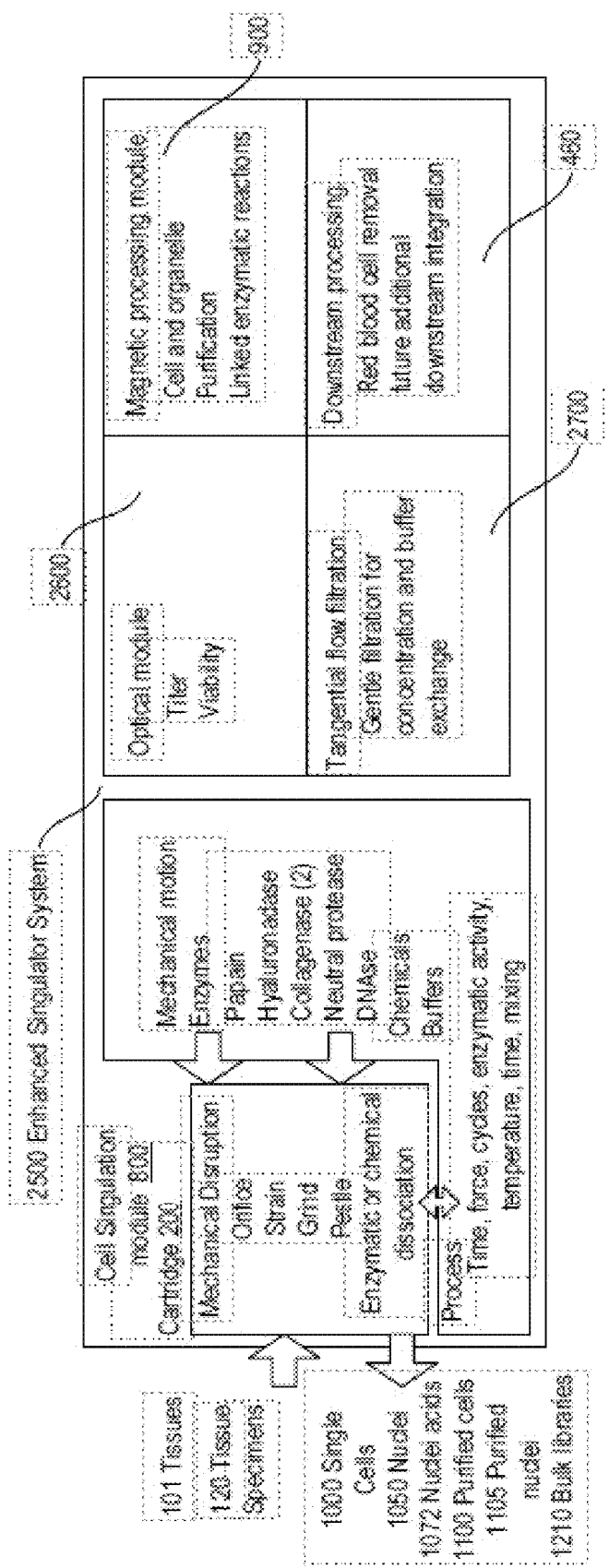

The workflow of the Singulator System 100 can be extended downstream in an Enhanced Singulator System 2500 as shown in FIG. 38 and additional processing capabilities added to integrate and simplify the workflows for genomics and other applications for operators. An optical module 2600 can be added to determine titer and viability. A tangential flow filtration module 2700 can be added to replace the enzymatic mixture with a buffer of choice at a volume to produce the proper titer and buffer for downstream processes. Downstream processing in the Processing Chamber 460 can be extended to lyse red blood cells and perform chemistries such bulk library preparation. Many other modules and applications can be added.

Optical Module

The determination of the viability and number of cells is critical to produce titered cell suspensions 1300 automatically for downstream processing without further intervention. Currently, after cells are prepared from tissue, separate instruments are used to count the number of cells and viability, e.g., FACS, a cell counter, or a microscope, and centrifugation to wash and concentrate the cells, or FACS to select certain cell types and remove debris.

An optical module 2600 can be incorporated into an Enhanced Singulator System 2500 to interrogate samples for titer, viability, and process control to potentially produce less stressed cells. The viability determination can be performed using bright-field illumination with an added stain, e.g., Trypan Blue, or with fluorescence live/dead stains such as SYTOX Green or others. Viability staining can be detrimental to the viability of the cells, interfere with downstream labeling, or require optical quality cartridges.

Figure 39:
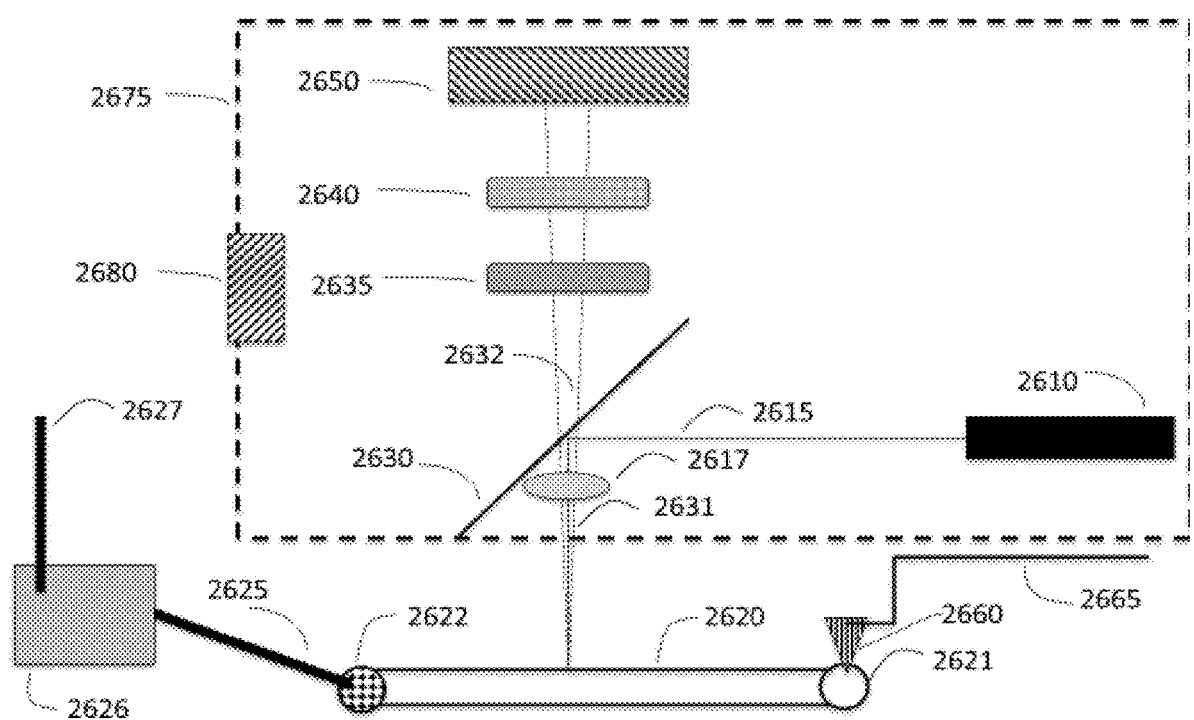
FIG. 39 is an illustration of a flowcell and optical module.

Referring to FIG. 39, a preferred embodiment is to take a small aliquot, such as 10 to 50 μL, from a port in the cartridge 200, such as the Processing chamber cap 465, with a pipettor 2660 on a two-axis stage 2665, move the pipettor 2660 to flowcell 2620, and dispense the sample into reservoir 2621 and then the pipettor 2660 picks up and adds the appropriate dye, e.g., Trypan Blue, or other, and optionally uses pipettor 2660 to mix the aliquot with the dye in reservoir 2621 by pipetting up and down. In some embodiments no dye is used.

The mixed aliquot and dye is then moved into the flowcell 2620 by applying vacuum on line 2627 through waste container 2626 and line 2625 and connector 2622 to pull the mixed aliquot and dye into flowcell 2620. Alternatively, the dimensions of the flowcell 2620 may sufficiently small for the mixed aliquot and dye to be pulled in by capillary action with the aliquot and dye can be premixed in the pipettor 2660 or other place. In another embodiment, pipettor 2660 can seal at the end of reservoir 2621 to push the mixed aliquot and dye into flowcell 2620. Many other methods of moving the aliquot are envisioned and within the scope of the present invention including pneumatic pumps, peristalic pumps, electrokinetic pumps, mechanical pumps, and other pumps located on or off the device, as well as many other ways to move the aliquot. The mixed aliquot and dye in flowcell 2620 can then be interrogated by an optical imaging device 2675 to measure brightfield or fluorescence or other images of the cells or nuclei in flowcell 2620.

In one embodiment, as shown in FIG. 39, a 'staring' epifluorescent imager 2675 interrogates flowcell 2620. A light source 2610, comprised of LED, lasers, laser diodes, halogen lamps, or other light sources, outputs beam 2615 which is reflected by beam-splitter 2630 and focused by lens 2617 to illuminate the sample in flowcell 2620. Emitted fluorescent signal 2631 passes through lens 2617 and hits beamsplitter 2630 which will allow the longer wavelength fluorescence to pass through creating fluorescent signal 2632, which in turn can pass through laser-line blocker 2635 and optical filter 2640 before reaching detector 2650. Detector 2650 can have many different embodiments comprised of CCD cameras, preferrably with greater than 10 megapixels, photomultiplier tubes, avalanche photodiodes, photodiodes, CMOS detectors, or other sensors. In a preferred embodiment, detector 2650 has an array of detection sensor elements to form pixels of image. In some embodiments, imager 2675 can stare without moving, and in other embodiments part of the imager 2675 may physically move to scan the flowcell 2620 such as a flying head imager, or a galvoscanner, or other implementations well known to one skilled in the art. The optical path can be adapted to the light source 2610 and in some embodiments will use a diffuse beam without a beamsplitter for brightfield illumination. In some embodiments, confocal imaging can be used to improve signal-to-noise. In some embodiments, multiple detectors, beamsplitters, and filter sets are used to separate different wavelengths of light or otherwise process the light.

In a preferred embodiment, the flowcell 2620 geometry is made from optical glass with a 100 μm channel. In other embodiments, arrays of fluidic channels are used in flowcell 2620 to allow multiple aliquots to be detected. In some embodiments, one or more glass capillaries with burned windows are used as flowcell 2620. In some embodiment, pipettor 2660 and two axis robot 2665 are replaced with fluidic plumbing to deliver the aliquot to reservoir 2621.

In some embodiments, the imager 2675 and detector 2650 can be autofocused with flowcell 2620. In one embodiment, the autofocusing moves imager 2675 and detector 2650 using motor 2680 to move in small increments, e.g., less than 1 μm, less than 2 μm, less than 5 μm, less than 10 μm, less than 20 μm, less than 25 μm, less than 50 μm, or less than 100 μm to focus on features on flowcell 2620 or the Raman line of water in flowcell 2620 or other features. The features may be the top or bottom surface of the flowcell 2620 or may be features designed into flowcell 2620 to simplify focusing such as a grid of lines or 3-D features. Software interprets the images to determine the focal plane for best resolution. In another embodiment, the detector 2650 and the flowcell 2620 are rigidly fixed optically to place flowcell 2620 always in the plane of focus.

After the mixed aliquot with dye has been interrogated by imager 2675, in one embodiment, the mixed aliquot and dye is then moved into waste container 2626 by applying vacuum on line 2627 through waste container 2626, line 2625, and connector 2622 to pull the mixed aliquot and dye from flowcell 2620 into waste container 2626. The flowcell 2620 is then cleaned for reuse, such as by having pipettor 2660 pipetting cleaning solutions, such as 100 mM NaOH followed by 10 mM Tris HCl, pH 7 followed by deionized water into reservoir 2621 and after a suitable incubation time, pulling the cleaning solution into waste 2626 as described. Many other cleaning protocols are within the scope of the invention.

Camera control and image acquisition can be based on Point Grey/FLIR Spinnaker SDK optimized for machine vision applications or other image processing software such as Image J freeware, Cell Profiler, or other software. The output of the imaging device 2675 can be processed in software to quantify total number of viable cells and non-viable cells or to detect subcellular components 1060 and nuclei 1050 or quantify biomolecules 1070 such as nucleic acids 1072. In some embodiments, chemicals or biologicals can be added to the aliquot to allow measurement of their impact on freshly produced cells 1000 or nuclei 1050 or other cellular components. In some embodiments, with two or more fluidic channels, chemicals or biologicals can be added to one or more of two or more identical aliquots but not to another aliquot which can serve as the control. In some embodiments, the single cells 1000 can be imaged and genetically modified such as with CRISPR and the cells collected for subsequent usage.

Monitoring of cell titer and viability at intervals will enable the Singulator System 100 to adjust the mechanical or enzymatic regime to gentler or harsher enzymatic and mechanical conditions as needed for a tissue that dissociates easier than expected or harder. For example, cancerous tissues have different properties than normal tissues and may need individual adjustment and optimization of disruption conditions for best results. Singulator System 100 can process images from imager 2675 with Control Subsystem 700 control software 725 to monitor the tissue dissociation rate by the number of cells or cellular components produced per time interval. When applicable, the operator or control software 725 can increase or decrease the mechanical disruption or the enzymatic or chemical formulation changed to stronger or weaker solutions.

Tangential Flow Filtration Module.

The production of titered single cells for direct processing by single cell DNA sequencing or scRNA-Seq can simplify the tasks for the genomic scientist. The optical module 2600 can measure the number and viability of the single cells and the single cell 1000 or nuclei 1050 suspensions can be adjusted for titer, typically by dilution. In the lab, the workflow involves centrifugation, washing, and resuspension to replace the buffer and remove debris, or by FACS sorting. In a fluidic device accomplishing this can be done using magnetic bead processing or filtration; however, 'dead-end' filtration is prone to clogging, can shear cells, and recovery of filtered cells can be problematic. These problems have been solved in the biopharmaceutical industry by using tangential flow filtration (TFF).

Figure 40:
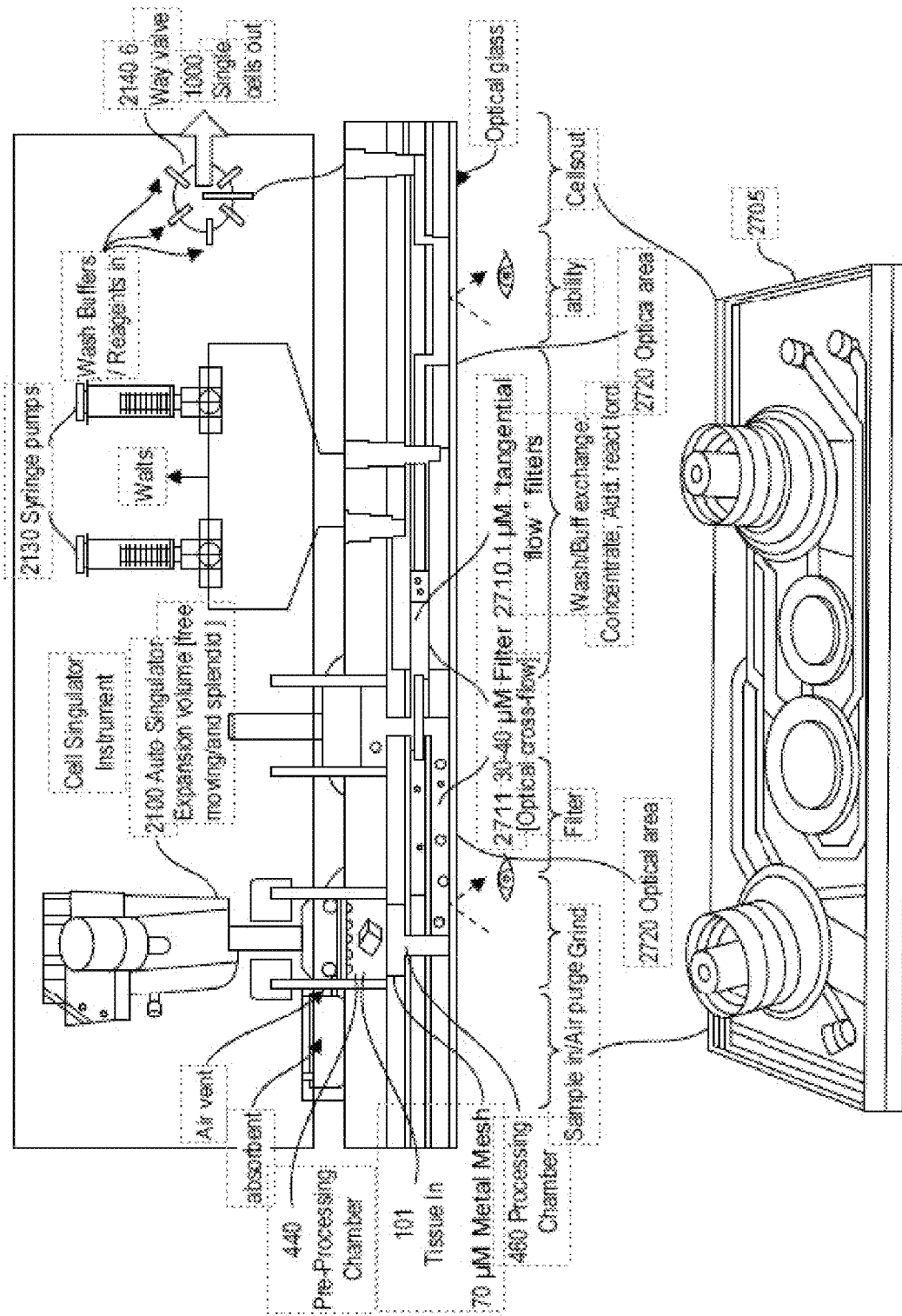
FIG. 40 shows a five layer cartridge designed to integrate multiple functions into one cartridge.

In one embodiment, referring to FIG. 40, a five-layer cartridge 2705 with full process integration was designed. This cartridge is laser cut from acrylic, and assembled with pressure-sensitive adhesive (ARcare 90445) with embedded tangential flow filters 2710 and strainer filter 2711. The layered cartridge, and similar ones designed only to test TFF, can be assembled a variety of tangential flow filters 2710 (e.g., 0.8 □m Durapore, 5 □m Durapore, Isopore, Fluoropore). The five-layer cartridge 2705 also has optical areas 2720 to interrogate the viability and titer of the single-cell 1000 or nuclei 1050 suspension in the cartridge 2705 at different parts of the workflow. The cells are gently moved tangential to the filters by a syringe plunger or other method connected to the AutoSingulator 2100 while buffers are circulated on the opposing side of the tangential flow filters 2710 by syringe pumps 2130.

TFF can be incorporated in many embodiments of cartridges 200 in the Processing Chamber 460 to add the ability to concentrate cell suspensions, remove debris, and change buffers. The implementation is an interplay between cartridge design and the on-instrument process development. Cartridge 200 can be designed to incorporate parallel filters into the molding process, routinely done for syringe filters. The Enhanced Singulator System 2500 can seal the cartridge 200 and provide the circulation of buffer driven by pumps comprised of peristaltic pumps, micropumps (e.g., TCS Micropumps), or others directed by control software 725. The TFF module can be incorporated in many cartridge 200 designs and with many embodiments of the Sample Processing System 50, Tissue Processing System 80, or the Singulator System 100.

Downstream Processing: Red Blood Cell Lysis.

The Enhanced Singulator System 2500 has the capability to perform additional biochemistry after single cells 1000, nuclei 1050, or biomolecules 1070 have been produced or purified. Syringe pump 2130 can deliver reagents to the Preprocessing Chamber 440 or Processing Chamber 460 of the cartridge 200 which enables multiple process options.

In many procedures, red blood cells (RBC) are present in high titer in the starting tissue and need to be removed by perfusion or later by lysis. Red blood cell lysis can be added as an option to the workflow after production of single-cell suspensions 1000 or purified single-cell suspensions 1100 or other outputs as follows. RBC lysis solution (e.g., 0.5% ammonium chloride or commercially available solutions) is moved by syringe pump 2130 into Processing Chamber 460 and mixed with the single-cell 1000 in suspensions by methods such as bubbling, fluid flow, magnetic stirring, or other methods, and the lysis solution and the single-cell 1000 suspensions incubated for five minutes or less at room temperature or other temperatures. The time course and temperature can be optimized to adjust parameters to conditions that favor high viability for the tissue specimen 120 with the requirements of the RBC lysis. After lysis, the RBC lysis solution can be removed or diluted to protect the other cell types either by TFF processing or rapid dilution with buffer.

Single Librarian Embodiment

The Enhanced Singulator System 2500 embodiment can be extended to create a Single Librarian 3000 embodiment with integrated optical analysis to determine viability and titer, tangential flow filtration to wash cells or nuclei to replace the buffer and adjust the titer, magnetic processing to capture nucleic acids and integrate pooled library enzymatic steps, and integration of single-cell/nuclei nanodroplet or nanobolus processing and library preparation. Real-time titer and viability data enables adapting tissue processing reagents and mechanical disruption in almost real-time using machine learning or other analytical methods: the system could potentially autotune sample preparation of single-cells 1000, nuclei 1050 or other cellular components using singulation and viability metrics or production metrics such as the concentration of cellular components.

Figure 41:
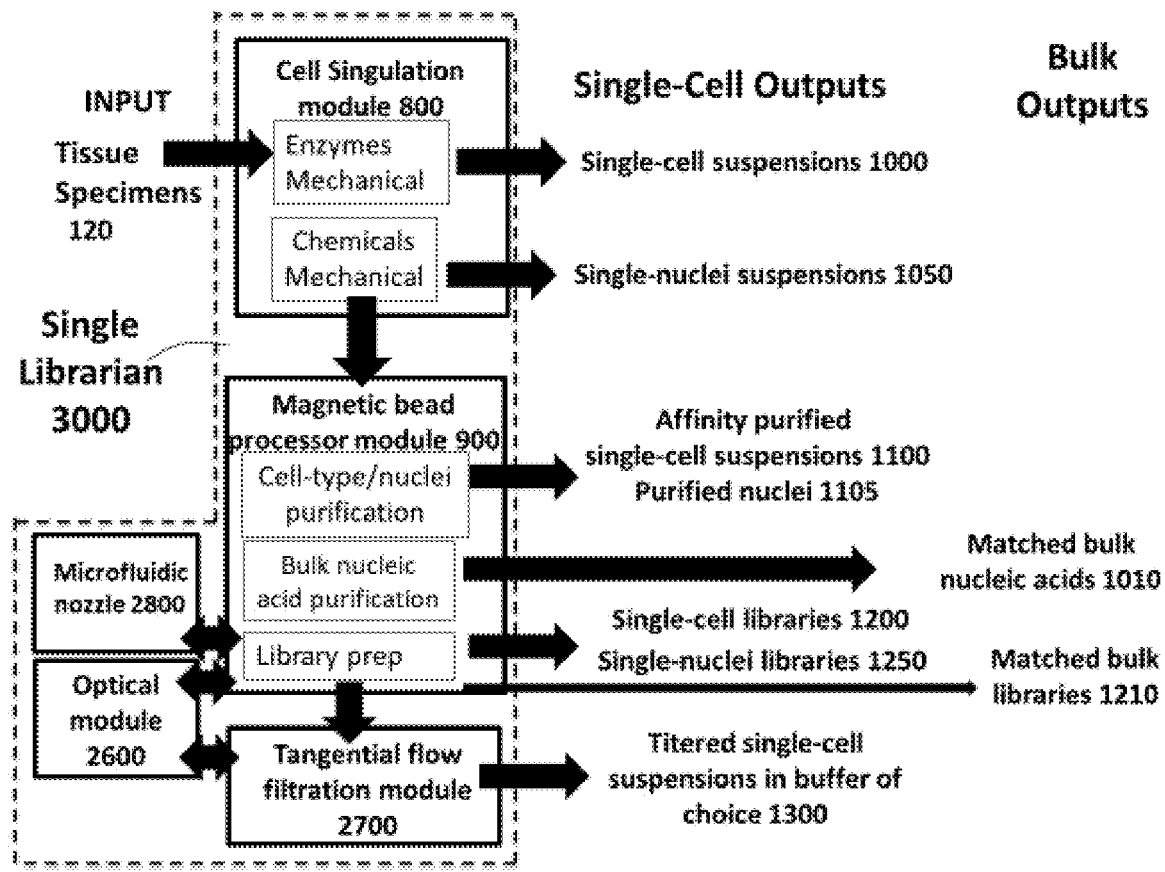
FIG. 41 shows a Single Librarian embodiment with the workflow integrated and automated for multiple steps from tissue to single-cell libraries and other libraries, such as bulk nucleic acid libraries.
Figure 43:
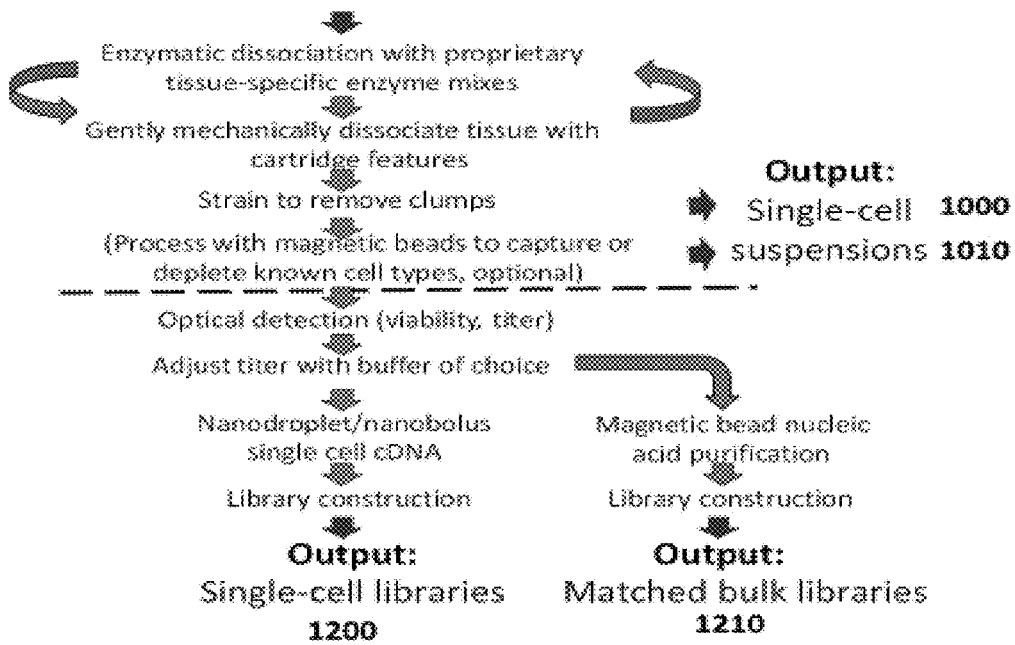
FIG. 43 is an exemplary workflow for the Single Librarian.

The Single Librarian 3000 embodiment as shown in FIG. 41 and an exemplary workflow shown in FIG. 43 adds capabilities to produce 1) titered single-cell suspensions 1300 that have been imaged and the titer adjusted in the buffer for downstream processing, 2) matched bulk nucleic acid preparations 1010, 3) single-cell libraries 1200, 4) single nuclei libraries 1250, and 5) matched bulk libraries 1210. Bulk is used to refer to preparations where more than one and frequently numerous single cells have been pooled or processed together and the individual signals such as DNA or RNA sequence are no longer distinguishable except as a composite signal. Matched is used to mean the nucleic acid preparation or library can be a bulk preparation or library that is from part of a batch of single cells 1000 or nuclei 1050 that are used to create a single cell library 1200 or single nuclei library 1250 and can serve as the bulk aggregated control for the single cells 1000 or nuclei 1050.

In a preferred embodiment, the Single Librarian 3000 can be configured to process any number of tissue samples automatically with tissue-specific disposable cartridges and enzymatic formulations to produce single-cell 1000 and nuclei 1050 suspensions and libraries, such a single sample, or four, or eight, or 12, or 96, or 384, or more samples. The processing time for single-cell 1000 or nuclei 1050 suspensions can be less than 2 min, or less than ten min, or less than 30 min, or less than two hours or less than four hours or other times. The processing can use optimized enzyme formulations for the production of single-cells 1000 or nuclei 1050. Magnetic bead processing can purify cell types, or nuclei, or organelles, or nucleic acids, or link biochemical reactions for library preparation.

Figure 42:
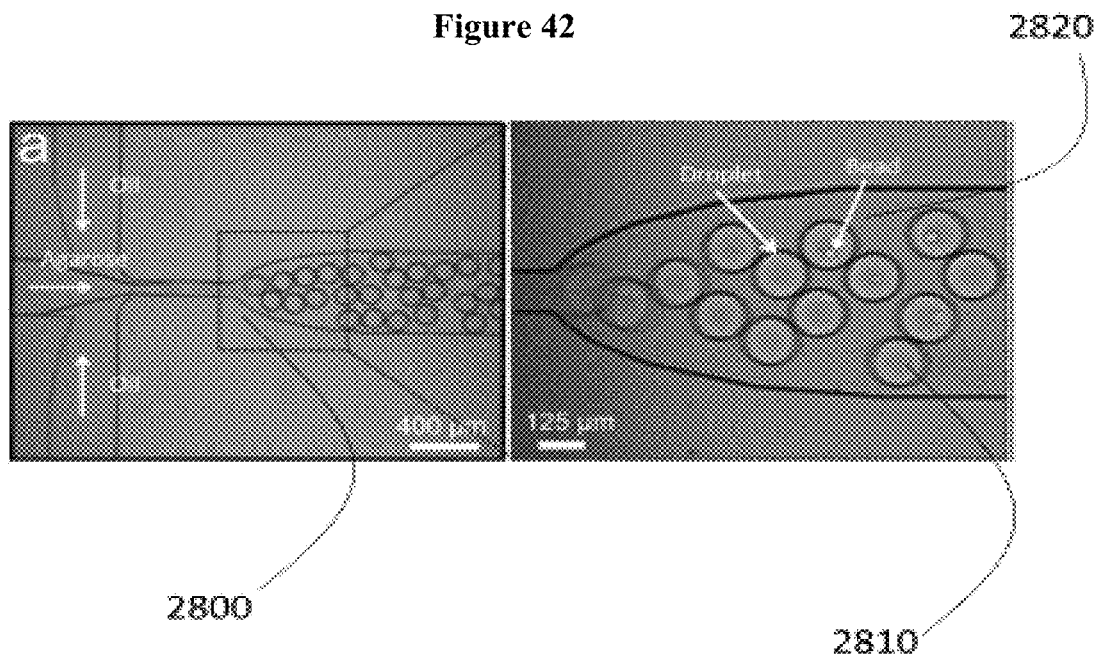
FIG. 42 is an example of a microfluidic nozzle used to create nanodroplets with beads and single-cells.

Nanodroplets without single-cells 2810 or with single-cells 2820 can be produced with microfluidic nozzles 2800, as shown in FIG. 42, or nanoboluses can be produced by using modular microfluidic connectors 620, three line connectors with a "T", or other configurations with the boluses being created as the aqueous single cells 1000 or nuclei 1050 or other sample produced by the Enhanced Singulator System 2500 go through the nozzle with an emulsion oil introduced through the side channels. While FIG. 42 shows the sample in agarose, in many implementations the single cells 1000 can be in a buffer without agarose. Emulsion oils are comprised of immiscible fluids (such as Fluorinert®; mineral oil; silicone-based oil; fluorinated oils; Droplet Generation Oil (Biorad, #1863005); emulsion oil (Life Technologies, Part No. 4469000); 73% Tegosoft DEC (Diethylhexyl Carbonate), 20% mineral oil, and 7% ABIL WE;

0.12% Span (v/v), 0.00325% Tween 80 (v/v), 0.0000125% Triton X-100 (v/v) in mineral oil; and other formulations.

An optical module 2600 can determine titer, viability, and QC samples during preparation, and the information can used for real-time process optimization by adjusting parameters comprising temperature, enzyme concentration and formulation including purified enzymes and use of acetate counterion salts in buffers and osmoprotectants such as glycine betaine, proline, glutamate, threhalose, etc. or chemicals and conditions.

The Single Librarian 3000 embodiment can integrate the workflows and processing of solid tissues from raw specimens to genomic samples to de-skill the workflow for single-cell sequencing and standardize production of single-cell suspensions and libraries. This will help researchers at laboratories in educational and research institutions, biopharmaceuticals, and applied markets (e.g., food testing, agriculture, animal sciences, etc.), and ultimately the clinical community to access single-cell sequencing and to NGS sample preparation for tissue.

The Single Librarian 3000 embodiment can function as follows in one embodiment, as shown in the workflow outlined in FIG. 43 for single cells. Tissue specimen 120 is added to cartridge 200 in the Cell Singulator module 800 where mechanical and enzymatic or chemical dissociation occurs as described above. The resultant single-cell 1000 or nuclei 1050 suspension or other products is strained and can then be optionally affinity purified in Magnet module 900. To produce matched bulk nucleic acid, an aliquot of the single-cell 1000 or nuclei 1050 suspension can be moved from Pre-Processing Chamber 440 to Processing Chamber 460. The aliquot of single-cells can have 7 M guanidine, sodium isocyanate, or other chaotrophs added along with paramagnetic beads such as SPRI beads (Beckman Coulter), Dynabeads (Thermo Fisher), or many other beads with COOH or other surface coatings or no coatings. The tissue specimen 120 can also be lysed directly without producing single cells 1000 or nuclei 1050 as an intermediary step. Alternatively, a lysis agent can be added and then the freed nucleic acid precipitated upon the beads using salt and polyethylene glycol or other chemistries. The amount of beads can be chosen to be limit the amount of nucleic acids 1072 that can bind, thereby normalizing the nucleic acid concentration. The chaotroph will lyse the cells, releasing the nucleic acid 1072 which is then forced onto the bead surface in a standard bead-based nucleic acid purification. The nucleic acid 1072 can be washed, such as with 70% ethanol, one or more times. If desired, the nucleic acid can be eluted into a buffer such as 10 mM Tris HCl or water to form matched bulk nucleic acid 1010 which can be output for off instrument processes or used as the starting material for a matched bulk nucleic acid library 1210. To process matched bulk nucleic acid 1010 into matched bulk nucleic acid library 1210, the matched bulk nucleic acid 1010 is processed differently for DNA and RNA libraries.

DNA Library Production Using Tagmentation

Libraries for NGS can be prepared using tagmentation with transposons including the Nextera Tagmentation (http://www.epibio.com/docsidefault-source/protocols/nextera-dna-sample-prep-kit-(illumina—compatible) .pdf?sfvrsn=4). In this embodiment, referring to FIG. 44, double stranded DNA 820 is produced in Processing Chamber 460 and transposons, e.g., Nextera enzyme, reaction mix, and water are added by syringe pump 2130. The reaction is incubated for example at 55° C. for 5 min. A bead purification is performed using Magnetic module 900 to remove reactants and purify the double stranded product with transposon inserted into the DNA on the beads which are still in the Processing Chamber 460. Syringe pump 2130 is used to add Nuclease-Free Water, Nextera Adaptor 2 (or other barcoded adapters), Nextera PCR Enzyme, PCR Buffer, and Nextera Primer Cocktail. If the Processing Chamber 460 also has a thermal cycling capability in the instrument with cartridge Peltier 1440, nine cycles of PCR can be performed. A bead purification is performed to remove reactants and purify the double stranded DNA product before elution into buffer or water. The double stranded bulk DNA library 1010 is now ready to QC and bridge amplification on the flow cell of the sequencer. Many variations of the method described here are within the instant disclosure and are obvious to one skilled in the art.

DNA Library Production Using Polishing, End Repair, and Ligation.

Figure 45:
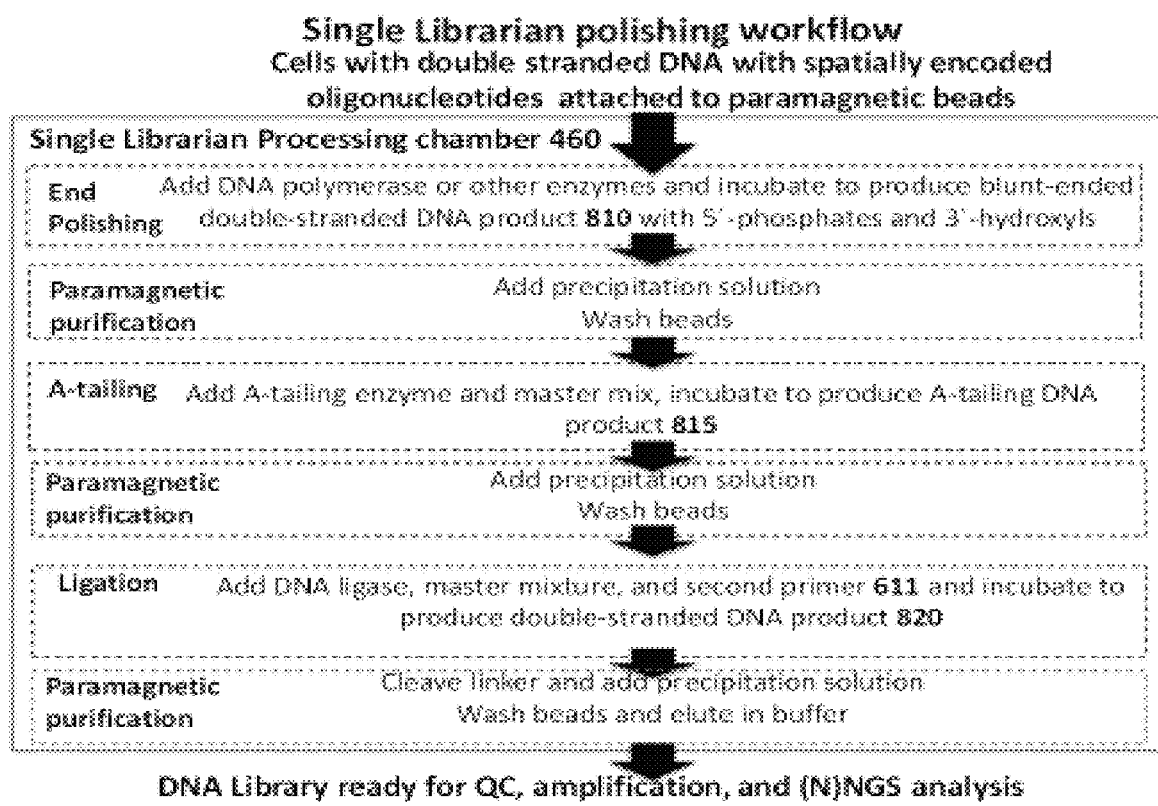
FIG. 45 shows an example workflow of library preparation from double stranded DNA.

Another embodiment of the workflow to produce libraries is illustrated in FIG. 45. Double-stranded DNA attached to a bead, such as double stranded cDNA attached to bead 684, or bulk nucleic acid absorbed onto beads, can if needed be fragmented enzymatically, e.g. Fragmentase® (New England Biolabs, M0348), with restriction enzymes, nucleases, or other enzymes, or chemically. Enzymes or chemicals can be added to Processing Chamber 460 by syringe pump 2130 and incubated. Following fragmentation, the now fragmented nucleic acid can be forced onto paramagnetic beads, the magnetic beads captured, and the nucleic acid 1072 purified by washes.

The fragmented nucleic acid can be end-polished in Processing Chamber 460 by addition of reaction mix and enzymes, for example, the NEBNext® End Repair Module (NEB E 6050S) reagents, from syringe pump 2130 to generate end-polished DNA product 810, an end-polished, blunt-ended double-stranded DNA having 5"-phosphates and 3"-hydroxyls; other kits such as Agilent PCR polishing kit 200409 and other enzymology can perform the same function. Following end polishing, a magnetic separation is performed in Processing Chamber 460 to remove reactants and enzymes from end-polished DNA product 810.

Following polishing, A-tailing is used to generate fragments ready to ligate with a primer with a complementary T overhang and to prevent concatamer formation during ligation. A-tailing can be performed using commercially available kits such as the NEBNext® dA-Tailing Module (NEB E6053S) with enzyme and master mix added from the syringe pump 2130 to Processing Chamber 460 containing end-polished DNA product 810 and incubating the reaction to produce blunt-ended double-stranded DNA having 5"-phosphates with an A residue overhang on the 3' end, A-tailing DNA product 815. Following A tailing, a magnetic separation is performed in Processing Chamber 460 to remove reactants and enzymes from A-tailing DNA product 815.

A double stranded second primer 611 with a complementary T overhang can be ligated by DNA ligase onto the 3' end of A-tailing DNA product 815. DNA ligase, DNA ligase reaction mix, and second primer 611 (such as NEB Next Adapter) are added by syringe pump 2130 to Processing Chamber 460 and incubating the reaction. DNA ligation can be performed using commercially available kits or reactions, e.g. NEBNext® Quick Ligation Module, NEB E6056S. Following DNA ligation, a magnetic separation is performed in Processing Chamber 460 to remove reactants and enzymes. The product is now a double stranded DNA product 820 that has incorporated second sequencing primer 611 or can have two adapters attached depending on the workflow. The product of the ligation can be a matched bulk nucleic acid library 1210. The fragment sizes for the downstream NGS analysis can be selected by a two step 'heart cut' precipitation onto beads, with one cut selecting for fragments longer than a lower cutoff, e.g., 400 bases, and the second cut selecting for fragments shorter than a high cutoff, e.g., 600 bases.

For bulk RNA, after nucleic acid purification to produce bulk matched nucleic acid 1010, the RNA can optionally be fragmented by addition of metal cations from syringe pump 2130 to Processing Chamber 460 followed by magnetic bead purification to produce purified fragmented nucleic acid. The polyadenylated RNA can then be converted to cDNA using a poly T primer and reverse transcriptase in Processing Chamber 460. The cDNA can now be treated as described above for DNA Library Production using polishing, end repair, and ligation or with Tagmentation to produce bulk matched RNA libraries.

Production of Single-Cell Libraries from Polyadenylated mRNA in Single-Cell or Nuclei Suspensions.

Figure 46:
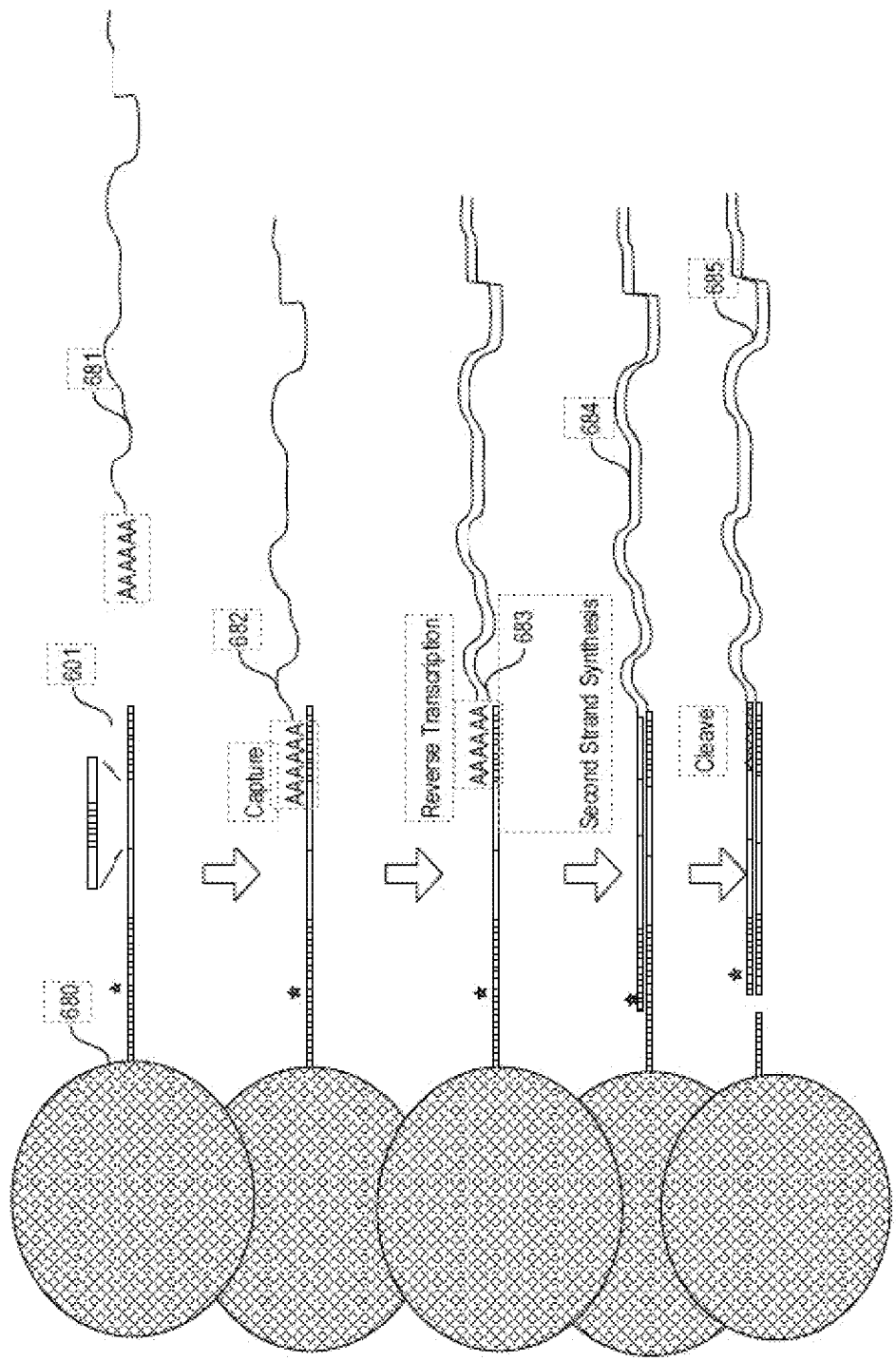
FIG. 46 illustrates the processing of mRNA to cDNA on a bead.

In one embodiment of the single-cell 1000 or nuclei 1050 library workflow, after production of single-cell suspensions 1000 in the Preprocessing Chamber 440 in the Cell Singulation module 800, the cells are moved through the strainer into the Processing Chamber 460. Referring to FIG. 46, the single-cell 1000 or nuclei 1050 suspensions can be optionally purified for specific cell type using affinity purification in Magnetic module 900. The single-cell suspension is then counted in the Optical module 2600, and the titer and buffer adjusted as needed in the TFF module 2700.

The single-cell suspension in appropriate buffer is then mixed with beads which can have poly T containing primers embedded for mRNA, and moved to a microfluidic nozzle 2800, e.g., as shown in FIG. 42 either connected through fluidics or using the 2 axis robot 2665 and pipettor 2660 to deliver the sample to the microfluidic nozzle 2800. The single-cell suspension and beads are passed through microfluidic nozzle 2800 to produce nanodroplets 2810, some of which will contain a bead 2820 and some nanodroplets containing both a bead and a single-cell.

The processing of the single-cells can be as described in International Patent Publication WO 2017/075,293 (Jovanovich and Wagner, "Method and apparatus for encoding cellular spatial position information"), the contents of which are incorporated herein in their entirety. The same methods can be utilized in the Single Librarian without the use of spatial barcodes.

A preferred embodiment for mRNA is described in more detail. In one embodiment, single channel fluidics are used. Referring to FIG. 46, barcoded oligonucleotide-functionalized beads 680 with a poly T sequence as the capture region on oligonucleotide 601 in lysis/reverse transcriptase mix is added to the single-cell suspension. Monodisperse nanodroplets from single cells with beads with lysis/RT mix, are produced using a nozzle 2800. The output of the microfluidic nozzle 2800 is moved back to the Processing Chamber 460 if needed. Cells are lysed by lysis buffer, heating, or other methods and polyadenylated mRNA 681 captured onto the oligonucleotide to form captured mRNA structure 682. The oligonucleotides 601 can be barcoded for spatial barcode information 607 if desired as well as cellular barcodes 608 and molecule barcodes 609. Amplification primer 604 and sequencing primer 605 may be included on the oligonucleotide, or may be added in downstream library preparation methods as needed. The amplification primers 604 can be for T7 polymerase for amplified RNA production, PCR, rolling circle transcription-based amplification, rapid amplification of cDNA ends, continuous flow amplification, and other amplification methods.

After lysis and capture of the mRNA onto the poly T, a reverse transcriptase reaction is performed in Processing Chamber 460 to produce cDNA attached to bead 683, formed from the mRNA, and now containing the cellular and molecular barcodes as well as the optional spatial barcode in addition to any sequencing and amplification primers attached to the bead 680 through an optional cleavable linker. Cleavage of the linker can release the cDNA from the bead when desired. A photocleavable or chemical cleavable linker and fluorescent tag(s) to aid in quality control and process development is included in the instant disclosure. As required, fragmentation of the RNA or cDNA can be performed using methods comprised of chemical, biochemical, and physical methods. Alternative preferred embodiments include performing an RNA ligase reaction to covalently join the mRNA to one strand of the double stranded oligonucleotide after lysis and capture of the mRNA onto oligonucleotide-functionalized beads 680 with a poly T sequence as the capture region 610, or ligating RNA to a single stranded RNA or DNA attached to the bead. The produced cDNA can then be used in the library preparation as described above for bulk nucleic acid library preparation. In an alternative embodiment, the cDNA still attached to the bead can be ligated with a second primer or adapter to produce a library. In some embodiments the cDNA can be directly readout on a nanopore or other sequencer.

Determination of Amplification of Nucleic Acid and Normalization Thereof.

In many applications in genomics, an amplification step is required to produce enough material for the downstream analysis instrument. For example, in NGS after library creation, a PCR step may be required before loading the DNA sequencer. While PCR amplification is straightforward, many targets may amplify unevenly, leading to uncertainty about the actual amount of the target in the unamplified library. This prevents determination of the absolute amount of the target.

scRNA-Seq is a novel method to sequence mRNA from single-cells. After capture of the mRNA typically onto a bead with a poly T sequence, the mRNA is processed with reverse transcriptase to produce cDNA using primers that may have barcodes for the cell and the molecules that are then made into a library.

The amount of amplification for each molecule can be measured and used to normalize the resulting sequencing data to minimize amplification or readout biases. To do this, the PCR amplification primer can incorporate a set of enumeration barcodes such as a three base long barcode that is random. Once the fragment is amplified and sequenced, the number of bases that appear in the enumeration barcodes can be counted to determine the degree of amplification. A three base enumeration barcode would be useful for up to a 64-fold amplification: enumeration barcodes with more bases could extend the range as high as desired. For the example where three bases are used in the enumeration barcode, the representation of each of the 64 possible sequences is determined and that number is used to normalize the representation of that molecule in the final NGS data, such that if 32 combinations were found in a first sequence and 16 in a second sequence, the depth of the first sequence would be adjusted by a factor of two with respect to the second sequence to normalize for the amplification and readout biases.

Example: Sample-to-Answer System

Figure 47:
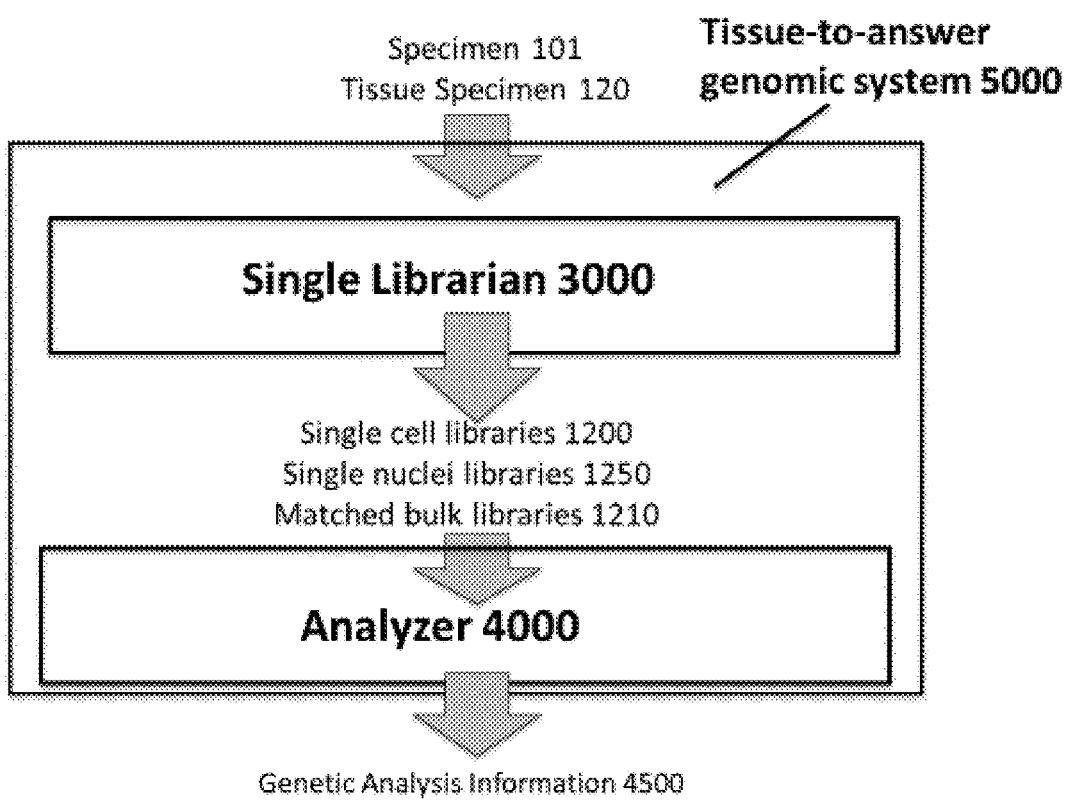
FIG. 47 shows a sample-to-answer embodiment configured to process tissue into genetic information.

In other embodiments a Sample Processing System 50 is combined with an analyzer 4000 to create a sample to answer system. In a preferred embodiment, referring to FIG. 47, the Single Librarian 3000 is physically integrated with a genetic analyzer such as a NGS system. In this embodiment, the Single Librarian 3000 processes a specimen 101, preferably a tissue specimen 120, into single cell libraries 1200, or nuclei libraries 1250 or bulk libraries 1210 or other materials which then can be analyzed on an genetic analyzer 4000 comprised of a nucleic acid sequencer, more preferably an NGS or NNGS sequencer, to produce genetic analysis information 4500 such as DNA sequence, or RNA sequence, or single nucleotide variations, or nucleic acid modifications. The prepared library is fluidically moved into the analyzer 4000 and delivered to its flowcell or other input for analysis or further processing such as bridge amplification. This may replace the on-board library preparation found on some NGS sequencers or directly couple to a nanopore or other analytical device.

This produces a tissue-to-answer genomic system 5000 capable of performing bulk sequencing of tissue, or single cell sequencing of tissue, or single nuclei sequencing of tissue, or mitochondria sequencing of tissue, or other sample-to-answer genetic analysis for nucleic acids 1072, DNA 1073, RNA 1074 comprised of microRNAs, long non-coding RNA, ribosomal RNA, message RNAs, etc.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or."

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

The invention claimed is:

1. A method of analyzing subcellular organelles comprising:
   (a) providing a tissue sample or cell suspension sample;
   (b) performing mechanical or chemical disruption of the tissue or cell suspension sample in a chamber situated in a cartridge, while the cartridge is engaged with a cartridge interface of an instrument, to produce debris and released subcellular organelles in the chamber;
   (c) separating a plurality of the released subcellular organelles from a portion of the debris into a liquid suspension;
   (d) collecting the plurality of the released subcellular organelles in the liquid suspension; and
   (e) analyzing individual subcellular organelles from the plurality of released subcellular organelles.

2. The method of claim 1, wherein the providing a tissue sample or cell suspension sample comprises providing a tissue sample.

3. The method of claim 2, wherein the tissue sample comprises an organ or organ fragment.

4. The method of claim 3, wherein the organ or organ fragment is from one or more organs selected from the group consisting of: kidney, lung, spleen, liver, gut, and brain.

5. The method of claim 2, wherein the tissue sample is an organ or organ fragment that is 100 mg or less.

6. The method of claim 5, further comprising collecting at least 75,000 intact released subcellular organelles per mg of the organ or organ fragment.

7. The method of claim 6, wherein the organ or organ fragment is from kidney, lung, spleen, liver, brain or gut.

8. The method of claim 6, wherein the at least 75,000 intact released subcellular organelles per mg of the organ or organ fragment comprise at least 75,000 intact released nuclei per mg of the organ or organ fragment.

9. The method of claim 1, wherein the separating of the released subcellular organelles from a portion of the debris is automated.

10. The method of claim 6, wherein the at least 75,000 intact released subcellular organelles per mg of the organ or organ fragment comprise at least 75,000 intact released ribosomes or mitochondria, or combination thereof, per mg of the organ or organ fragment.

11. The method of claim 1, further comprising contacting the tissue sample with a detergent, surfactant, or enzyme prior to, during, or following the mechanical or chemical disruption of the tissue sample in the apparatus.

12. The method of claim 2, wherein the tissue sample is an organ fragment that is 25 mg or less.

13. The method of claim 2, wherein the tissue sample comprises tumor tissue.

14. The method of claim 2, wherein the tissue sample comprises frozen tissue.

15. The method of claim 2, wherein the tissue sample comprises fixed tissue.

16. The method of claim 2, wherein the performing mechanical or chemical disruption of the tissue sample comprises automatically performing mechanical disruption of the tissue sample.

17. The method of claim 1, wherein the tissue sample or cell suspension sample comprises a cell suspension comprising tumor cells.

18. The method of claim 1, wherein the collecting the plurality of the released subcellular organelles in the liquid suspension comprises collecting individual nuclei in the liquid suspension.

19. The method of claim 1, wherein the collecting the plurality of the released subcellular organelles in the liquid suspension comprises collecting ribosomes or mitochondria in the liquid suspension.

20. The method of claim 1, wherein the collecting the plurality of the released subcellular organelles in the liquid suspension comprises collecting at least 75,000 released intact nuclei per mg of the tissue sample.

21. The method of claim 1, wherein the collecting the plurality of the released subcellular organelles in the liquid suspension comprises collecting between 75,000 to 1,600,000 nuclei per mg of the tissue sample.

22. The method of claim 1, wherein the collecting the plurality of the released subcellular organelles in the liquid suspension comprises automatically moving the released subcellular organelles in the liquid suspension into a strain chamber comprising a strainer or filter.

23. The method of claim 1, wherein the cartridge is disposable.

24. The method of claim 1, wherein analyzing the released subcellular organelles comprises performing optical imaging of the released subcellular organelles.

25. The method of claim 1, wherein analyzing the released subcellular organelles comprises performing sequencing of DNA or RNA derived from the released subcellular organelles.

26. The method of claim 6, wherein analyzing individual subcellular organelles from the plurality of released subcellular organelles comprises performing optical imaging to measure titer, clumping, viability, or a combination thereof of the released subcellular organelles.

27. The method of claim 8, wherein analyzing individual subcellular organelles from the plurality of released subcellular organelles comprises performing sequencing of DNA or RNA derived from a portion of the at least 75,000 intact released nuclei per mg of the organ or organ fragment.

28. A sample processing method comprising:
(a) providing a tissue sample, wherein the tissue sample is an organ fragment that is 20 mg or less;
(b) loading the tissue sample into a chamber situated in a cartridge;
(c) prior to, or following (b), engaging the cartridge with a cartridge interface of an instrument;
(d) performing mechanical disruption of the sample in the chamber to produce material comprising debris and released cells;
(e) separating the released cells from a portion of the debris; and
(f) collecting at least 20,000 viable released cells per mg of the tissue sample.

29. The method of claim 28, wherein the organ fragment is a kidney, lung, spleen, liver, or gut fragment.

30. The method of claim 28, further comprising analyzing the released cells.

* * * * *